United States Patent
Hwang

(10) Patent No.: US 9,420,998 B2
(45) Date of Patent: Aug. 23, 2016

(54) SYSTEMS AND METHODS FOR BEAM ENHANCEMENT

(71) Applicant: FUJIFILM Sonosite, Inc., Bothell, WA (US)

(72) Inventor: Juin-Jet Hwang, Mercer Island, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 69 days.

(21) Appl. No.: 14/466,902

(22) Filed: Aug. 22, 2014

(65) Prior Publication Data

US 2014/0363068 A1 Dec. 11, 2014

Related U.S. Application Data

(62) Division of application No. 13/508,966, filed as application No. PCT/US2010/056000 on Nov. 9, 2010, now Pat. No. 8,876,719.

(60) Provisional application No. 61/259,346, filed on Nov. 9, 2009, provisional application No. 61/259,938, filed on Nov. 10, 2009.

(51) Int. Cl.
*G06K 9/00* (2006.01)
*A61B 8/08* (2006.01)
(Continued)

(52) U.S. Cl.
CPC ......... *A61B 8/5207* (2013.01); *G01S 7/52047* (2013.01); *G10K 11/341* (2013.01); *G01S 15/8977* (2013.01)

(58) Field of Classification Search
CPC .................................. A61B 5/00; G01S 7/00
USPC ............ 382/128–134; 378/4, 8, 21–27, 901; 600/407, 443, 437, 447, 458
See application file for complete search history.

(56) References Cited

U.S. PATENT DOCUMENTS 5,570,691 A 11/1996 Wright et al.
5,601,083 A 2/1997 Anderson
(Continued)

FOREIGN PATENT DOCUMENTS

JP 2001187054 7/2001
JP 2001238883 9/2001
(Continued)

OTHER PUBLICATIONS

European Patent Office, Extended European Search Report, EP Patent Application 10829276.4, mailed Sep. 24, 2014, 9 pages.
(Continued)

*Primary Examiner* — Abolfazl Tabatabai
(74) *Attorney, Agent, or Firm* — Perkins Coie LLP

(57) ABSTRACT

Beam enhancement through sidelobe reduction and/or mainlobe sharpening is shown. Embodiments utilize dynamic resolution, improved dynamic resolution, and/or enhanced dynamic resolution techniques to synthesize beams, such as ultrasonic beams used in ultrasonic imaging, having desired attributes. Embodiments simultaneously form a first sample beam and a second or auxiliary sample beam for every sample to synthesize enhanced scan beams. According to a dynamic resolution techniques herein a new beam may be formed from the sum of the two sample beams. A synthesized dynamic resolution beam of embodiments has reduced sidelobes with relatively little or no spread of the mainlobe. An enhanced dynamic resolution beam sharpening function can be applied to provide a further enhanced beam, such as to further narrow the mainlobe.

29 Claims, 35 Drawing Sheets

(51) Int. Cl.
  *G01S 7/52* (2006.01)
  *G10K 11/34* (2006.01)
  *A61B 8/00* (2006.01)
  *G01S 15/89* (2006.01)

(56) References Cited

U.S. PATENT DOCUMENTS

| | | | |
|---|---|---|---|
| 5,902,243 | A | 5/1999 | Holley et al. |
| 5,911,692 | A | 6/1999 | Hussain et al. |
| 5,935,068 | A | 8/1999 | Zhu et al. |
| 6,014,897 | A | 1/2000 | Mo |
| 6,023,977 | A | 2/2000 | Langdon et al. |
| 6,111,535 | A | 8/2000 | Smith |
| 6,131,458 | A | 10/2000 | Langdon et al. |
| 6,135,963 | A | 10/2000 | Haider |
| 6,142,946 | A | 11/2000 | Hwang et al. |
| 6,206,833 | B1 | 3/2001 | Christopher |
| 6,282,963 | B1 | 9/2001 | Haider |
| 6,312,379 | B1 | 11/2001 | Bradley et al. |
| 6,312,384 | B1 | 11/2001 | Chiao |
| 6,315,723 | B1 | 11/2001 | Robinson et al. |
| 6,432,056 | B1 | 8/2002 | Cooley et al. |
| 6,485,423 | B2 | 11/2002 | Angelsen et al. |
| 6,487,433 | B2 | 11/2002 | Chiao |
| 6,582,369 | B1 | 6/2003 | Huang et al. |
| 6,638,227 | B2 | 10/2003 | Bae |
| 6,658,141 | B1 | 12/2003 | Jeong |
| 6,736,780 | B2 | 5/2004 | Song et al. |
| 6,786,097 | B2 | 9/2004 | Song et al. |
| 6,905,465 | B2 | 6/2005 | Angelsen et al. |
| 6,905,467 | B2 * | 6/2005 | Bradley .............. G01S 15/895 600/443 |
| 7,004,905 | B2 | 2/2006 | Christopher |
| 7,066,886 | B2 | 6/2006 | Song et al. |
| 7,104,956 | B1 | 9/2006 | Christopher |
| 7,273,455 | B2 | 9/2007 | Angelsen et al. |
| 7,513,870 | B2 | 4/2009 | Christopher |
| 7,811,233 | B2 | 10/2010 | Christopher |
| 7,876,973 | B2 | 1/2011 | Fairbanks |
| 7,889,787 | B2 | 2/2011 | Shifrin |
| 7,957,609 | B2 | 6/2011 | Lu et al. |
| 7,978,926 | B2 | 7/2011 | Fairbanks et al. |
| 8,045,777 | B2 | 10/2011 | Zwirn |
| 8,254,654 | B2 * | 8/2012 | Yen .............. G01S 7/52047 382/128 |
| 8,876,719 | B2 | 11/2014 | Hwang |
| 2001/0051771 | A1 | 12/2001 | Bradley et al. |
| 2002/0002333 | A1 | 1/2002 | Angelsen et al. |
| 2002/0091317 | A1 | 7/2002 | Chiao |
| 2003/0018261 | A1 | 1/2003 | Bae |
| 2003/0125628 | A1 | 7/2003 | Song et al. |
| 2003/0199763 | A1 | 10/2003 | Angelsen et al. |
| 2004/0034305 | A1 | 2/2004 | Song et al. |
| 2004/0249280 | A1 | 12/2004 | Christopher |
| 2005/0033168 | A1 | 2/2005 | Shifrin |
| 2005/0033170 | A1 | 2/2005 | Angelsen et al. |
| 2005/0033180 | A1 | 2/2005 | Christopher |
| 2005/0096544 | A1 | 5/2005 | Hao et al. |
| 2005/0277835 | A1 | 12/2005 | Angelsen et al. |
| 2006/0052699 | A1 | 3/2006 | Angelsen et al. |
| 2006/0074320 | A1 | 4/2006 | Yoo et al. |
| 2006/0241433 | A1 | 10/2006 | Christopher |
| 2007/0016022 | A1 | 1/2007 | Blalock et al. |
| 2007/0109179 | A1 | 5/2007 | Werntz et al. |
| 2007/0160278 | A1 | 7/2007 | Fairbanks et al. |
| 2008/0200809 | A1 | 8/2008 | Shifrin |
| 2008/0253502 | A1 | 10/2008 | Ziegler et al. |
| 2008/0262352 | A1 | 10/2008 | Zwirn |
| 2009/0066727 | A1 | 3/2009 | Lu et al. |
| 2009/0105591 | A1 | 4/2009 | Christopher |
| 2009/0141957 | A1 * | 6/2009 | Yen .............. G01S 7/52047 382/131 |
| 2009/0156936 | A1 | 6/2009 | Chiang et al. |
| 2009/0299184 | A1 | 12/2009 | Walker et al. |
| 2010/0142781 | A1 | 6/2010 | Walker et al. |
| 2010/0174194 | A1 | 7/2010 | Chiang et al. |
| 2011/0116728 | A1 | 5/2011 | Fairbanks et al. |
| 2011/0301464 | A1 | 12/2011 | Yoo et al. |
| 2012/0157851 | A1 | 6/2012 | Zwirn |

FOREIGN PATENT DOCUMENTS

| | | |
|---|---|---|
| JP | 2004242788 | 9/2004 |
| WO | WO-2007007414 | 1/2007 |
| WO | WO-2011057252 | 5/2011 |

OTHER PUBLICATIONS

Japanese Patent Office, Notice of Rejection, JP Patent Application 2012-538082, mailed Aug. 5, 2014, 6 pages.

Seo, Chi Hyung et al. "Sidelobe Suppression in Ultrasound Imaging using Dual Apodization with Cross-correlation." IEEE Transactions on Ultrasonics, Ferroelectrics and Frequency Control, vol. 55, No. 10, Oct. 2008, pp. 2198-2210.

State Intellectual Property of China, First Office Action, CN Patent Application 201080060936.3, mailed Jul. 18, 2014, 15 pages.

International Searching Authority, International Search Report, PCT Application PCT/US2010/056000, mailed Jan. 10, 2011, 2 pages.

International Searching Authority, Written Opinion, PCT Application PCT/US2010/056000, mailed Jan. 10, 2011, 6 pages.

* cited by examiner

ACQUIRE SIGNAL OF THE SINC BEAM $\vec{I_u}$

ACQUIRE SIGNAL OF THE COSINE BEAM $\vec{I_c}$

COMPUTE $\alpha$ AND OBTAIN THE DR BEAM $\vec{I_{DR}}$

FOR $\alpha = 1$
$\vec{I_{DR}} = \vec{I_u} + \vec{I_c}$

COMPUTE THE MINIMUM BETWEEN THE
$\vec{I}_{DR}$ AND $\vec{I}_c$: $\vec{M} = \varphi(\vec{I}_{DR})$ MIN $(|\vec{I}_{DR}|,|\vec{I}_c|)$ $\vec{M}$ SUBTRACT $\vec{M}$ FROM $\vec{I}_{DR}$ TO OBTAIN $\vec{I}_{uM}$
$\vec{I}_{uM} = \vec{I}_{DR} - \vec{M}$ $\vec{I}_{um}$ REMOVE $\vec{I}_{uM}$ FROM $\vec{I}_u$ TO OBTAIN $\vec{I}_{uS}$
$\vec{I}_{uS} = \vec{I}_u - \vec{I}_{uM}$ $\vec{I}_{uS}$ REMOVE $\vec{I}_{uM}$ FROM $\vec{I}_{DR}$ TO OBTAIN $\vec{I}_{\alpha S}$ $$\vec{I}_{\alpha S} = \vec{I}_{DR} - \vec{I}_{uM}$$

SCALING THE SIDE LOBE BY
MULTIPLYING $\gamma = 0.125$

ADDING THE MAIN LOBE SIGNAL
COMPONENT $\vec{I}_{uM}$ TO THE SCALED SIGNAL
COMPONENT $\gamma\vec{I}_{\alpha S}$ FROM THE SIDE LOBE $$\vec{I}_{uM} + \gamma\vec{I}_{\alpha S}$$

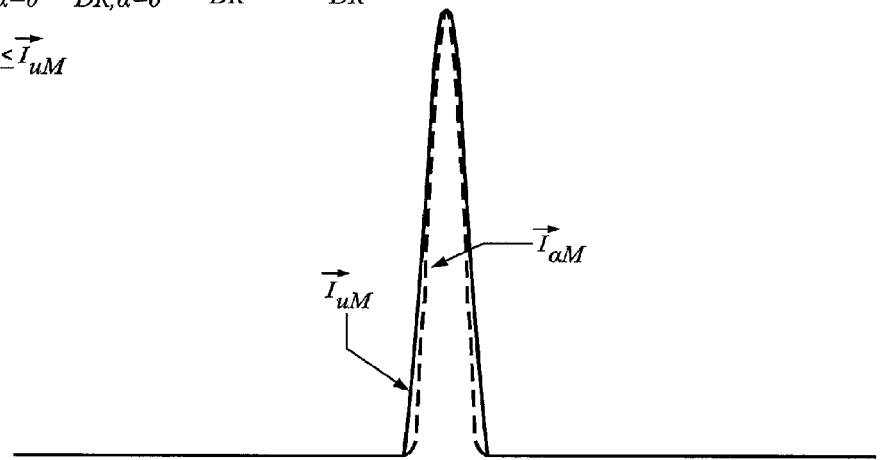
FIG. 6I(1)
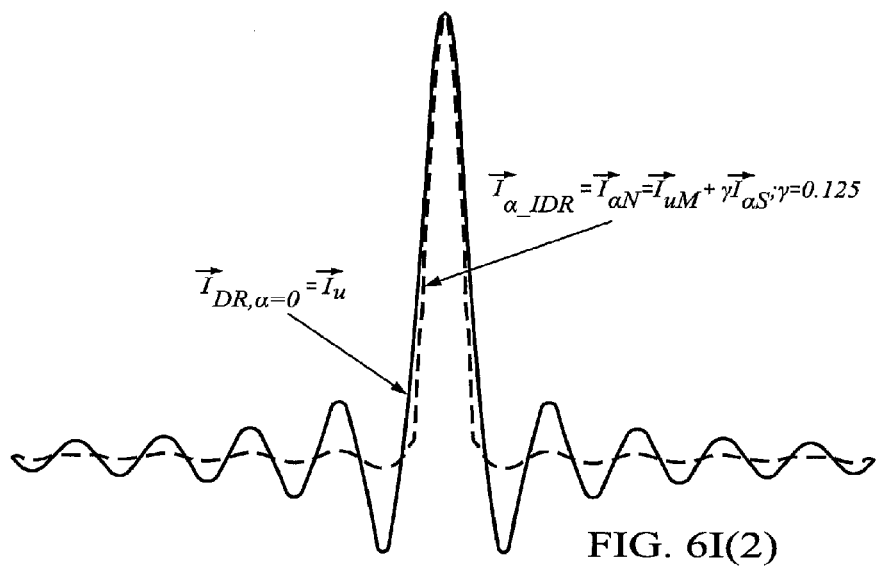
FIG. 6I(2)

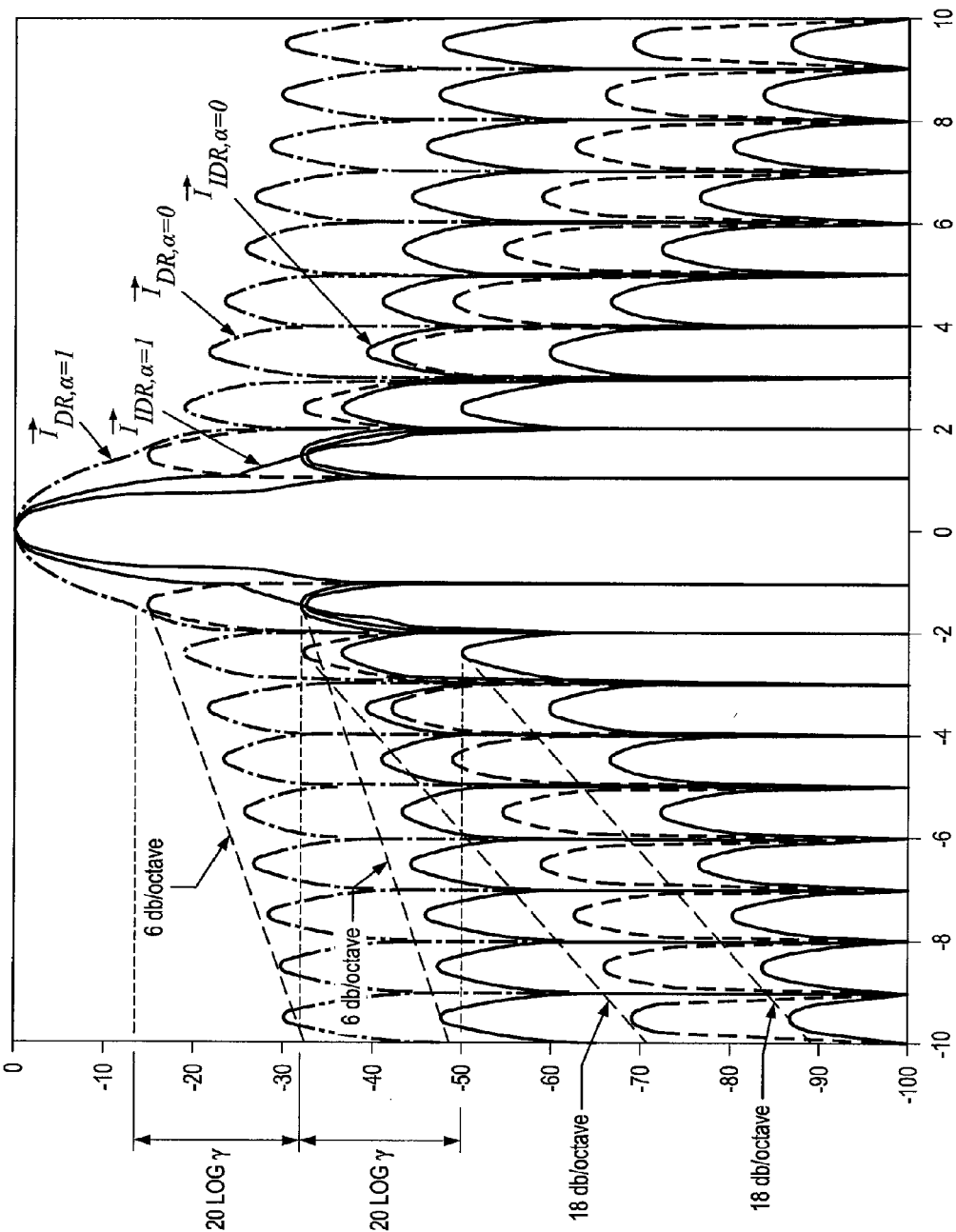
FIG. 6I(3)

FIG. 6J

SPLIT THE COMPONENT SIGNAL $\vec{I}_{uM}$ FROM THE MAIN LOBE INTO TWO COMPONENT SIGNALS $\vec{I}_{uM\_n}$ AND $\vec{I}_{uM\_S}$ BY TAKING THE $$\vec{I}_{uM\_n} = \vec{I}_{DR} - \varphi(\vec{I}_{DR}) \operatorname{MIN}\{|\vec{I}_{DR}|, \kappa|\vec{I}_c|\}$$

WHERE $\kappa = 2$

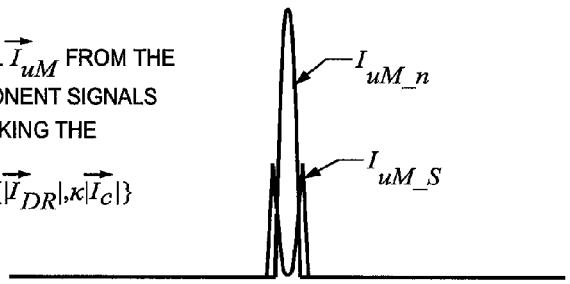

FIG. 6K

EFFECTIVE BEAM SHAPING FUNCTION $\psi(\theta)$ FOR MAIN LOBE SPLITTING

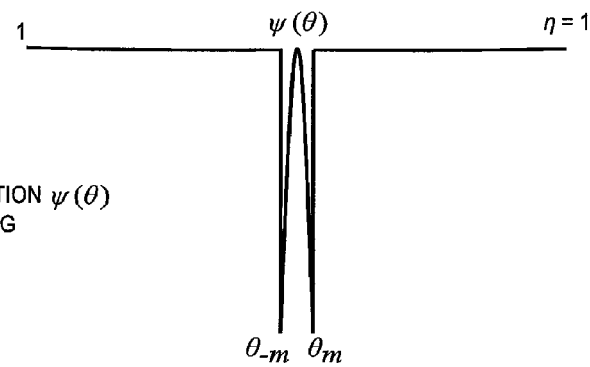

FIG. 6L

CALCULATE THE SIGNAL $\vec{I}_{XDR}$ BY WEIGHTED SUMMED COMPONENT SIGNALS $\vec{I}_{uM\_n}, \vec{I}_{uM\_S}$ AND $\vec{I}_{\alpha S}$.

$$\vec{I}_{XDR} = \mu \vec{I}_{uM\_n} + \rho \vec{I}_{uM\_S} + \gamma \vec{I}_{\alpha S}$$

FOR $\mu = 1; \rho = 0.0625; \gamma = 0.125;$

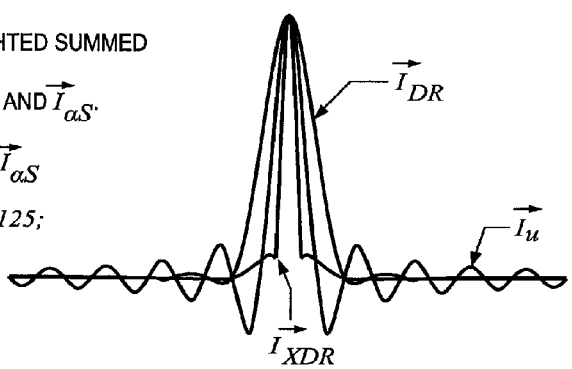

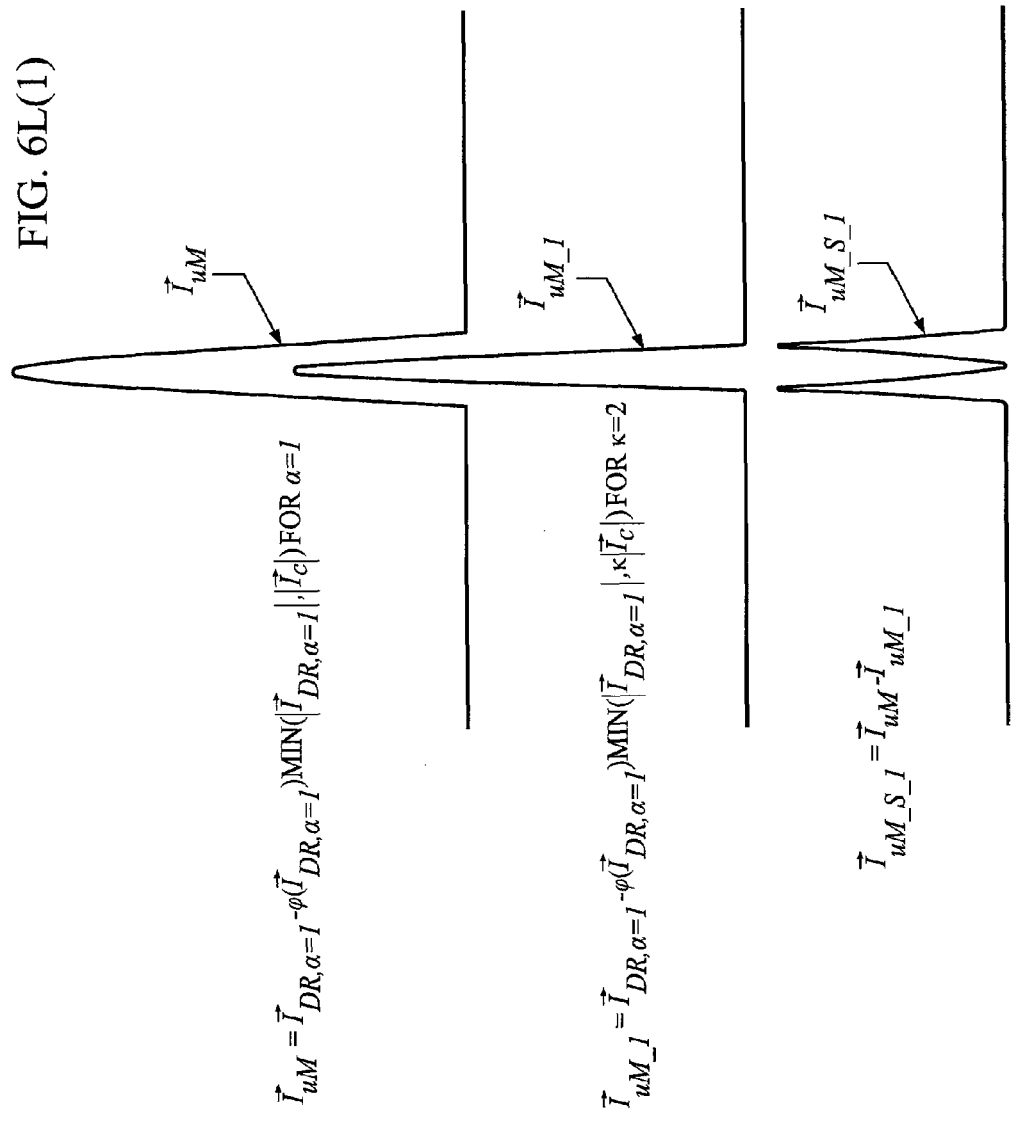
FIG. 6L(1)

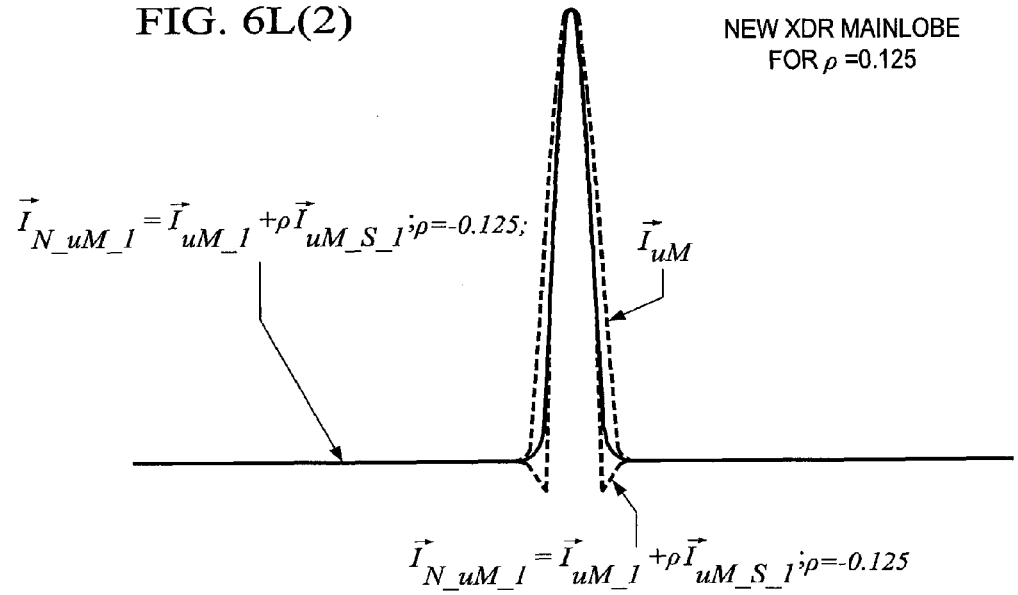
FIG. 6L(2)
NEW XDR MAINLOBE FOR $\rho = 0.125$
$\vec{I}_{N\_uM\_1} = \vec{I}_{uM\_1} + \rho \vec{I}_{uM\_S\_1}; \rho = -0.125;$
$\vec{I}_{uM}$
$\vec{I}_{N\_uM\_1} = \vec{I}_{uM\_1} + \rho \vec{I}_{uM\_S\_1}; \rho = -0.125$
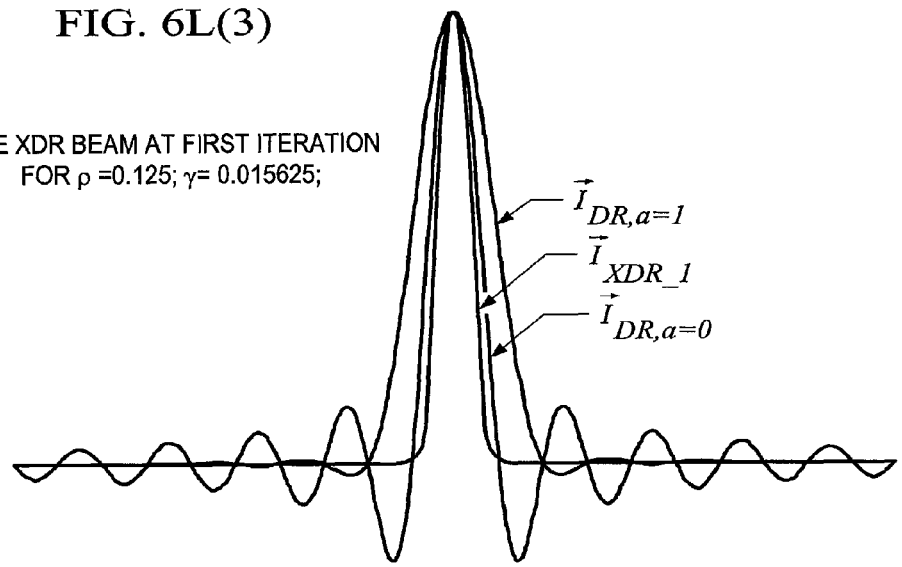
FIG. 6L(3)
THE XDR BEAM AT FIRST ITERATION FOR $\rho = 0.125; \gamma = 0.015625;$
$\vec{I}_{DR, a=1}$
$\vec{I}_{XDR\_1}$
$\vec{I}_{DR, a=0}$

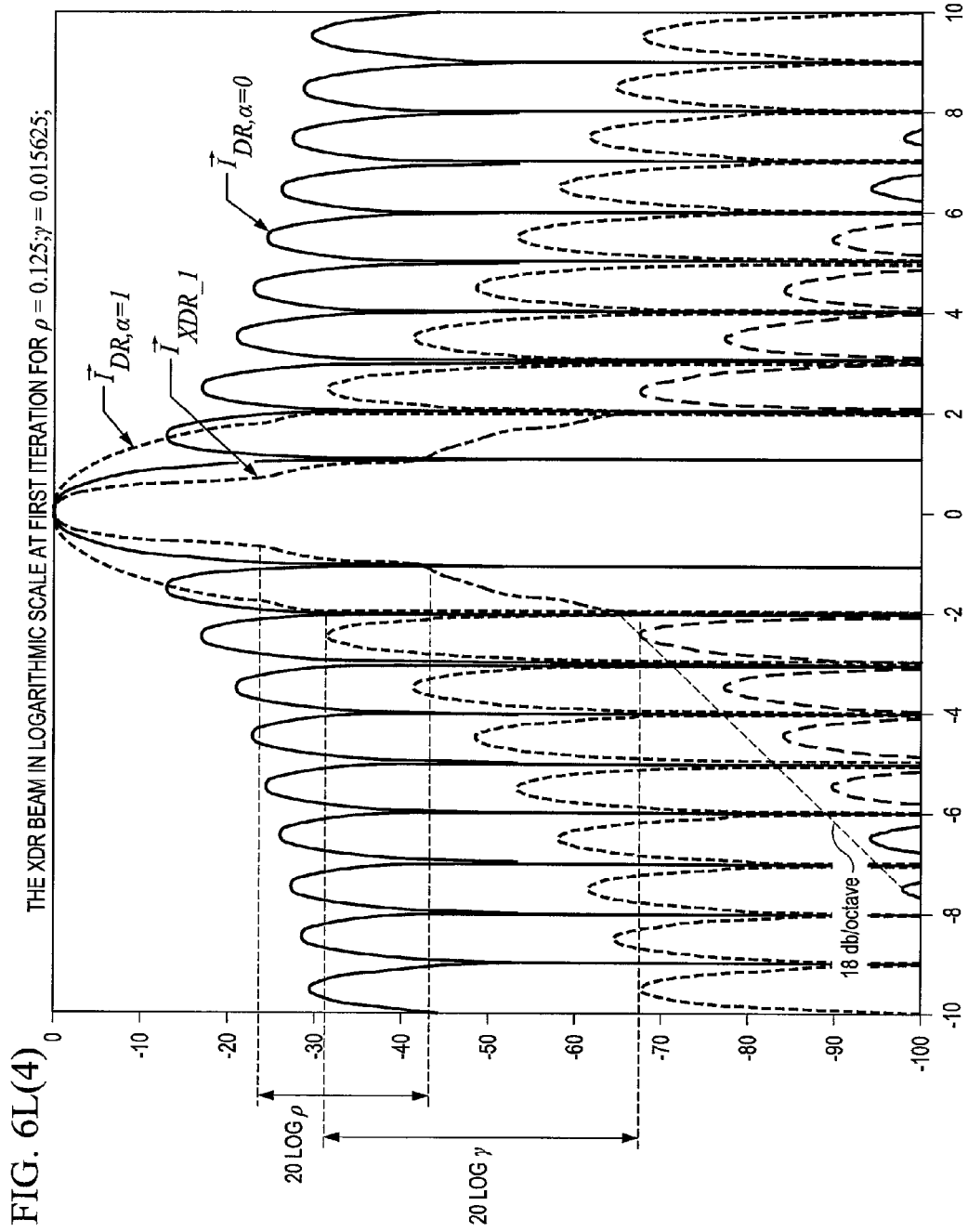
FIG. 6L(4)

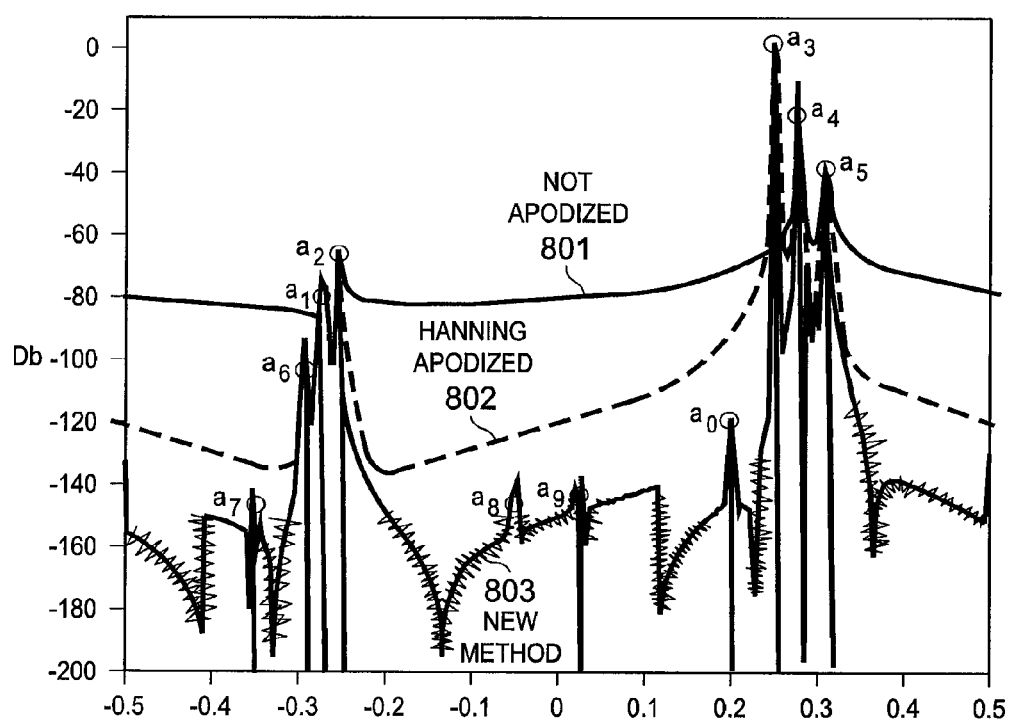

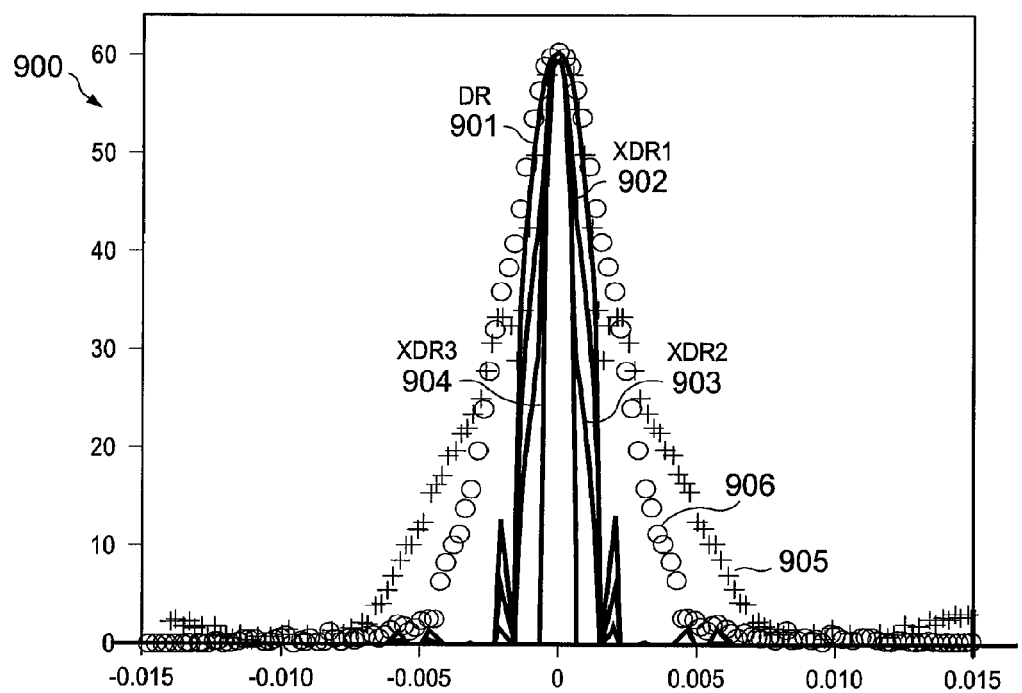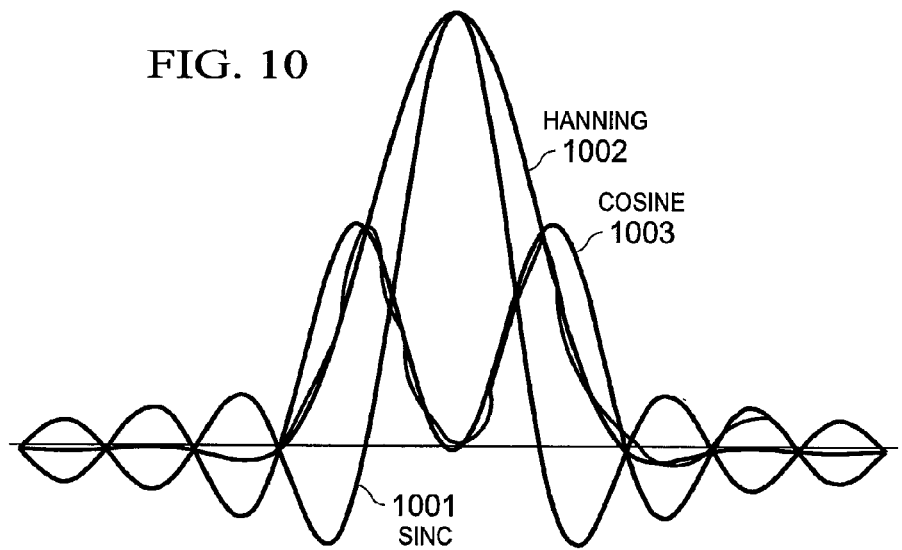

K=2 FOR MAINLOBE SPLITTING
$\rho = 0.0625; \gamma = 0.125$ $\vec{I}_I$ FROM THE HANNING BEAM
$\vec{I}_X$ FROM XDR BEAM
$\vec{I}_u$ FROM SINC BEAM $\vec{I}_I$ FROM THE HANNING BEAM
$\vec{I}_u$ FROM SINC BEAM
$\vec{I}_X$ FROM XDR BEAM

$\vec{M}$ IS A COMPONENT SIGNAL CREATED ACCORDING FIGURE 6 R WHERE
$\vec{M} = \varphi(\vec{I}_{DR,\alpha=1}) \text{ MIN } (|\vec{I}_{DR,\alpha=1}|,|\vec{I}_C|)$

FIG. 15A

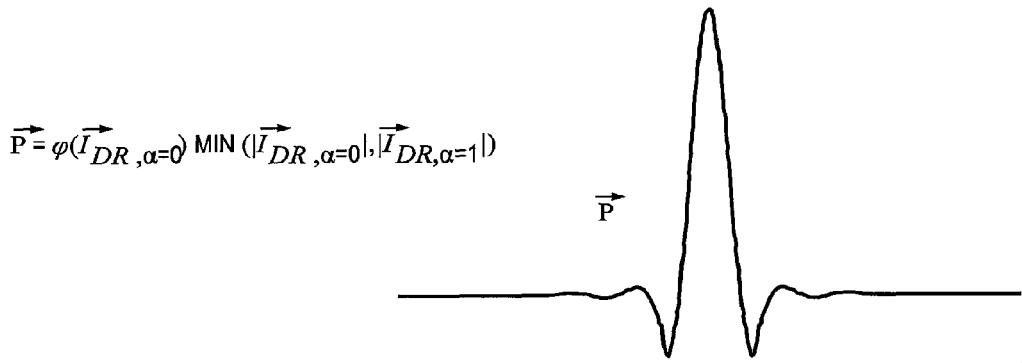

$\vec{P} = \varphi(\vec{I}_{DR,\alpha=0}) \text{ MIN } (|\vec{I}_{DR,\alpha=0}|,|\vec{I}_{DR,\alpha=1}|)$

FIG. 15B

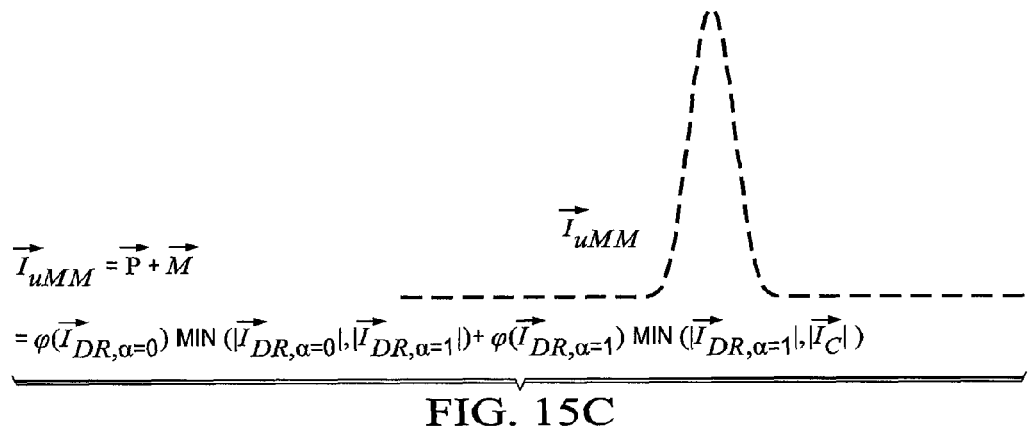

$\vec{I}_{uMM} = \vec{P} + \vec{M}$ $= \varphi(\vec{I}_{DR,\alpha=0}) \text{ MIN } (|\vec{I}_{DR,\alpha=0}|,|\vec{I}_{DR,\alpha=1}|) + \varphi(\vec{I}_{DR,\alpha=1}) \text{ MIN } (|\vec{I}_{DR,\alpha=1}|,|\vec{I}_C|)$

FIG. 15C

SYSTEMS AND METHODS FOR BEAM ENHANCEMENT

CROSS-REFERENCE TO RELATED APPLICATIONS

This application is a division of U.S. patent application Ser. No. 13/508,966, entitled "SYSTEMS AND METHODS FOR BEAM ENCHANCEMENT", filed May 9, 2012, now U.S. Pat. No. 8,876,719, which is a national stage application of International Patent Application PCT/US2010/56000, entitled "SYSTEM AND METHODS FOR BEAM ENHANCEMENT", filed Nov. 9, 2010, which claims the benefit of U.S. Provisional Patent Application No. 61/259,346, entitled "SYSTEMS AND METHODS FOR SCAN BEAM SIDELOBE REDUCTION WHILE REDUCING THE MAINLOBE USING DYNAMIC RESOLUTION", filed on Nov. 9, 2009; and U.S. Provisional Patent Application No. 61/259,938, entitled "SYSTEMS AND METHODS FOR SCAN BEAM SIDELOBE REDUCTION WHILE REDUCING THE MAINLOBE USING DYNAMIC RESOLUTION", filed on Nov. 10, 2009; the full disclosure of which are incorporated herein by reference.

TECHNICAL FIELD

This disclosure relates to beamforming and more particularly to systems and methods for beam enhancement, such as through sidelobe reduction and/or mainlobe shaping.

BACKGROUND OF THE INVENTION

In sonographic systems, acoustic signals are transmitted by a scanhead into a body or other subject and reflected signals are received by the scanhead for image processing. The reflected signals are used by the sonographic system to form images of the structure of the body matter (e.g., a patient's tissue) or other subject of interest. A scanhead used in such sonographic imaging is typically a hand held enclosure which contains one or more independent transducers and possibly other electronics.

The transducers of a sonographic system scanhead convert electrical energy to mechanical (acoustic) energy radiating away from its surface when transmitting and mechanical (acoustic) energy impinging upon its surface to electrical energy when receiving. An individual portion of transduction material is called an element which is often manufactured as a particular geometric shape such as a rectangle. Typically, these transducer elements are arranged in a regular pattern (an array) with their centers arranged as a line to form a linear array or phased array, along an arc to form a curved array, or in a grid to form a 2D array. Usually this regular pattern of transducer elements has a repeated spacing as measured from element center to element center which is called the pitch. In sonographic imaging operations transducer elements are generally used in groups. The total extant of such a group of transducer elements in a dimension is the aperture in that dimension. For example, for a linear array, one dimension is the height of the transducer element while the other dimension is the number of transducer elements used times the pitch.

An ultrasonic beam may be formed, whether in transmit or receive operation, through appropriate use of the foregoing groups of transducer elements. For example, a receive beam is formed by adjusting one or more attributes of the transducer element signals (e.g., delaying and/or weighting to provide transducer element beamforming signals corresponding to transducer elements of the selected aperture) and summing these transducer element beamforming signals to provide a beamformed signal having a maximum signal response corresponding to a particular point (the particular point being a "focal point"). The foregoing transducer element signal attributes are referred to herein as beamforming parameters. Such beamforming parameters are typically utilized to form beams to reject clutter (e.g., undesired reflected signals etc.) received from undesired areas (e.g., directions other than a desired "look direction").

In particular, the delays are applied to the transducer element signals from the group of transducer elements such that if a narrow pulse were emitted from the focal point, the signals having been thus delayed would arrive at a summing device at the same time and therefore would result in the largest value. This same narrow pulse coming from any other point than the focal point would not arrive simultaneously at the summer and therefore would not sum to be as large a signal. A beam having a particular shape (e.g., width, length, direction, etc.) may be formed through use of appropriate beamforming parameters. For example, a mainlobe that is "pointed" in a desired "look" direction may be formed.

Independent from the application of delays to create beams, an aperture may be apodized. Apodization is the process of applying potentially unique gain values (weighting) to the transducer element signals before they are summed. Particular apodization functions may be applied to apertures for generating beams having desired attributes, such as reduced sidelobes and thus to further reject clutter. There are many standard weighting functions that can be applied to an aperture, but there are three that are particularly exemplary. These are uniform weighting (also known as rectangular, box car, sinc, or unapodized), Hanning (also known as Hann) weighting, and cosine weighting. Hanning weighting $(1+\cos(x))$ and cosine weighting $(\cos(x))$ are related to one another in that Hanning weighting is a raised cosine function. Other mathematical functions which may be used for aperture apodization in ultrasound imaging systems are Hamming, Blackman-Harris, or other application specific window functions.

The beam formed by uniformly weighted aperture is termed a Sinc beam, the beam formed by Hanning weighted aperture is termed Hanning beam, and the beam formed by cosine function weighted aperture is termed cosine apodized beam. An object is scanned by sequentially shifting an ultrasound beam (e.g., Sinc beam, flaming beam, or Cosine apodized beam) to form an image. Depending upon the implementation, an ultrasound image can be formed either by Sinc beam or Hanning beam or beams of other types.

When beamforming parameters (e.g., delays) are continuously adjusted so that the focal point moves along a particular direction, a dynamically focused beam is created. In providing beam scanning for sonographic imaging, these dynamic beams are usually formed so that the focal point follows a straight line in Cartesian space for linear arrays or along a single angle from an apex in either phased or curved arrays. For example, by sequentially adjusting the beamforming parameters of the transducer element signals a series of beams may be formed to scan a volume of interest (e.g., a particular area or depth within a patient may be scanned). Information from a plurality of such scanned beams can be aggregated to generate an image of the scanned volume of interest (e.g., an ultrasound image of a sub-dermal portion of a patient). For example, in ultrasound B-mode operation, an image is generated from multiple lines of echo data received from a plurality of ultrasound beams of different look directions (e.g., beams scanned in different look directions). Such image generation from scanned beams is referred to herein as scanned volume imaging.

It is known that the monochromatic signal acquired by the Hanning beam is mathematically equal to summing the signal acquired from the Sinc beam with the average of signals acquired from two spatially shifted neighboring Sinc beams, provided that these beams are spaced according to Nyquist theorem. That is, the first null of the left Sinc beam and the first null of the right Sinc beam must be aligned with the peak of the center Sinc beam. Based on these properties, by processing signals acquired from three adjacent Nyquist spaced Sinc beams, a technique has been proposed to improve the performance in radar applications. However, in ultrasound imaging, the line density is selected according to multiple system parameters for optimal image quality, thus setting the sampling spacing from beam to beam or scan line to scan line according to Nyquist criterion generally cannot be satisfied. Furthermore, in ultrasound imaging dynamic beamforming, as may be used in providing the aforementioned scanned sample beams, is usually implemented in conjunction with a variable aperture. In other words, different aperture sizes are used for forming beams at different depths. Thus, the clutter reduction technique based on processing Sinc beam, such as may be implemented for radar, often cannot be adopted for use in ultrasound scanned volume imaging.

FIG. 1A illustrates the aforementioned scanned volume imaging. Specifically, transducer 11, having transducer elements E1 to EN, shown in FIG. 1A may be operated to provide such scanned volume imaging. In operation, transducer element signals of transducer elements E1 to EN are processed to form receive beams directed to particular areas within volume being imaged 15. Such beams may be formed to collect information regarding objects (also referred to as objects of interest) within volume being imaged 15, such as object 12 (e.g., fluid filled region) and object 13 (e.g., tissue structure) present below surface 16 (e.g., skin surface).

It should be appreciated that the higher the signal to clutter ratio in the signals (e.g., beamformed signals) used in scanned volume imaging, the higher the contrast resolution (e.g., better tissue differentiation) will be in the generated image. One source of signal clutter are the aforementioned sidelobes which typically accompany the mainlobes of the generated beams. The presence of undesired sidelobes in association with desired mainlobes can be seen from the illustration of FIG. 1A. Specifically, the mainlobes illustrated in FIG. 1A each have sidelobes associated therewith (e.g., sidelobes SL5 associated with mainlobe ML5, the combination of which are shown in a dashed line portion to help in distinguishing these lobes from the composite representation). The number and level of the sidelobes and their structure define how much of the off-axis undesired echoes are integrated into the resulting beamformed signal, thus cluttering the desired echoes of the object of interest. The ability to reduce the sidelobes improves the contrast resolution or the differentiability of objects of interest, such as tissues in an image.

Another source of image degradation is the width of the mainlobes used to collect image information. For example, the width of the mainlobe defines how an object within a volume being imaged is spread by the beam. Thus, the width of the mainlobe typically relates to the detailed resolution of an image. Accordingly, it is often desirable that the beams formed for the aforementioned scanning have a narrow focus so that objects of interest in the generated images can be well defined.

From the above it can be appreciated that the width of the mainlobe, the level of the sidelobes, and the structure of the sidelobes (e.g., how fast the sidelobes roll off from the mainlobe) have great significance to image quality. For example, higher resolution images can be achieved with very well-defined beams.

Signal processing for image generation using transducer 11 of FIG. 1A may include forming beams using a selected aperture (e.g., a selected group of transducer elements, such as transducer elements E11-E15) by appropriately implementing beamforming parameters (e.g., delays and/or weights) for the transducer element signals received by the transducer elements of the selected aperture. For example, delays of the beamforming parameters may be selected to provide mainlobes ML11-ML15 having desired focal points (e.g., applying appropriate delays to provide beams to scan a particular depth of volume being imaged 15). Additionally, the beamforming process may involve applying appropriate weights (apodization process) to the signals received from the transducer elements of the selected aperture, such as to reduce sidelobes associated with the mainlobes. Thus, the beam forming parameters utilized in generating beams may comprise complex values such that the signal received from transducer elements may be modified both in magnitude and phase.

Although generally reducing the sidelobes of the beam, use of the aperture apodization process spreads the mainlobe. Undesirable results associated with the use of the foregoing typical beamforming using an apodization processes are illustrated by FIGS. 1B-1D. FIG. 1B shows tissue mimic phantom 150 (generally representing volume being imaged 15 shown in FIG. 1A) which is composed of fluid filled region A on the left (such as may correspond to a portion of the volume being imaged of FIG. 1A comprising object 12) and tissue region B on the right (such as may correspond to a portion of the volume being imaged of FIG. 1A comprising object 13). Tissue region B is assumed to comprise a cluster of point scatterers (e.g., point scatters 14) of equal scattering cross-sections. An image is formed when a volume being imaged, represented here by tissue mimic phantom 150, is insonified with a sequence of ultrasound beams formed by the linear array of elements E1-EN. Since little scattering intensity will be received from fluid filled region A, the resulting image (in an ideal situation) would hold no gray scale displayed for fluid filled region A, whereas tissue region B would display a distribution of dots with similar intensity to those shown in the mimic phantom.

As discussed above, in conventional ultrasound imaging systems, the aperture of an array is either apodized with a deterministic mathematical function to partially suppress the sidelobes (thereby widening the mainlobe) for improvement of image contrast or not apodized to maintain a narrower mainlobe thereby yielding smaller imaging dot size with increased clutter. Each results in a degradation of image quality and will display a distorted image.

FIG. 1C shows the two different beam configurations discussed above to illustrate the problem. Beam $B_U$ is an unapodized beam (e.g., a Sinc beam formed using a uniform weighting function to define beamforming weighting distribution) providing a more narrow mainlobe having sidelobes with relatively high levels. Beam $B_H$ is an apodized beam (e.g., a Hanning beam formed using a raised-cosine weighting function to define beamforming weighting distribution) providing a more wide (spread) mainlobe having sidelobes with relatively low levels. The magnitude of the beams illustrated in FIG. 1C are logarithmically compressed and the sidelobes are scalloped and gradually roll off.

It is assumed that beams $B_U$ and $B_H$ are used to image a same area, specifically a portion of tissue region B of tissue mimic phantom 150 of FIG. 1B. Beam $B_U$ generates object of interest representation 101 (as may be used in aggregating an image generated by scanning a plurality of beams $B_U$ in different look directions within the area represented by tissue mimic phantom 150) resulting from reflected signals (e.g., reflected by point scatters 14) received by the mainlobe. Beam $B_U$ further generates artifacts 101-1 to 101-8 (also as may be aggregated into a generated image as undesired clutter) resulting from reflected signals received by the sidelobes. Likewise, beam $B_H$ generates object of interest representation 100 (as may be used in aggregating an image generated by scanning a plurality of beams $B_H$ in different look directions within the area represented by tissue mimic phantom 150) resulting from reflected signals (e.g., reflected by point scatters 14) received by the mainlobe. Beam $B_H$ further generates artifacts 100-1 to 100-4 (also as may be aggregated into a generated image as undesired clutter) resulting from reflected signals received by the sidelobes. As can be seen in FIG. 1C, although the same area of an object was imaged, object of interest representation 100 as provided by beam $B_H$ is spread compared to object of interest representation 101 provided by beam $B_U$. Also as can be seen in FIG. 1C, more (albeit smaller) artifacts are generated by beam $B_U$ (artifacts 101-1 to 101-8) than artifacts generated by beam $B_H$ (artifacts 100-1 to 100-4).

A sonographic image may be generated by scanning a plurality of either beam $B_U$ or beam $B_H$ to insonify a volume being imaged. For example, the representations created by scanning a respective one of beams $B_U$ and $B_H$ throughout the area represented by tissue mimic phantom 150 may be aggregated to form an image of an object of interested. However, as can be appreciated from the illustration of FIG. 1C, when using beam $B_U$ the object of interest in the generated image may be relatively sharp because the object of interest representations (e.g., object of interest representation 101) are relatively small but the number of artifacts (e.g., artifacts 101-1 through 101-8) is high as a result of the more prominent sidelobes. The artifacts associated with the use of beam $B_U$ also extend a long distance from corresponding ones of object of interest representations, further degrading the generated image. Also as can be appreciated from the illustration of FIG. 1C, when using beam $B_H$ the object of interest in the generated image is less sharp because the object of interest representations (e.g., object of interest representation 100) are relatively large but the number of associated artifacts (e.g., artifact 100-1 through 100-n) is low as a result of the less prominent sidelobes. Moreover, the artifacts associated with the use of beam $B_H$ extend a shorter distance from the object of interest representation. Each of the foregoing beam forming techniques, therefore, results in generated images which often are of a lower quality than desired. As can be appreciated from the foregoing, achieving a well-defined beam without significant sidelobes for providing quality imaging has proven illusive.

BRIEF SUMMARY OF THE INVENTION

The present invention is directed to systems and methods which provide beam sidelobe reduction such as through use of dynamic resolution (DR) beam synthesizing techniques. Dynamic resolution beamforming techniques of embodiments of the invention provide enhanced beam mainlobe attributes in addition to providing beam sidelobe reduction by synthesizing a DR beam from a plurality of beams (referred to as sample beams).

Embodiments implement a DR beam synthesizing technique by acquiring a plurality of beamformed signals from sample beams for each scanned area of a volume being imaged. For example, both a first sample beam (e.g., an unapodized beam such as may be formed using a sine function to define beamforming weighting distribution) and a second sample beam (e.g., an apodized beam such as may be formed using a cosine function to define beamforming weighting distribution) are formed for each scanned area (e.g., each look direction) of a volume being imaged (e.g., tissue areas). The resulting sample beam signals (e.g., the beamformed signal using an unapodized function and the beamformed signal using an apodized function) are utilized to synthesize a beamformed signal corresponding to that of a signal from a high-resolution, low side-lobe beam through operation of DR beamforming techniques herein. According to preferred embodiments of the invention, sample beams may be weighted and combined in a DR beamforming technique to yield a minimized total power. The resulting DR beam preferably has reduced sidelobes with relatively little or no spread of the mainlobe.

In an improved dynamic resolution (IDR) beam synthesizing technique of embodiments, a DR beam is segmented for synthesizing an IDR beam having desired attributes. For example, a DR beam may be segmented into its mainlobe component and its sidelobe component, such as using a sample beam (e.g., the aforementioned second sample beam). These beam components are preferably independently manipulated or otherwise processed, such as to alter one or more attributes thereof (e.g., applying different weighting). IDR beam synthesizing techniques herein operate to synthesize IDR beams from the manipulated segmented beam components (e.g., greater weighting for the mainlobe component and lesser weighting for the sidelobe component) by recombining these beam components to synthesize an IDR beam.

A sharpening function may be applied to DR/IDR beams, if desired, to provide an even further enhanced beam. DR/IDR beams having a sharpening function applied thereto are referred to herein as enhanced dynamic resolution (XDR) beams. XDR beams, having had a sharpening function applied, provide a mainlobe that is narrower than the corresponding DR/IDR beam. Additionally, the sidelobes of such XDR beams can be further suppressed at a level to achieve better image quality.

Although embodiments of IDR and XDR beam processing may utilize beam synthesis of DR beam processing as discussed above, the use of DR beam synthesis is not a limitation of the application of the concepts herein. For example, embodiments of IDR and/or XDR beam sharpening processing may be applied with respect to the Sinc beam and the cosine apodized beam without using the DR beam (e.g., minimum power beam by processing Sinc and cosine apodized beams).

One feature of embodiments of the invention is to optimize the focus performance of every beamformed sample in the sample space of a generated image. Another feature of embodiments of the invention is minimizing spectral leakage and improving spectral resolution in pulse wave ("PW"), continuous wave ("CW"), and color flow processing with or without coded excitation and code patterns. A still further feature of the invention is that embodiments may readily be adapted for use in many types of systems, such as multi-line beamforming, synthetic aperture beamforming and high frame rate beamforming.

Embodiments of the concepts herein may be applied to ultrasound imaging to provide beam sidelobe reduction. However, the concepts herein are not limited to applicability with respect to ultrasound imaging. Embodiments may be applied with respect to visible light, infrared, radio frequency, and other imaging techniques.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which:

FIG. 8 shows one example of the concepts of this invention applied to one dimensional processing;

FIG. 9 shows various beams processed using different sets of parameters according to embodiments of the invention;

FIG. 10 shows the relationships between various beams processed according to embodiments of the invention;

FIGS. 15A-15G show generation of new component signals with different beam properties according to an embodiment of the invention.

DETAILED DESCRIPTION OF THE INVENTION

Figure 2A:
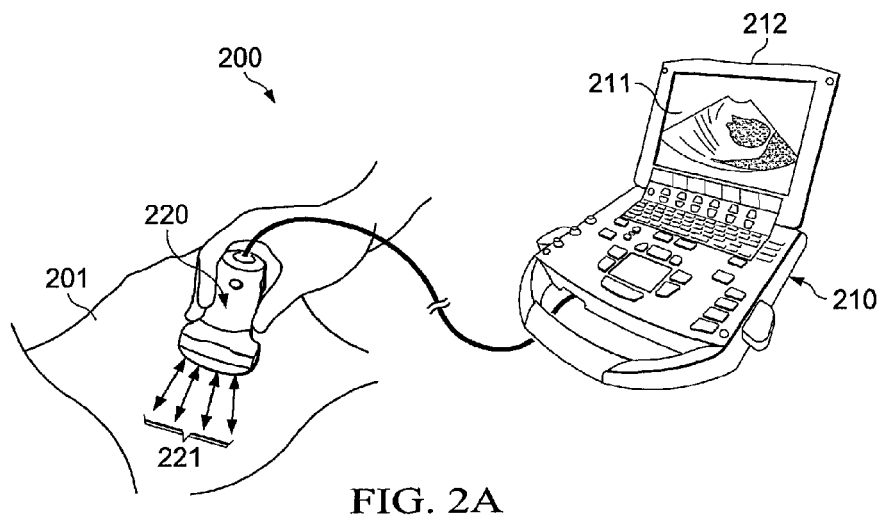
FIGS. 2A and 2B show a system adapted to provide dynamic resolution, improved dynamic resolution, and/or enhanced dynamic resolution processing according to embodiments of the invention.

FIG. 2A shows an embodiment of an ultrasound imaging system adapted according to an embodiment of the invention. It should be appreciated that the exemplary embodiment is described with reference to ultrasound imaging in order to provide a more concrete example to aid in understanding the concepts herein. However, the concepts of the present invention are not limited to application with respect to ultrasound imaging. Thus, the concepts herein may be applied with respect to a number of technologies wherein reflection of transmitted signals are used, such as visible light, infrared, and radio frequency imaging techniques.

Ultrasound imaging system 200 is shown comprising system unit 210 in communication with scanhead 220. System unit 210 of embodiments comprises a processor-based system operable to control a transducer (e.g., transducer 11 shown in FIG. 1A) of scanhead 220 to transmit and receive ultrasound signals using scanned beams 221 to provide scanned volume imaging. Accordingly the processor-based system of system unit 210 of embodiments processes received ultrasound signals to generate image 211, displayed on display 212, representing a portion of volume being imaged 201. Detail with respect to imaging systems which may be adapted according to the concepts of the present invention is provided in co-pending and commonly assigned U.S. patent application Ser. No. 12/467,899 entitled "Modular Apparatus for Diagnostic Ultrasound," the disclosure of which is hereby incorporated herein by reference.

Figure 1A:
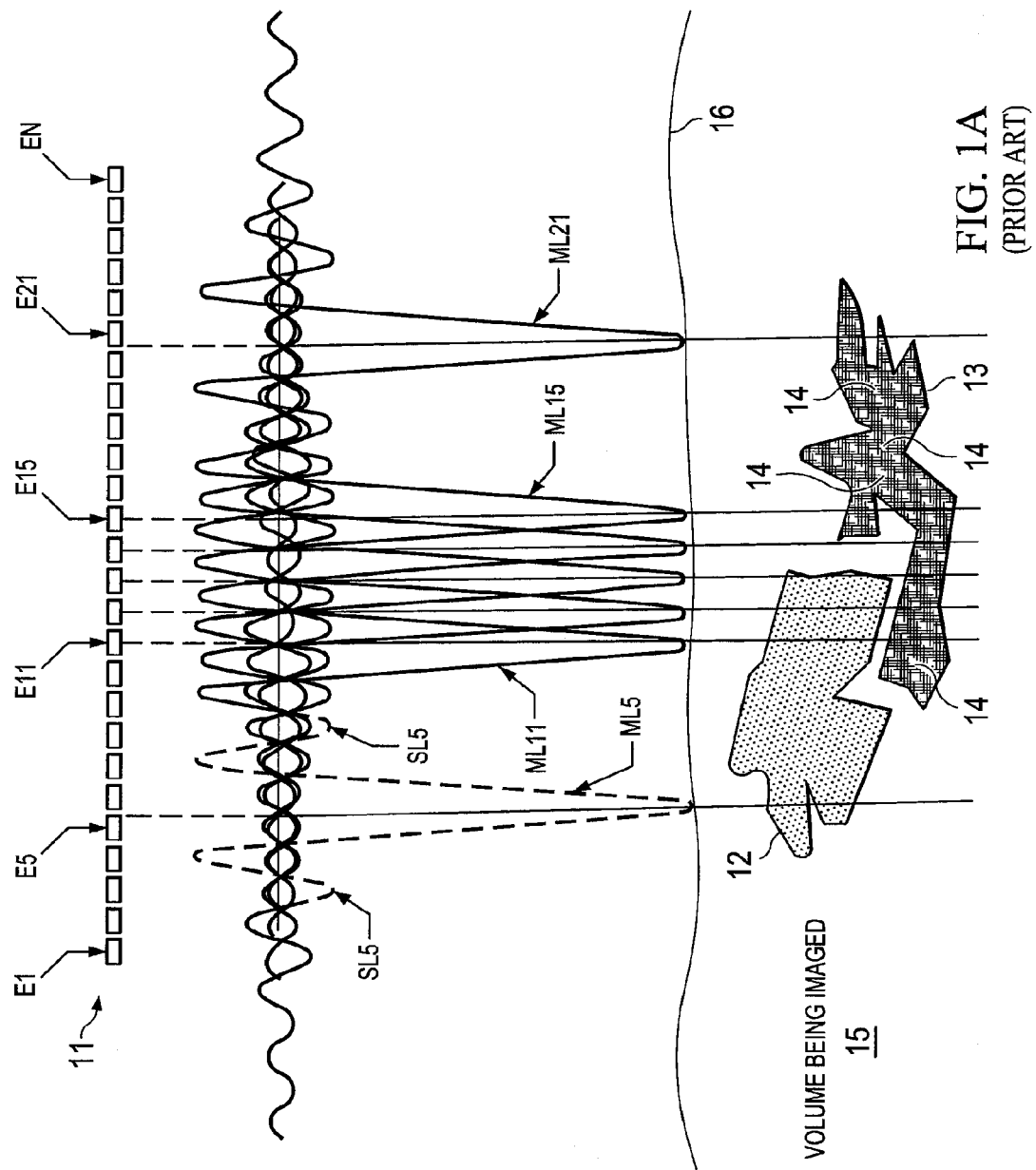
FIGS. 1A-1C illustrate the need for sidelobe reduction and the problems inherent when attempting to reduce sidelobes in a conventional fashion.
Figure 1B:
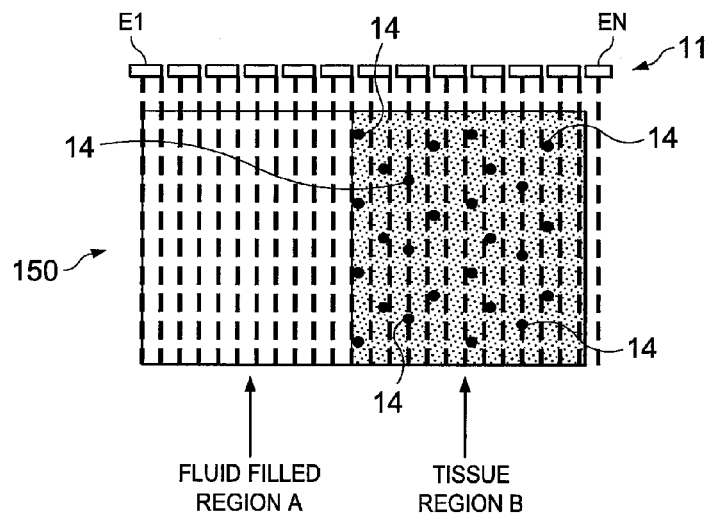
Figure 2B:
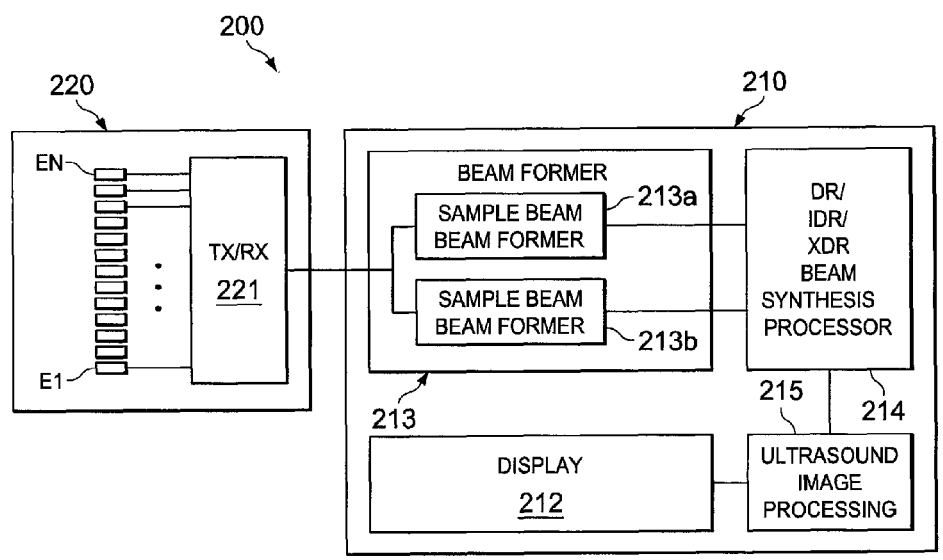

Further detail with respect to an embodiment of ultrasound imaging system 200 is shown in the high level functional block diagram of FIG. 2B. As shown in FIG. 2B, a transducer of scanhead 220 may comprise an array of ultrasound elements (e.g., transducer 11 of FIG. 1A with transducer elements E1-EN) in communication with transmit/receive circuitry 221 (such as may comprise amplifiers, buffers, multiplexers, etc.) and operable to controllably transmit and receive ultrasound signals.

System unit 210 of FIG. 2B comprises beamformer 213, DR/IDR/XDR beam synthesis processor 214, ultrasound image processing circuitry 215, and display 212. Beamformer 213 operates to provide beamforming with respect to signals provided to/from transducer 11. DR/IDR/XDR beam synthesis processor 214 operates to provide dynamic resolution beam synthesis processing as described herein. Ultrasound image processing circuitry 215 operates to form ultrasound images (e.g., B-mode, M-mode, Doppler mode, 3-D, 4-D, etc.) using dynamic resolution (e.g., DR, IDR, and/or XDR) beam signals synthesized by DR/IDR/XDR beam synthesis processor 214, such as for display upon display 212.

It should be appreciated that additional and/or alternative functional blocks to those illustrated in FIG. 2B may be utilized according to embodiments of the invention. For example, one or more analog to digital converters (ADC) and/or digital to analog converters (DAC) may be utilized, such as where digital beam forming or digital signal processing is implemented by ultrasound imaging system 200. Moreover, the functional blocks may be distributed differently than shown in FIG. 2A. For example, beamformer 213 may be disposed in scanhead 220, such as where a "thin wire" link is desired between scanhead 220 and system unit 210.

It is possible to optimize the signal to clutter ratio in the signal associated with interrogated tissue locations based on an adaptive beamforming process, as may be implemented by beamformer 213. In an adaptive beamforming process, a series of matrix operations of the magnitude and the phases of the signals from all transducer elements (or some selected subset of the transducer elements) is used for every sample location. The dimension of the matrix typically is proportional to the dimension of the array aperture. When the aperture is large as in conventional ultrasound imaging systems, for example, 32, 64, or 128, the processing power required for implementation is very high and may be prohibitive for some system applications.

Sample beam beamformers 213a and 213b of beamformer 213 utilize a delay-and-sum beamforming process for generating beamformed signals for interrogated tissue locations within a scanned volume according to embodiments. Delay-and-sum beamforming is done by integrating the signal received from transducer elements (all or some selected subset of the transducer elements) after the arrival time differences among transducer elements are compensated. The output from the beamformer is a beamformed signal that changes its magnitude and phase depending upon distribution of scattering cross sections of tissue.

In operation according to an embodiment, a first set of beamforming parameters (e.g., a first set of delays and/or weights) provide the first sample beam simultaneously with a second set of beamforming parameters (e.g., a second set of delays and/or weights) providing the second sample beam. For example, sample beam beamformer 213a may implement a first set of beamforming parameters for forming a first sample beam (e.g., an unapodized beam) while sample beam beamformer 213b implements a second set of beamforming parameters for forming a second or auxiliary sample beam (e.g., an apodized beam). Accordingly, sample beam beamformers 213a and 213b simultaneously provide two different beamformed signals for dynamic resolution processing according to embodiments of the invention.

From the foregoing, it should be appreciated that in a beamformed signal, signals from a plurality of transducer element (all or some selected subset of transducer elements) are integrated into a single, beamformed signal. Thus the phase and the magnitude of the signal (e.g., echo signal) received at the individual transducer elements is lost. It is therefore a technical challenge to improve the beamformed signal post beamforming. However, using the DR, IDR, and/or XDR beam synthesis concepts herein, it is possible to improve the beam performance post beamforming.

Embodiments of ultrasound imaging system 200 implement dynamic resolution (DR) beam synthesis, improved dynamic resolution (IDR) beam synthesis, and/or extended dynamic resolution (XDR) beam synthesis techniques described herein. For example, a DR beam synthesis technique may be implemented by DR/IDR/XDR beam synthesis processor 214 of ultrasound imaging system 200 acquiring a plurality of beamformed signals provided by sample beam beamformers 213a and 213b of beamformer 213 for each scanned area of an object (e.g., tissue) being imaged to synthesize a DR beam. The signal of a synthesized DR beam may be further processed by DR/IDR/XDR beam synthesis processor 214 of ultrasound imaging system 200, such as using segmentation techniques described herein, to provide IDR and/or XDR beam synthesis.

A DR beam synthesis technique according to embodiments of the invention simultaneously acquires two beamformed signals from an interrogated tissue location. For example, both a first sample beam (e.g., beam $B_U$ of FIG. 3A) and a second or auxiliary sample beam (e.g., beam A of FIG. 3A) are formed using beamformer 213 for every sample point in each scanned area (e.g., each look direction) of volume being imaged 201. One way to minimize the sidelobes in a synthesized DR beam (e.g., beam $B_O$ of FIG. 3B) is by forming such sample beams having phase, shape, and magnitude that minimizes the sidelobes when the sample beams are combined to synthesize the DR beam. Accordingly, as can be appreciated from the illustration of FIG. 3A, the sample beams of embodiments are adapted to provide peaks and nulls which cooperate to synthesize a DR beam having desired attributes when these sample beams are combined. That is, the sidelobes associated with a first sample beam $B_u(\theta)$ may be reduced using a second or auxiliary sample beam $A(\theta)$ to result in a better quality DR beam $B_o(\theta)$.

Embodiments of a DR beam synthesis technique of the present invention for minimizing sidelobes may be implemented with a first sample beam formed with no apodization and a second sample beam, or auxiliary sample beam, formed by apodizing the aperture using a cosine function (e.g., cos ($\theta$)). For example, an unapodized beam pattern (beam $B_U$ of FIG. 3A) from an array can be described by a sine function sinc ($\theta$). The function sinc ($\theta$) is oscillatory with zero crossing at $\theta = \pm n\pi$ or sine ($\pm \pi$)=0 whereas sinc (0)=1. If a beam pattern from an array is apodized using the cosine function (e.g., beam A of FIG. 3A), the cosine apodized beam is symmetrically split into two geometrically shifted component Sinc beams whose two peaks are aligned with the first sidelobe of the un-apodized beam, with a null placed at the origin A(0)=0; A is the second sample beam or the cosine apodized beam. Thus, the cosine apodized beam can be used as an auxiliary sample beam for sidelobe reduction when applied to an unapodized sample beam formed using a sine function. It should be appreciated that, although a Sinc beam and cosine apodized beam are referenced herein to demonstrate the DR beam synthesis process, other combinations of sample beams can be used to process signals for image reconstruction with improved image quality in accordance with the concepts of the present invention.

The sample beamformed signals resulting from the sample beams are utilized by DR/IDR/XDR beam synthesis processor 214 of FIG. 2B to synthesize a signal corresponding to a DR beam (e.g., $B_O$ of FIG. 3B) of the present invention. For example, using geometrical and/or morphological properties of the sample beams, signals from the sample beams are combined to synthesize a DR beam having desired characteristics. Where the sample beams provide geometrical and/or morphological properties which combine to cancel undesired attributes (e.g., sidelobes), DR beam synthesis of embodiments may operate to sum the sample beams (e.g., $B_O = B_U + \alpha A$). However, where the sample beams provide geometrical and/or morphological properties which combine to increase undesired attributes (e.g., sidelobes), DR beam synthesis of embodiments may operate to subtract the sample beams (e.g., $B_O = B_U - \alpha A$). Accordingly, it should be appreciated that the mathematical relationships provided herein with respect to the use of sample beams in synthesizing DR beams may implement a change in sign depending upon the combining/canceling characteristics of the particular sample beams utilized.

As will be better understood from the discussion which follows, a in the foregoing examples defines a fractional amount of signal received from the second sample beam which is used to cancel the undesired portions of the first sample beam. The parameter $\alpha$ is used according to embodiments to provide a balance between sidelobe mitigation and mainlobe spreading in DR beam synthesis. Accordingly, DR beams synthesized through operation of dynamic resolution beamforming techniques herein preferably have reduced sidelobes with relatively little or no spread of the mainlobe.

The following discussion is offered to aid in better understanding the DR beam synthesis process of embodiments of the invention. When first sample beam $B_u(\theta)$ is used to scan a volume being imaged, the resulting beamformed signal $I_u(\theta)$ received by scanning first sample beam $B_u(\theta)$ on the object $O(\theta)$ can be described as $I_u(\theta) = \int O(\phi-\theta) * B_u(\phi-\theta) d\phi$. Assume that first sample beam $B_u(\theta)$ can be decomposed into two components $B_{uM}(\theta)$ and $B_{uS}(\theta)$, where beam component $B_{uM}(\theta)$ is the desired beam component (e.g., mainlobe) and beam component $B_{uS}(\theta)$ is the undesired beam (e.g., sidelobes) and where $B_{uM}(\theta) = B_{uM}(\theta) + B_{uS}(\theta)$. Thus, $I_u(\theta) = \int O(\phi-\theta) * B_u(\phi-\theta) d\phi = I_{uM}(\theta) + I_{uS}(\theta)$.

Second sample beam $A(\theta)$ may be an auxiliary beam which "looks" or points in the same direction ($\theta$) as that of first sample beam $B_u(\theta)$. Assume that second sample beam $A(\theta)$ can also be decomposed into two components $A_M(\theta)$ and $A_S(\theta)$, where $A(\theta) = A_M(\theta) + A_S(\theta)$. Thus; $I_A(\theta) = \int O(\phi-\theta) * A(\phi-\theta) d\phi = I_{AM}(\theta) + I_{AS}(\theta)$. From the above, DR beam $B_o(\theta)$ can be formed according to $B_o(\theta) = B_u(\theta) + \alpha A(\theta) = B_{uM}(\theta) + \alpha A_M(\theta) + B_{uS}(\theta) + \alpha A_S(\theta)$. Thus the sidelobe signal $B_{uS}(\theta)$ can be reduced by determining $\alpha$ to minimize the difference of $\|B_{uS}(\theta) + \alpha A_S(\theta)\|^2$ or $$\min_a(\|B_{uS}(\theta) + \alpha A_S(\theta)\|^2).$$

This is effectively equivalent to $$\min_a(\|I_{uS}(\theta) + \alpha I_{AS}(\theta)\|^2).$$

In order not to degrade the mainlobe of the DR beam according to embodiments of the invention, it is desired that the beam signal component resulting from the mainlobe of the second or auxiliary sample beam $\alpha I_{AM}(\theta)$ be as small as possible. That is, a non-zero $\alpha I_{AM}(\theta)$ typically results in at least some spreading of the mainlobe of $B_{uM}(\theta)$ in synthesized DR beam $B_o(\theta)$. In order to not alter the look or pointing direction of sample beam $B_u(\theta)$ when combined with second sample beam $A(\theta)$, second sample beam $A(\theta)$ of embodiments comprises a null placed in correspondence with mainlobe $B_{uM}(\theta)$ of the first sample beam. In other words, if $A(\theta) = 0$, and $B_o(\theta) = B_{uM}(\theta)$ then when the clutter energy from sidelobes are minimized as a result of the cancellation process $B_u(\theta) + \alpha A(\theta)$, the look or pointing direction of $B_{uM}(\theta)$ will not be altered except the mainlobe may be slightly spread due to the process of $B_{uM}(\theta) + \alpha A_M(\theta)$.

The parameter alpha, $\alpha$, may be bounded by predetermined minimum and maximum values. For example, the parameter alpha of embodiments is preferably bounded between 0 and 1 to avoid errors resulting from data acquisition or other numerical processes. It should be appreciated that there may be situations wherein canceling the clutter signal from a sample beam (e.g., the foregoing Sinc beam) by using the signal from a second sample beam (e.g., the foregoing cosine apodized beam) is not practical. For example, when the clutter level is extraordinary high, or signal from an undesired direction is so high that higher performance sidelobe cancellation beam better than that readily achieved from the second sample beam may be desired. In such a situation, the value of the parameter $\alpha$ may be set to a predetermined maximum acceptable value (e.g., 1) according to embodiments of the invention.

Alpha being zero represents a situation that the sidelobe is low in the first sample beam (e.g., Sinc beam) and no signal is needed from the second or auxiliary sample beam (e.g., cosine apodized beam) for sidelobe cancellation in DR beam synthesis. In contrast, when alpha is equal to 1, signals received from the second or auxiliary sample beam (e.g., cosine apodized beam) attributed to the sidelobes are needed for cancellation of the sidelobes of the first sample beam (e.g., Sine beam) for DR beam synthesis. Accordingly, in the Sine beam/cosine apodized beam DR beam synthesis example of embodiments, where $\alpha = 0$ the synthesized DR beam is the Sine beam ($B_O = B_U + \alpha A = B_U + 0A = B_U$), whereas where $\alpha = 1$ the synthesized DR beam is a raised cosine or Hanning beam ($B_O = B_U + \alpha A = B_U + 1A$). Values of a between 0 and 1 provide a synthesized DR beam mainlobe varying in width between the mainlobe of the Sine beam and the mainlobe of the raised cosine apodized beam, with sidelobes reduced in accordance with a fractional amount of signal received from the cosine apodized beam sidelobes.

Optimization processes may be implemented to calculate the amount of signals needed from the second or auxiliary sample beam (e.g., cosine apodized beam) for the cancellation of undesired portions of the first sample beam (e.g., Sinc beam). Although different choices of objective function can be used in such an optimization process, in the DR beam synthesizing process of embodiments of the present invention. A criterion based on minimizing the power of the clutter signals in the beam may be chosen to compute the above described parameter $\alpha$. That is, the parameter $\alpha$ of embodiments of the present invention effectively defines the fractional amount of the second or auxiliary sample beam signal to be combined with the first sample beam signal to synthesize a DR beam, and thus an objective function for selecting the parameter $\alpha$ such that when the sample beams are combined the power of the clutter signals are minimized may be chosen according to embodiments.

In the DR beam synthesizing process of embodiments of the present invention, the parameter $\alpha$ may be changed dynamically from sample to sample (e.g., look direction to look direction). Since the parameter $\alpha$ of embodiments is chosen by minimizing the total clutter powers of the beam based on measurement from the sample beams (e.g., a Sinc beam and cosine apodized beam) in the sidelobe cancellation process, a good balance of detailed and contrast resolution may be achieved for every sample in a DR processed image. For example, at a sample location where the sidelobe is high, the parameter $\alpha$ may be set to a high or upper bound limit (e.g., 1 in the foregoing example), and the second sample beam is utilized to synthesize a DR beam having a low sidelobe, whose roll-off rate is fast. However, the width of the mainlobe of the synthesized DR beam may be spread by the influence of the second sample beam, and thus the image resolution may be poorer. At a sample location where little clutter is received from its neighbor, the parameter $\alpha$ may be set to a low or lower bound limit (e.g., 0 in the foregoing example), and the second sample beam essentially remains unutilized in synthesizing a DR beam. Since no apodization is utilized in such an embodiment, the mainlobe of the synthesized DR beam is narrow. Thus, the sidelobe cancellation parameter in an image varies from zero to one in the foregoing example. As a result, the DR beam synthesizing process effectively makes best tradeoff possible from detailed and contrast resolution in an image.

Figure 3A:
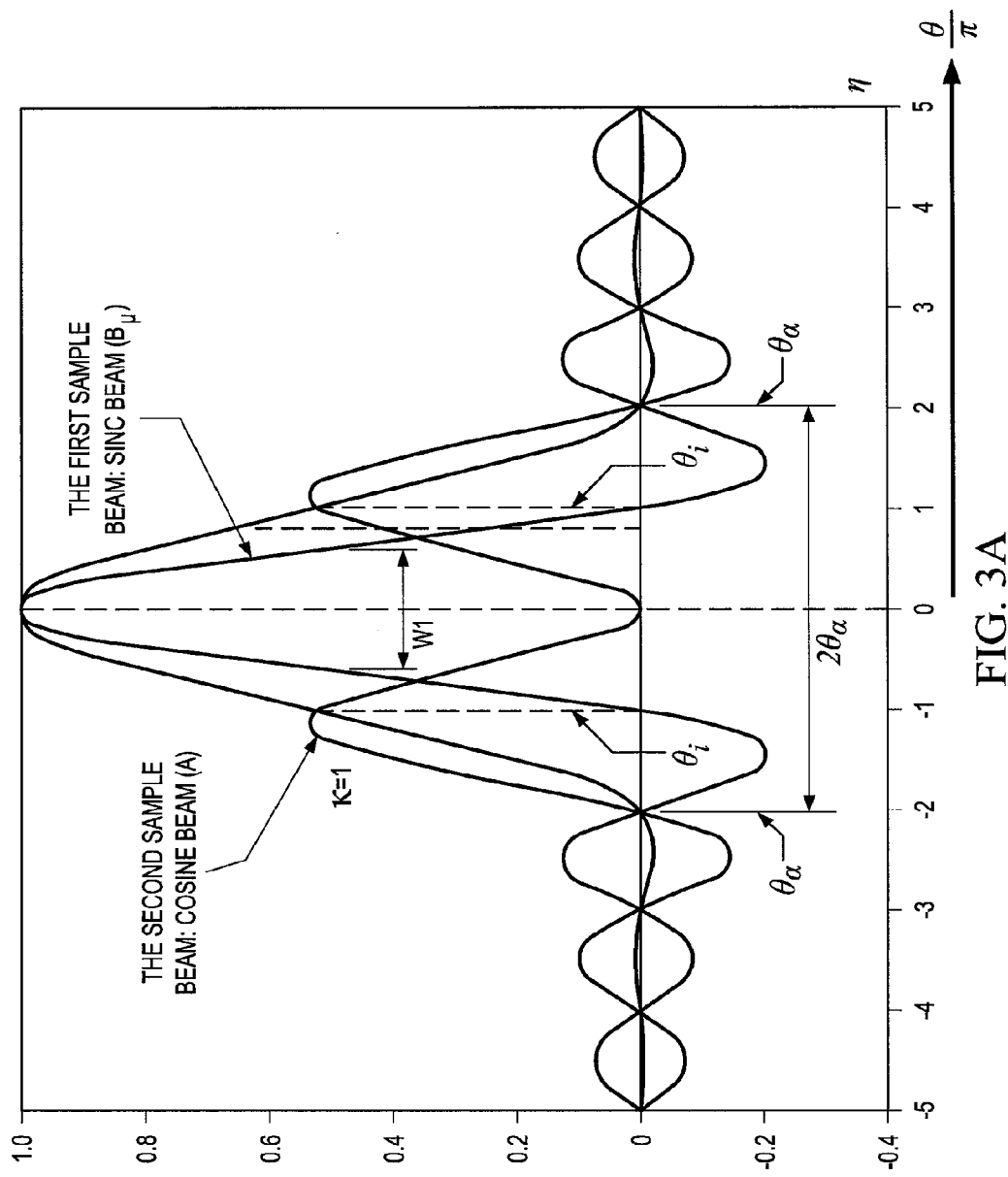
FIG. 3A shows examples of a first sample beam and a second or auxiliary sample beam as may be used by a dynamic resolution beam synthesis technique according to embodiments of the invention.
Figure 3B:
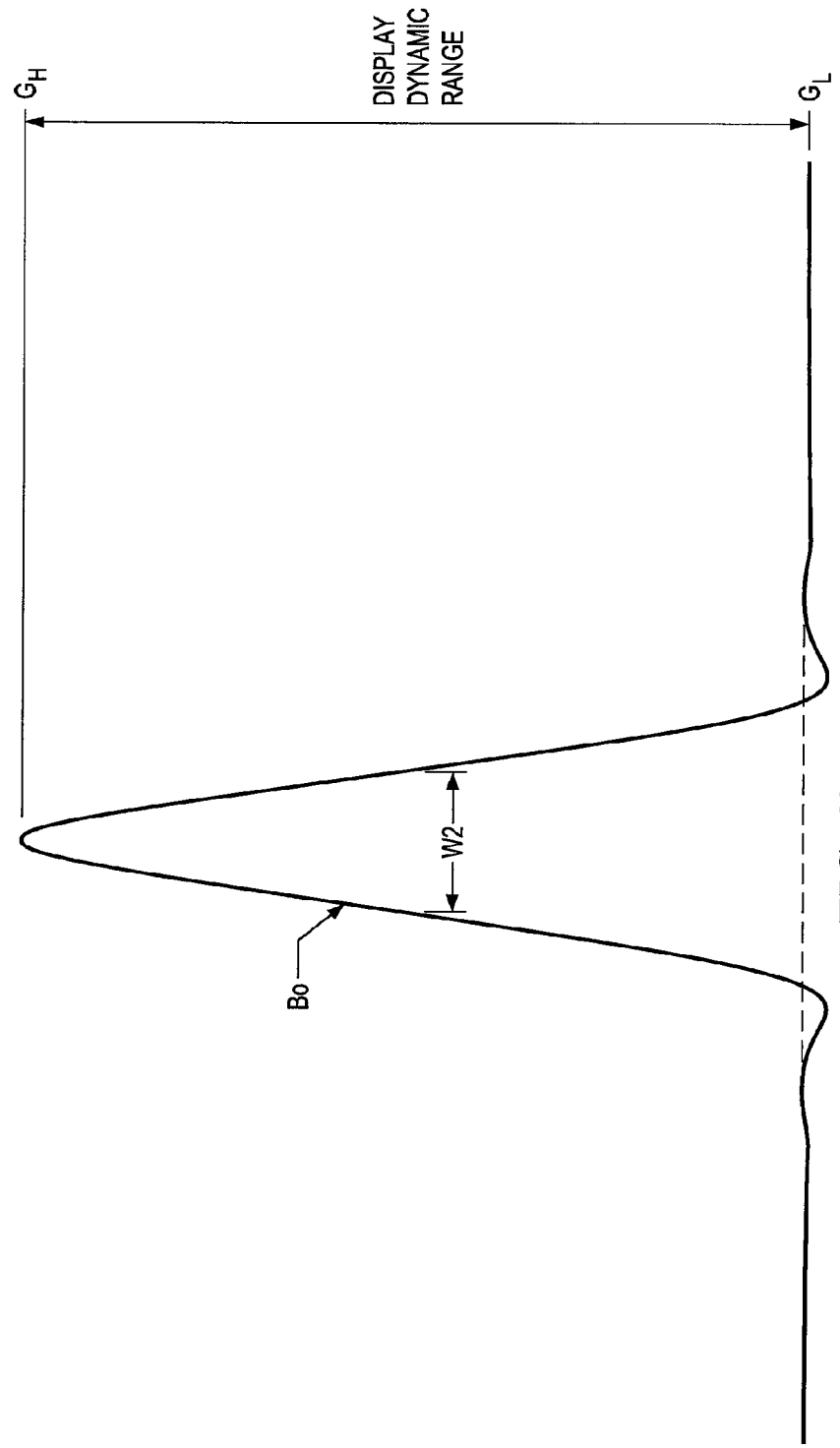
FIG. 3B shows an exemplary dynamic resolution beam as may be synthesized from the sample beams of FIG. 3A according to embodiments of the invention.

To illustrate the foregoing concepts, beam $B_O$ of FIG. 3B shows a representation of a DR beam $B_o(\theta)$ synthesized from the sample beam signals of sample beams $B_U$ and A (e.g., $B_o(\theta)=B_u(\theta)+\alpha A(\theta)$, where $\alpha=1$). The sidelobe of Beam $B_O$ has been greatly reduced. However, the mainlobe was relatively broadened as compared to the mainlobe of the Sinc beam, as shown by W1 of FIG. 3A and W2 of FIG. 3B. Although such a spread mainlobe generally reduces the resolution of the resulting image, improved image quality is provided by the DR beam of such an embodiment through a balance of relatively slight mainlobe spread and significant reduction in sidelobes.

Figure 4:
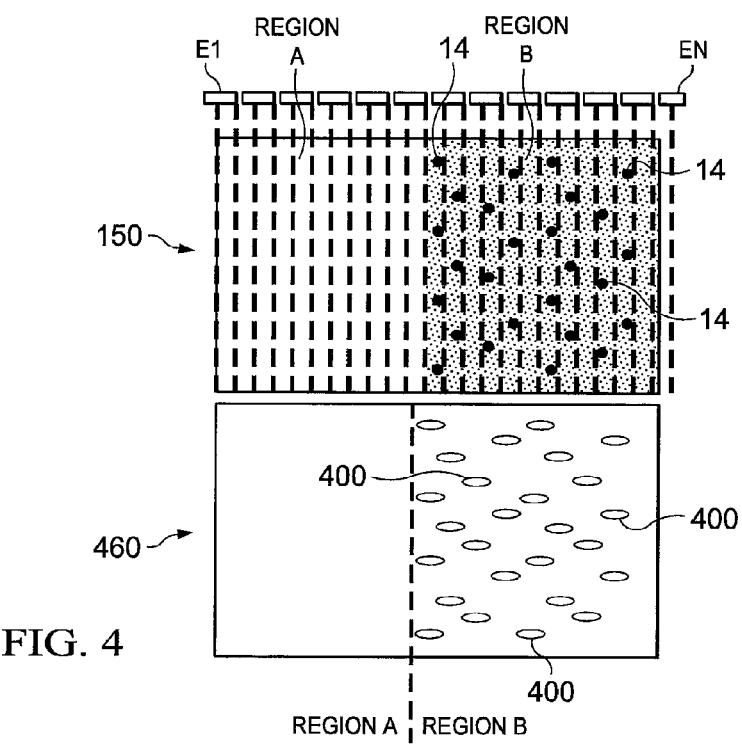
FIG. 4 shows a representation of an image generated using a DR beam of an embodiment of the invention.
Figure 1C:
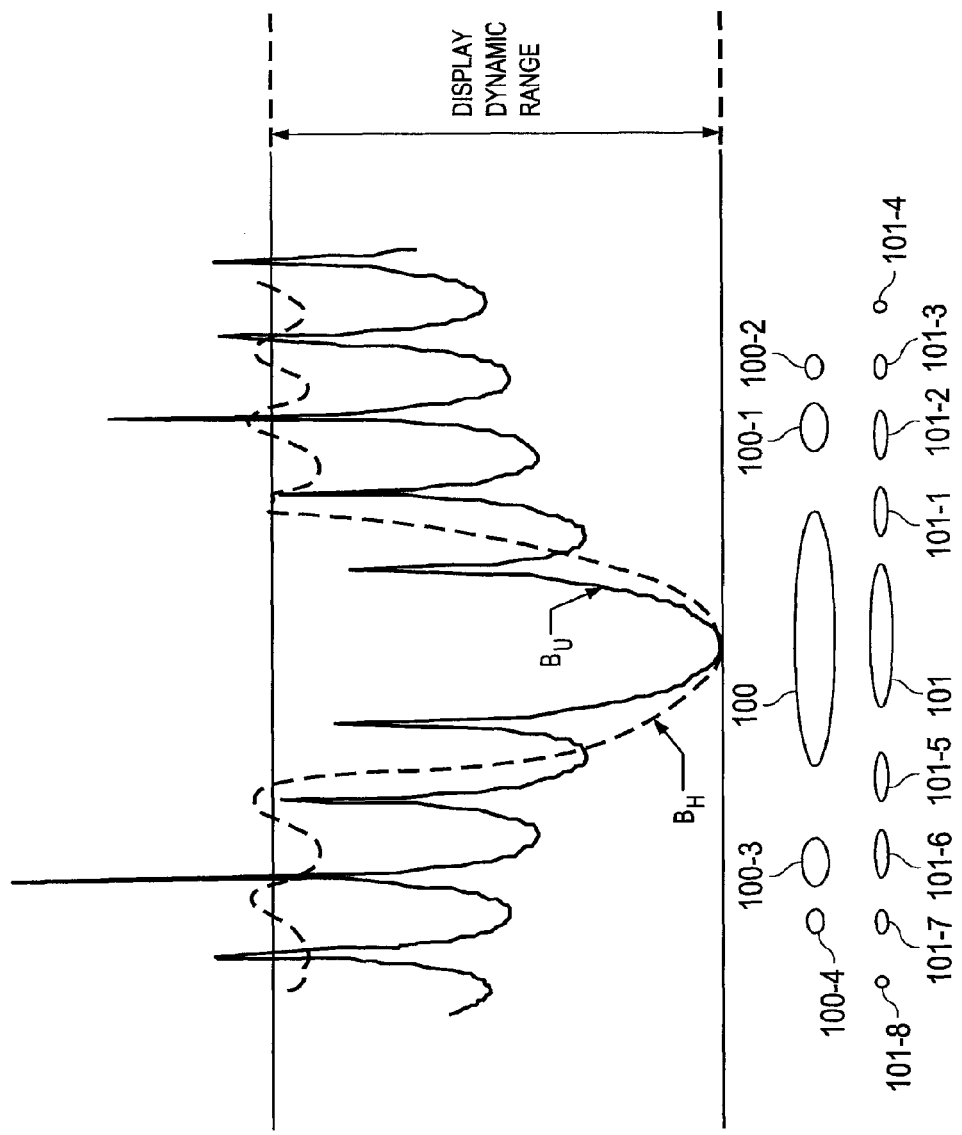

FIG. 4 shows a representation of an image generated using DR beams synthesized according to an embodiment of the invention. In particular, FIG. 4 illustrates image 460, showing an object of interest (e.g., object of interest representations 400 aggregating to represent an object of interest) within a volume being imaged, as generated from scanning sample beams (e.g., sample beams $B_U$ and A of FIG. 3A) to synthesize a DR beam (e.g., DR beam $B_O$ of FIG. 3B). As shown, in FIG. 3B, the dynamic range of the display for image 460 corresponds to the information in the DR beam signal between the lower cutoff, $G_L$, and the upper cutoff, $G_H$. No sidelobe artifacts are visible in image 460 because the sidelobes of synthesized DR beam have fast fall off and the images the sidelobes do create are below the lower cutoff, $G_L$. The generated images corresponding to point scatterers 14 are spread only slightly in image 460 because of the reduction in the mainlobe width of the DR beam. Thus the texture of the image is well preserved and little or no artifacts are present in either regions A or B of image 460.

Figure 5A:
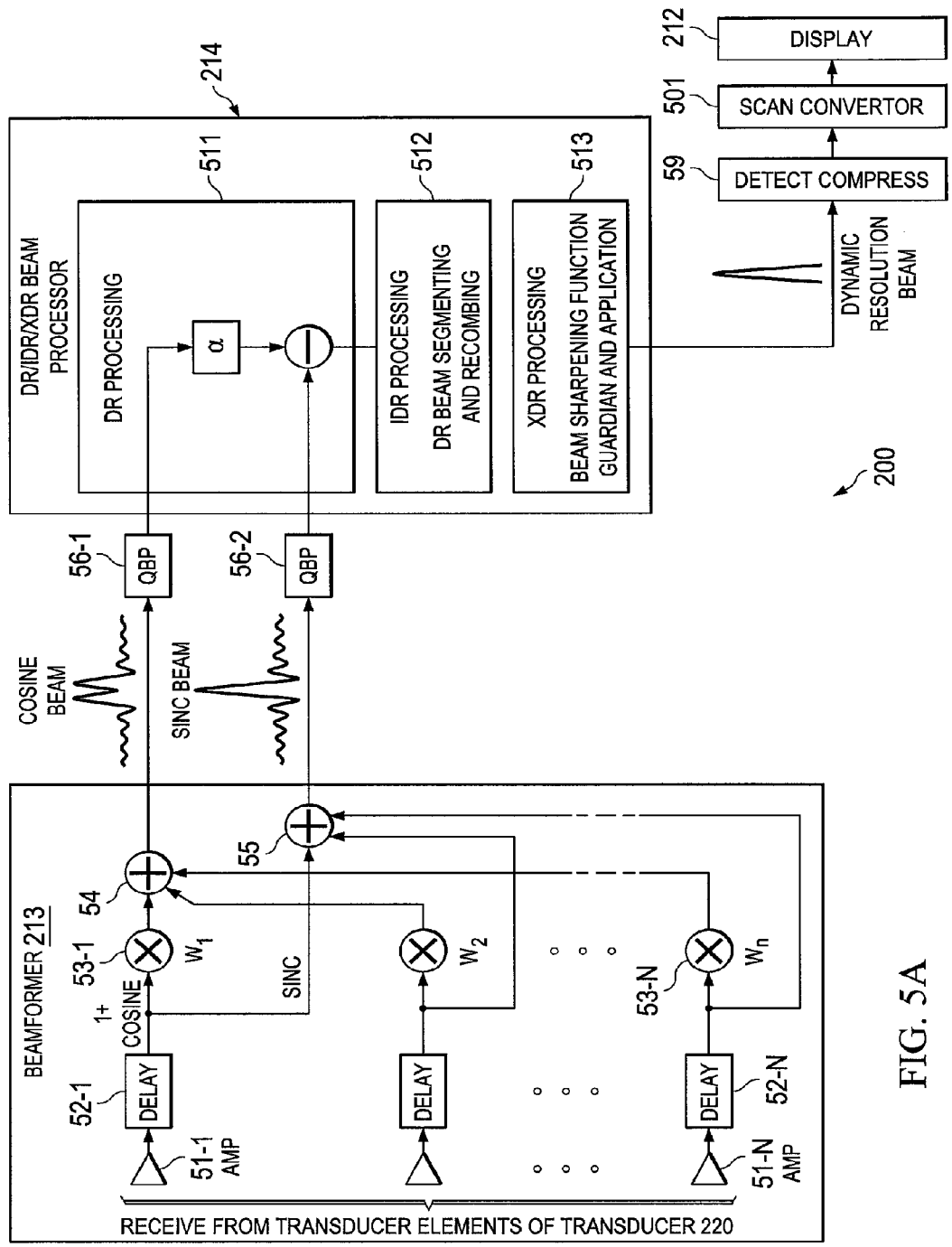
FIGS. 5A and 5B show details of embodiments of the system of FIG. 2 adapted to synthesize a dynamic resolution beam, such as that of FIG. 3B, according to embodiments of the invention.
Figure 5B:
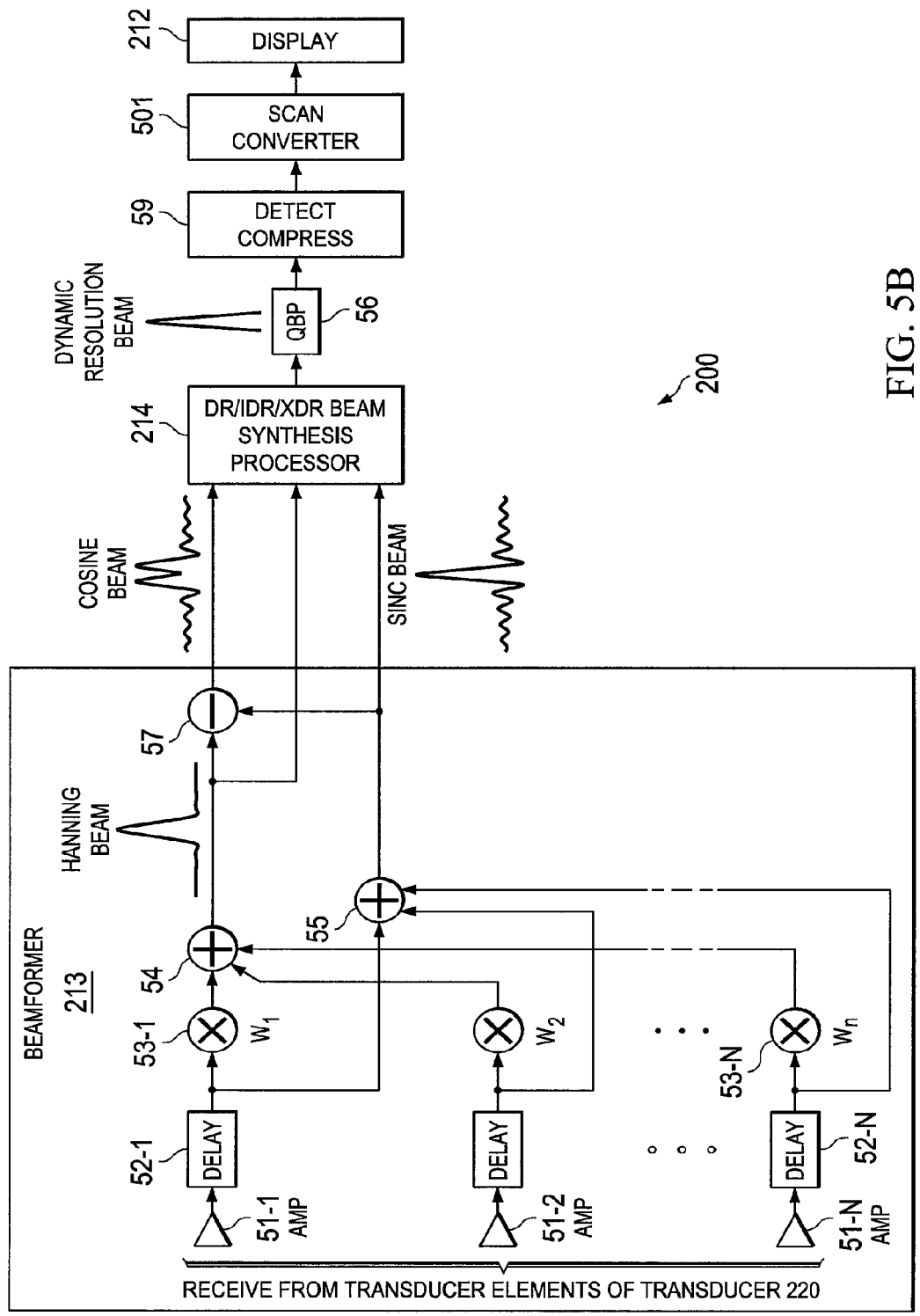

FIGS. 5A and 5B show additional details of embodiments of ultrasound imaging system 200 adapted to synthesize a DR beam (e.g., DR beam $B_O$ of FIG. 3B) using a plurality of sample beams (e.g., sample beams $B_U$ and A of FIG. 3A). The exemplary systems of FIGS. 5A and 5B utilize beamformer 213 to form two sample beam signals for DR beam synthesis. Beamformer 213 of the illustrated embodiments comprise various signal processing, weighting, and combining circuitry, as may be operable under control of a control processor, such as DR/IDR/XDR beam synthesis processor 214, to form sample beam signals as described herein.

In the illustrated embodiments, the signals provided from the transducer elements (e.g., transducer elements E1-EN as shown in FIG. 1A) are processed by amplifiers 51-1 to 51-N, such as may comprise low noise amplifiers providing transducer signal amplification for subsequent beamforming processing. Elements 52-1 to 52-N provide signal phase adjustment (delay) for each transducer element signal and elements 53-1 to 53-N provide signal amplitude adjustment (weighting) for each transducer element signal. Elements 52-1 to 52-N and 53-1 to 53-N thus both apply beamforming parameters to the transducer element signals. Combiners 54 and 55 provide combining (e.g., summing) of the transducer element signals to form a resulting beam signal. Accordingly, elements 52-1 to 52-N and combiner 55 cooperate to provide sample beam beamformer 213a of embodiments of the present invention and elements 52-1 to 52-N, elements 53-1 to 53-N, and combiner 54 cooperate to provide sample beam beamformer 213b of embodiments.

In the embodiment of FIG. 5A, appropriately delayed transducer element signals are combined at combiner 55 to provide a Sinc beam signal as the aforementioned first sample beam signal. Appropriately delayed and weighted transducer element signals are combined at combiner 54 to provide a cosine apodized beam signal as the aforementioned second or auxiliary sample beam signal. In operation according to an embodiment of the invention the Sinc beam and cosine apodized beam are simultaneously formed (e.g., using a same set of transducer element signals).

Beam signal conditioning and/or processing may be provided according to embodiments prior to, in combination with, or subsequent to DR beam synthesis processing, if desired. For example, the cosine apodized beam signal of the illustrated embodiment is provided to quadrature band pass filter 56-1 while the Sine beam signal is provided to quadrature band pass filter 56-2 for facilitating DR beam synthesis processing in the vector space. Additional or alternative sample beam signal conditioning may comprise analog to digital conversion (e.g., where a digital signal processor (DSP) is used in synthesizing DR beams herein), amplification, noise canceling, etc.

The Sine beam signal and cosine apodized beam signal are provided to DR/IDR/XDR beam synthesis processor 214 of the illustrated embodiment for DR beam signal synthesis. The embodiment of DR/IDR/XDR beam synthesis processor 214 illustrated in FIG. 5A includes a plurality of beam processing circuits, shown here as DR processing 511, IDR processing 512, and XDR processing 513, to provide dynamic resolution processing as described herein. It should be appreciated, however, that embodiments of the invention may not implement all of the beam processing circuits of the illustrated embodiment. For example, embodiments may implement only DR processing (e.g., DR processing 511) as described herein or a combination of DR processing and IDR processing (e.g., DR processing 511 and IDR processing 512), if desired. DR/IDR/XDR beam synthesis processor 214 may comprise a general purpose processor operable under control of an instruction set to provide operation as described herein, a DSP, an application specific integrated circuit (ASIC), a programmable gate array (PGA), etc. configured to provide beam processing circuits as described herein. Operation of such a DR/IDR/XDR beam synthesis processor is described more fully below with reference to the process of FIG. 6.

It should be appreciated that the beam signals synthesized according to embodiments of the invention are utilized in image generation, such as the aforementioned generation of ultrasound images. Accordingly, the output of DR/IDR/XDR beam synthesis processor 214 of embodiments is provided to circuitry for such image generation. For example, the synthesized dynamic resolution beam signals of the illustrated embodiment are provided to detect and compress circuit 59, such as to remove the phase of the signal and to provide mapping of the magnitude of the signal for scan conversion. Scan converter 501 of embodiments transforms the magnitude of the signal from the acquisition space into the display space for presentation to the user via display 212.

One of the problems of implementing a cosine apodized beam is the combining of the transducer element signals (e.g., at combiner 54 of FIG. 5A). The cosine function oscilates between −1 and +1. Thus, when performing a weight and a sum, one transducer element signal (channel) may be −1 while and another transducer element signal (channel) may be +1, whereby there is a probability that one channel will cancel out the other channel. The positive and negative values in each channel associated with the use of the cosine function may cause cancellation in the delay-and-sum process in the beamforming resulting in dynamic range limitation. Moreover, since the cosine function goes from −1 to +1 and thus crosses zero, certain transducer elements will receive a very small signal. To overcome this problem, front end circuitry of an image processing system (e.g., an A to D converter of the front end circuitry) may need to have a very wide dynamic range.

The foregoing problems associated with the use of a cosine apodization are avoided in the embodiment of FIG. 5B, wherein a raised cosine apodized beam (e.g., Hanning beam) is formed by beamformer 213. Thus, instead of using the beamformers to directly form a cosine apodized beam, the embodiment of FIG. 5B operates to form a raised cosine apodized beam (e.g., a Hanning beam) in addition to a Sine beam for use in DR beam synthesis. Thereafter, a second or auxiliary sample beam signal used in the DR beam synthesis described above may be calculated by taking the difference between the signals of the first sample beam (here a Sine beam) and the raised cosine apodized beam. Accordingly, in the embodiment of FIG. 5B, appropriately delayed transducer element signals are combined at combiner 55 to provide a Sinc beam signal as the aforementioned first sample beam signal. Transducer element signals weighted in a raised cosine function are combined at combiner 54 to provide a raised cosine apodized beam signal. An advantage of forming such a raised cosine apodized beam on the front end is that combiner 54 only need deal with positive signals, thereby further suppressing noise.

In ultrasound imaging, dynamic focusing is often implemented in conjunction with a variable aperture. In other words, different aperture sizes are used for forming beams at different depths. Generally, it is preferred to increase the aperture size as depth increases to maintain resolution at various depths in an image. The Sinc beam and the cosine apodized beam can be formed using apertures of different sizes that vary with depth. Since the number of channels implemented in a beamformer is generally limited, the aperture size for beamforming stops growing at certain depth when the all channels available for beamforming are utilized. From this certain depth on, all received channels are used to form beam with a constant aperture.

In generating a raised cosine beam signal for example, the inputs to amplifiers 51-I to 51-N of the embodiment illustrated in FIG. 5B represent signals from the particular transducer elements of the transducer. For a beamformer of N channels, the largest aperture comprises N transducer elements to form-beams with N channels. When the aperture varies with depth, certain calculations may only need to use a subset of the transducer elements (e.g., a raised cosine function for various depths may be calculated for the selected transducer elements or selected aperture). In a preferred embodiment, for every raised cosine function calculation, the system of embodiments looks for the best set of weighting (e.g., settings for appropriate ones of elements 51-I to 52-N and 53-I to 53-N) to achieve best DR beam using two sample beams.

After the signals are combined by combiners 54 and 55 of FIG. 5B, the resulting beam signals are themselves combined by combiner 57, providing subtractive combining in the illustrated embodiment, to provide a second or auxiliary sample beam (here a cosine apodized beam) for use in DR beam synthesis according to embodiments. It should be appreciated from the discussion above that the raised cosine or Hanning beam, as initially generated by combiner 54, may be the resulting beam from DR beam synthesis processing in particular situations (e.g., where the parameter α=1 in embodiments). Thus, rather than regenerate a raised cosine apodized beam from the first sample beam and second or auxiliary sample beam, embodiments may utilize the raised cosine apodized beam originally generated by combiner 54. The output of combiner 54 is therefore shown coupled to DR/IDR/XDR beam synthesis processor 214 to provide the raised cosine apodized beam signal thereto, in addition to the first (Sinc beam) and second (cosine apodized beam) sample beams.

The Sine beam signal and cosine apodized beam signal are provided to DR/IDR/XDR beam synthesis processor 214 of the illustrated embodiment for dynamic resolution beam signal synthesis as described herein. Accordingly, DR/IDR/XDR beam synthesis processor 214 of the embodiment of FIG. 5B may be configured as discussed with respect to FIG. 5A above.

As with the embodiment of FIG. 5A discussed above, beam signal conditioning and/or processing may be provided according to embodiments of the present invention prior to, in combination with, or subsequent to DR beam synthesis processing, if desired. For example, in the embodiment of FIG. 5B DR/IDRXDR beam synthesis processor 214 operates in the RF realm (i.e., signals are combined as RF signals) and the synthesized dynamic resolution beam signal of the illustrated embodiment is provided to quadrature band pass filter 56 for signal conditioning. Additional or alternative beam signal conditioning may comprise analog to digital conversion (e.g., where a digital signal processor (DSP) is used in synthesizing DR beams herein), amplification, noise canceling, etc.

As with the embodiment of FIG. 5A, the DR beam signal synthesized by DR-XDR processor 214 of the embodiment of FIG. 5B is provided to circuitry providing image generation. Specifically, the synthesized DR beam signal of the illustrated embodiment is provided to detect and compress circuit 59, such as to remove the phase of the signal and to provide mapping of the magnitude of the signal for scan conversion. Scan converter 501 of the illustrated embodiment transforms the magnitude of the signal from the acquisition space into the display space for presentation to the user via display 212.

Figure 6:
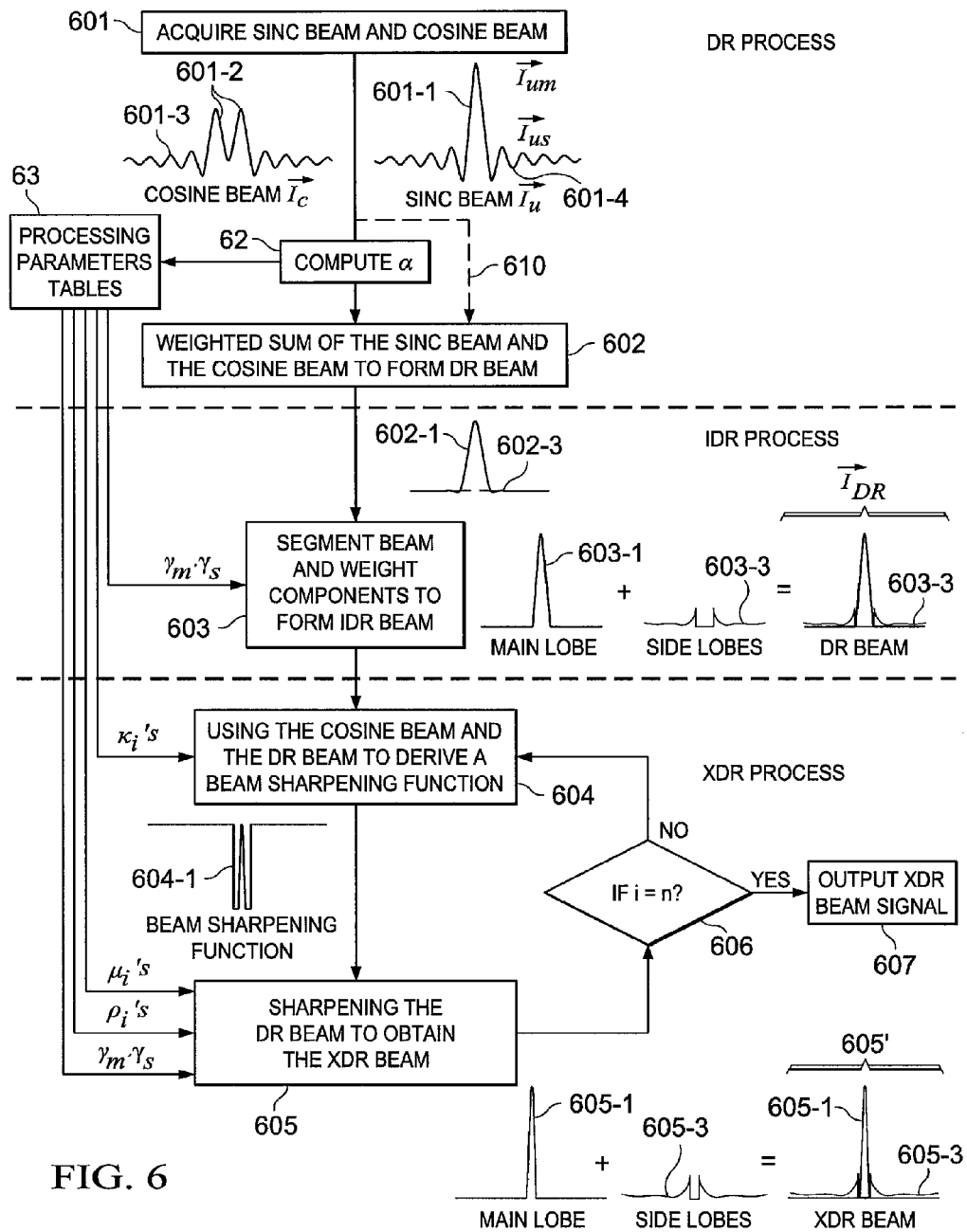
FIG. 6 illustrates exemplary operation of the DR-XDR processor of FIGS. 5A and 5B according to embodiments of the invention.

FIG. 6 shows detail of an embodiment of a dynamic resolution beam synthesizing process, as may be provided by DR/IDR/XDR beam synthesis processor 214 of FIGS. 5A and 5B, for achieving sidelobe reduction of a scan beam according to the concepts herein. In particular, in the embodiment illustrated in FIG. 6 the processes shown above the upper dotted line provide DR beam synthesis correspond to operation of DR processing 511 of FIG. 5A, the processes shown between the upper and lower dotted lines provide IDR beam synthesis corresponding to operation of IDR processing 512 of FIG. 5A, and the processes shown below the lower dotted line provide XDR beam synthesis corresponding to operation of XDR processing 513 of FIG. 5A.

In operation of DR processing 511 of DR/IDR/XDR beam synthesis processor 214 of embodiments, the first sample beam signal and second or auxiliary sample beam signal, preferably weighted using the parameter α, are combined to synthesize a DR beam signal. Accordingly, at process 601 a first sample beam (e.g., a Sinc beam) having mainlobe 601-1 and sidelobes 601-4 formed for each sample point in a scanned area (e.g., each look direction) of an object being scanned (e.g., tissue area) is acquired. Additionally, a second or auxiliary sample beam (e.g., a cosine apodized beam) having mainlobe 601-2 and sidelobes 601-3 formed for each sample point in a scanned area of a volume being imaged is acquired. In operation according to process 601 of an embodiment the first sample beam signal $\vec{I}_u$ (including mainlobe signal component $\vec{I}_{uM}$ and sidelobes signal component $\vec{I}_{uS}$) and second or auxiliary beam signal $\vec{I}_c$ are acquired using the aforementioned Sinc and cosine apodized beams for every sample.

The first sample beam signal $\vec{I}_u$ and second or auxiliary beam signal $\vec{I}_c$ of the illustrated embodiment are input into process 62 which computes the parameter α for use in the weighted combining of the sample beams. As discussed above, the parameter α is a sidelobe cancellation parameter in the DR beam synthesizing process of embodiments and is used in synthesizing a DR beam from the sample beams (e.g., Sine and cosine apodized beams). In an alternate embodiment, the computation of the parameter α may be omitted and, thus, the process flow may proceed directly to process 602, as shown by dashed line 610.

The following vector analysis is helpful in understanding the computation of the parameter α in process 62 as may be used according to embodiments of the invention. The aforementioned first sample beam (e.g., Sine beam) signal $\vec{I}_u$ can be decomposed into two components such that $$\underbrace{\vec{I}_u}_{\text{Echo received}} = \underbrace{\vec{I}_{uM}}_{\text{Mainlobe}} + \underbrace{\vec{I}_{uS}}_{\text{Sidelobe}}.$$

The unity vector $\vec{u}_{uM}$ defines the look direction of the mainlobe, wherein $$\vec{u}_{uS} = \frac{\vec{I}_{uM}}{|\vec{I}_{uM}|},$$

and the unity vector $\vec{u}_{uS}$ defines the look direction of the sidelobe, wherein $$\vec{u}_{uS} = \frac{\vec{I}_{uS}}{|\vec{I}_{uS}|}.$$

The aforementioned second or auxiliary sample beam (e.g., cosine apodized beam) signal $\vec{I}_c$ can be represented by $\vec{I}_c = |\vec{I}_c|\vec{u}_c$. When the second or auxiliary sample beam (e.g., cosine apodized beam) is aligned with the sidelobe of the first sample beam (e.g., Sine beam), the unity vector of the second or auxiliary (e.g., cosine apodized) beam, $\vec{u}_c$, will be aligned with the unity vector of the sidelobe component of the first sample beam with opposite phase (e.g., Sinc beam). That is, $\vec{u}_c = -\vec{u}_{uS}$, where $$\vec{u}_c = \frac{\vec{I}_c}{|\vec{I}_c|}.$$

Thus, the sidelobe components of the first sample beam signal $\vec{I}_u$ along $\vec{u}_c$ is $$(\vec{I}_u \cdot \vec{u}_{uS})\vec{u}_c = -\frac{\vec{I}_u \cdot \vec{I}_c}{|\vec{I}_c|}\vec{u}_c = -\vec{I}_u \cdot \frac{\vec{I}_c}{|\vec{I}_c|}\vec{u}_c = -\vec{I}_u \cdot \frac{\vec{I}_c}{|\vec{I}_c|}\frac{\vec{I}_c}{|\vec{I}_c|} = \alpha \vec{I}_c,$$

where $\alpha = -\frac{\vec{I}_u \cdot \vec{I}_c}{|\vec{I}_c|}.$

It should be appreciated that the DR beam synthesizing processes herein can be applied to all samples for an image by computing the parameter $$\alpha(n, z_n) = -\frac{\vec{I}_u(n, z_n) \cdot \vec{I}_c(n, z_n)}{|\vec{I}_c(n, z_n)|^2}$$

for every sample located at different depths of every scanning beam. For example, $\vec{I}_u(n,z_n)$ and $\vec{I}_c(n,z_n)$ are the signals acquired at depth $z_n$ from the $n^{th}$ unprocessed first sample beam (e.g., an unapodized Sinc beam in the foregoing example) and the second or auxiliary sample beam (e.g., an apodized cosine apodized beam in the foregoing example). Thus, $\vec{I}_{DR}(n,z_n) = \vec{I}_u(n,z_n) + \alpha(n,z_n)\vec{I}_c(n,z_n)$. As discussed above, it is desirable according to embodiments of the invention that the value of the parameter $\alpha(n,z_n)$ be bounded between 0 and 1, or $0 \le \alpha(n,z_n) \le 1$. For example, in a case when the clutter from the undesired direction is very large at the sample location $(n,z_n)$ then $\alpha(n,z_n)$ is set to one in the DR beam synthesis process to maximize the amount of sidelobe suppression. In this example, 100% of the signal acquired from the second or auxiliary sample beam (e.g., cosine apodized beam) is summed to the signal from the first sample beam (e.g., Sine beam) at this time. However, by doing so the mainlobe $\vec{I}_n(n,z_n)$ is spread as a result of the summing process. That is, some spreading of the mainlobe occurs at samples $(n, z_n)$ when $\alpha(n,z_n) \ne 0$. Thus, in the DR synthesization process of embodiments, $\alpha(n,z_n)$ dynamically changes from sample to sample depending upon the power of the clutter near the sample location $(n,z_n)$.

The case $\alpha=0$ represents a situation that clutter received from a Sine beam is relatively small that no signal from the cosine apodized beam is needed for suppressing the sidelobe to reject the clutter. In this case, the object being imaged is delineated by the mainlobe of the Sine beam whose width is spread according to the diffraction limited resolution.

The case α=1 represents another situation that the clutter received from the Sinc beam is so large that 100 percent of the signals received from the cosine apodized beam is used to suppress the sidelobes. This results in a Hanning beam with a mainlobe that is spread much larger than diffraction limited resolution for object delineation. Delineating an object being imaged with different resolution may cause perceptive distortion of the object for image interpretation. Further, in an extreme situation where the clutter is so strong that the sidelobe of the Hanning beam (when α=1) is not sufficient to suppress (or roll off) the clutter, the sample is contaminated with clutter that degrade the image quality.

Signal components attributed to the mainlobe or the sidelobes of a beam can be segmented in the IDR and XDR process of embodiments of the invention. By manipulating the signals acquired from the DR beam and the cosine apodized beam, a category of signal components corresponding to beams of different shapes with different geometrical properties can be produced. The desired signal components with much sharper mainlobe and low sidelobes can be synthesized to equalize the mainlobe resolution and sidelobe level to improved the image quality.

The parameter $\alpha(n, z_n)$ indicates the amount of clutter, its strength and how it is distributed near a sample point, and can be used to control the other beamforming parameters to sharpen the mainlobe and attenuate the sidelobe in the IDR and XDR process of embodiments of the invention. The parameter tables 63 of the illustrated embodiment comprise lookup tables to map the desired beamforming parameters using α. These processing parameters may be predetermined for a variety of depths and conditions, may be calculated dynamically based on various operating conditions and parameters, etc. In one embodiment, parameters of processing parameter tables 63 are set to coincide with the depth and look direction on an aperture by aperture basis for each scan beam signal.

From the foregoing, DR beams of embodiments are formed by combining the signal from the Sinc beam with α percentage of the signal from the cosine apodized beam to reduce the sidelobe, where α may be determined according to the minimum power criterion that results in $$\alpha = \frac{-\vec{I}_u \cdot \vec{I}_c}{|\vec{I}_c|^2}$$

according to embodiments. In other words, the DR beam signal $\vec{I}_{DR}$ of embodiments is synthesized according to $$\vec{I}_{DR} = \vec{I}_u + \alpha \vec{I}_c = \vec{I}_u - \frac{\vec{I}_u \cdot \vec{I}_c}{|\vec{I}_c|^2} \vec{I}_c.$$

Accordingly, process 602 of embodiments of the invention operates to form the DR beam signal $\vec{I}_{DR}$ from a weighted sum of the Sinc and cosine apodized beam signals. For example, a DR beam signal, $\vec{I}_{DR}$, corresponding to a synthesized DR beam, $B_o(\theta)$, may be formed from a sum of the Sinc beam, $B_u(\theta)$, signal $\vec{I}_u$ and the weighted cosine apodized beam, $A(\theta)$, signal $\vec{I}_c$ (e.g., $B_o(\theta) = B_u(\theta) + \alpha A(\theta)$) at process 602.

Figure 6A:
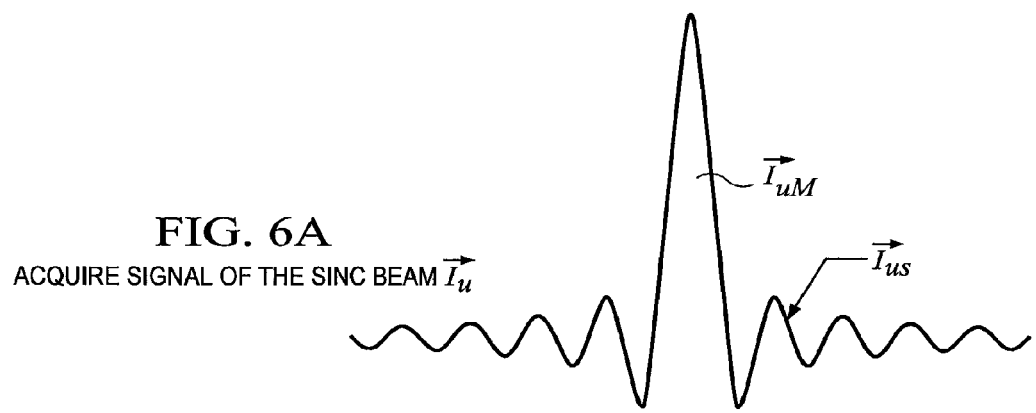
FIGS. 6A-6C illustrate combining the signals of a first sample beam signal and a second or auxiliary sample beam signal for dynamic resolution beam synthesis in accordance with the operation of a process of FIG. 6 according to embodiments.
Figure 6B:
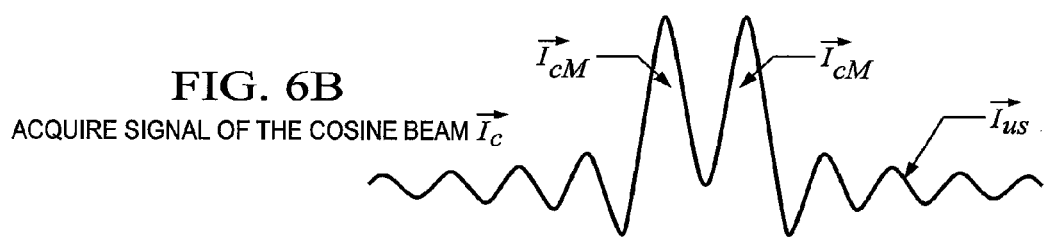
Figure 6C:
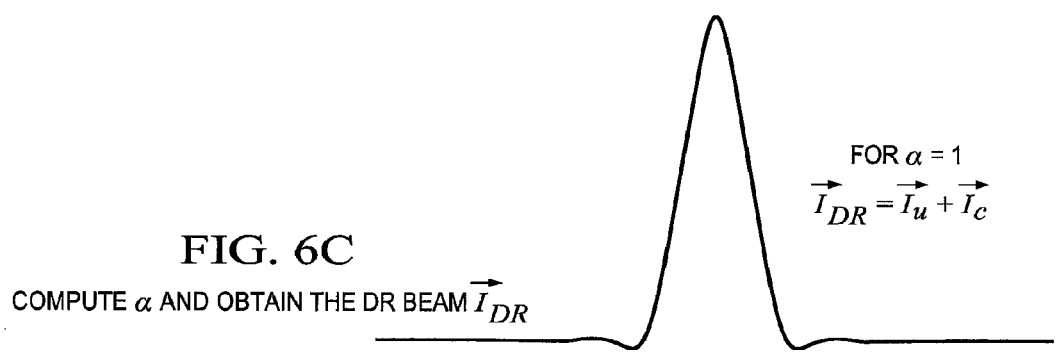

The synthesized DR beam, $B_o(\theta)$, corresponding to the DR beam signal, $\vec{I}_{DR}$, formed at process 602 has mainlobe 602-1 with reduced or minimized sidelobes 602-3. FIGS. 6A through 6C illustrate synthesizing a DR beam signal, $\vec{I}_{DR}$, corresponding to a synthesized DR beam, $B_o(\theta)$, from a sum of the Sine beam, $B_u(\theta)$, signal $\vec{I}_u$ and the weighted cosine apodized beam, $A(\theta)$, signal $\vec{I}_c$ (e.g., $B_o(\theta) = B_u(\theta) + \alpha A(\theta)$) in accordance with the aforementioned operation of process 602 using sample beams as provided by beamformer 213. Specifically, FIG. 6A shows Sinc beam signal $\vec{I}_u$ received from the Sinc beam (first sample beam) and FIG. 6B shows the cosine apodized beam signal $\vec{I}_c$ received from the cosine apodized beam (second or auxiliary sample beam). FIG. 6C shows a synthesized DR beam resulting from the sidelobe component being removed from Sine beam signal $\vec{I}_u$ in the case where α=1.

As described above, one technique for synthesizing a DR beam signal is to combine the Sinc beam and cosine apodized beam signals $\vec{I}_u$ and $\vec{I}_c$ (e.g., $\vec{I}_{DR} = \vec{I}_u + \alpha \vec{I}_c$, 0≤α≤1). However, instead of forming a cosine apodized beam to synthesize the DR beam, embodiments such as that of FIG. 5B discussed above form a raised cosine beam (e.g., Hanning beam) for use in synthesizing a DR beam. For example, operation of process 602 using sample beams as provided by beamformer 214 of FIG. 5B provides DR beam signal synthesis comprising taking the difference between the signals of a raised cosine beam and a Sinc beam $\vec{I}_{DR} = \vec{I}_u + \alpha(1 - \vec{I}_c)$, 0≤α≤1. Let $\vec{I}_h$ be the raised cosine beam, then $\vec{I}_{DR} = \vec{I}_u + \alpha(\vec{I}_h - \vec{I}_u)$, 0≤α≤1). Such an embodiment may operate to form a cosine apodized beam from the raised cosine beam and the Sinc beam, thus aligning the cosine apodized beam with the sidelobes of the Sinc beam. The use of such a cosine apodized beam in DR beam synthesis substantially suppresses the sidelobes of Sine beam signal $\vec{I}_u$ while avoiding spread of the mainlobe of the Sine beam signal $\vec{I}_u$.

The DR beam signal synthesized at process 602, providing suppressed sidelobes and minimized mainlobe spread, may be utilized by ultrasound imaging system 200 for generation of high quality images. However, embodiments of the invention provide additional dynamic resolution beam synthesis processing to further improve the synthesized beam characteristics. Accordingly, processing according to the illustrated embodiment proceeds to process 603 for additional dynamic resolution beam synthesis.

In operation of IDR processing 512 of DR/IDR/XDR beam synthesis processor 214 of embodiments, certain geometrical and morphological properties of different beams (e.g., one or more of the sample beams and/or synthesized DR beam) are utilized in further processing dynamic resolution beams. In particular, the signals of a beam are decomposed into two components: a component corresponding to mainlobe and another component corresponding to the sidelobes. These component signals are then recombined (weighted sum) to create a new signal corresponding to a new beam (an IDR beam of embodiments of the present invention) with very narrow mainlobe and very low sidelobes.

Process 603 of the embodiment illustrated in FIG. 6 provides processing of a synthesized DR beam signal and one or more sample beam signals (e.g., the second or auxiliary sample beam signal) to segment component beams. Signals from these component beams are then used to compose a new signal as if it is received from a high performance beam (an IDR beam). The signal decomposition and reconstruction process is operated at every sample point at each look direction to optimize the detailed and contrast resolution of the entire image according to embodiments of the invention.

Figure 6D:
FIGS. 6D-6I(3) illustrate isolation of a mainlobe signal component from a first sample beam signal for improved dynamic resolution beam synthesis in accordance with the operation of a process of FIG. 6 according to embodiments FIGS. 6J-6L(4) illustrate use of a beam shaping function in operation of an iteration of enhanced dynamic resolution beam synthesis in accordance with the operation of a processes of FIG. 6 according to embodiments.
Figure 6E:
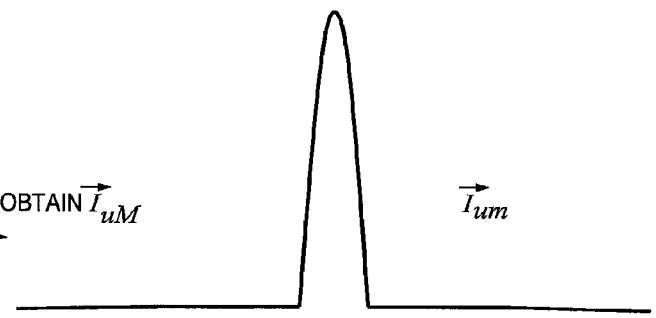

Beam segmentation, manipulation, and recombination by operation of process 603 to provide synthesis of IDR beams according to embodiments is illustrated in FIGS. 6D-6I. As discussed above, where the parameter $\alpha>0$ DR beam synthesis according to embodiments will result in mainlobe spread in addition to suppression of sidelobes. IDR beam processing as provided by process 603, and as illustrated in FIGS. 6D-6I (for $\alpha=1$.), operates to avoid such mainlobe spread by segmenting the mainlobe from the first sample beam (unspread from combining with the second or auxiliary sample beam) using the synthesized DR beam. To segment the mainlobe from the first sample beam, process 603 of embodiments computes the minimum between the DR beam ($\vec{T}_{DR} = \vec{T}_u + \alpha(\vec{T}_h - \vec{T}_u)$) and the second or auxiliary beam ($\vec{T}_c$), $\vec{M} = \phi(\vec{T}_{DR})\text{MIN}(|\vec{T}_{DR}|, |I_C|)$ where $\phi$ provides phase alignment, to give a mainlobe spread component as shown in FIG. 6D. This mainlobe spread component ($\vec{M}$) essentially comprises that part of the synthesized DR beam which is not the mainbeam of the first sample beam ($\vec{T}_u$). Accordingly, the mainlobe spread component may be subtracted from the DR beam to provide a first sample beam mainlobe component, $\vec{T}_{uM} = \vec{T}_{DR} - \vec{M}$, as shown in FIG. 6E. It should be appreciated that the first sample beam mainlobe component ($\vec{T}_{uM}$) of FIG. 6E provides a more narrow mainlobe than that of a DR beam ($\vec{T}_{DR}$) synthesized through the above described combining of sample beams and thus may be utilized in providing high quality image generation.

The exemplary embodiment represented in FIGS. 6D and 6E efficiently split the signal of the first sample beam (e.g., Sinc beam $\vec{T}_u$) into two components, a mainlobe component ($\vec{T}_{uM}$) and a sidelobe component ($\vec{T}_{uS}$). The magnitude of sidelobe component signal $|\vec{T}_{uS}|$ represents the clutter signal received by the sidelobe of the first sample beam in a neighborhood near to the sample point. The magnitude of the mainlobe component $|\vec{T}_{uM}|$ represents the signal received in an area insonified by the mainlobe of the first sample beam at the sample point that is spread according to the width of the mainlobe. The signal to clutter ratio varies from point to point depending upon the object being insonified. An image often is thus blemished at different levels by the clutters. Although it seems plausible that a clear, unblemished image can be reconstructed by retaining only the component signal from the mainlobe of the first sample beam and eliminating the component from its sidelobe, this is not necessarily so. It has been discovered for an imaging area where the magnitude of signal from the sidelobe are small relative to the magnitude of the signal from the mainlobe, removing the sidelobe component signal may result in improvement of image quality; but for other areas where the magnitude of signal from the sidelobe are large relative to the magnitude of the signal from the mainlobe, eliminating all signals from sidelobe in an image may generate a number of spotty "dark" areas that may cause problems in image interpretation. This is because the sidelobe of a beam integrates echo signal received from an extended area near to the sample point. At a sample point where the signal received from the mainlobe is much lower than that is from its sidelobe, the clutter component signal functionally interpolates the shape of the object that is helpful for image interpretation.

Accordingly, a signal derived from a new beam that is formed by weighted sum of the mainlobe component signal and a small amount of sidelobe component signal is preferred accordingly to embodiments of the present invention. In process 603 of embodiments of the invention, the weights for mainlobe signal and sidelobe signal are programmed and selected depending upon the magnitude of the signal from the mainlobe, the magnitude of the clutter signal from the sidelobe, the sidelobe signal to the mainlobe signal ratio and/or the DR parameter $\alpha$ at each sample point to optimize the image quality.

Figure 6F:
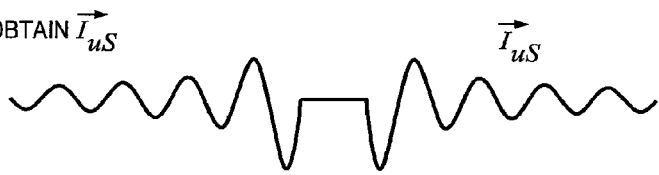
Figure 6G:
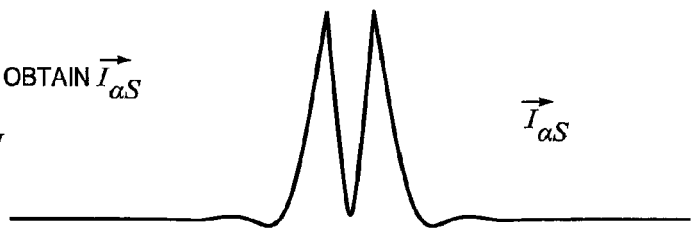
Figure 6H:
Figure 6I:
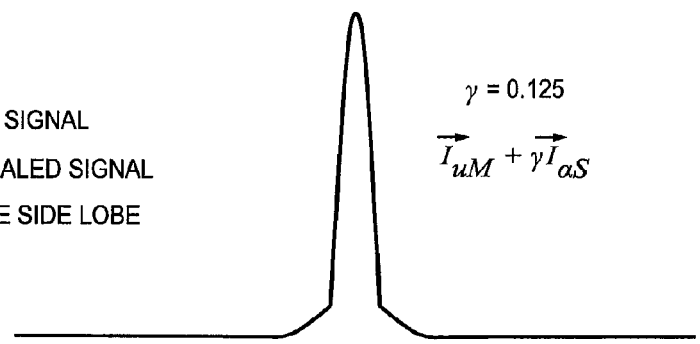

Further dynamic resolution processing according to process 603 of embodiments is represented by FIGS. 6F and 6I, wherein a mainlobe and a sidelobe rolloff, such as may be provided as an appropriately weighted sidelobe component, is added to the segmented first sample beam mainlobe component to synthesize an IDR beam. The sidelobe component signal shown in FIG. 6F is segmented from the signal of the first sample beam, for example the Sinc beam. It is known that the sidelobe level of the Sinc beam is rolling off with angle (or distance) at a rate ~6 db/octave that is relatively slow as compared to the DR beam when $\alpha>0$. Specifically, for the Hanning beam, (a DR beam when $\alpha=1$), the sidelobe is rolling off with angle at a rate ~18 db/octave that is much faster than that of the Sinc beam (DR beam when $\alpha=0$). A component signal $\vec{T}_{\alpha S}$ can be extracted by taking the difference between the signal of the DR beam $\vec{T}_{DR}$ and the mainlobe signal $\vec{T}_{uM}$ segmented from the Sinc beam, or $\vec{T}_{\alpha S} = \vec{T}_{DR} - \vec{T}_{uM}$.

FIG. 6G shows signal $\vec{T}_{\alpha S}$ corresponding to a beam whose sidelobes are geometrically distributed following the DR beam (for example, the Hanning beam when $\alpha=1$) with small residual mainlobe of the DR beam as a result of the subtraction process. As shown in FIGS. 6H and 6I, the signal $\vec{T}_{\alpha S}$ may be attenuated by a parameter $\gamma$ where $\gamma \leq 1$ then integrated with the signal $\vec{T}_{uM}$ to create a new signal $\vec{T}_{\alpha N} = \vec{T}_{uM} + \gamma \vec{T}_{\alpha S}$. $\vec{T}_{\alpha N}$ representing a signal corresponding to a beam (an IDR beam) whose lobe is geometrically distributed with angle (or distance) as shown in FIG. 6I. The center of the mainlobe of the IDR beam is as narrow as or more narrow than the mainlobe of the Sinc beam $\vec{T}_{uM}$. The low amplitude skirt of the mainlobe is then gradually spread and blended with the sidelobe that is rolling-off at a rate of the DR beam. Since $\gamma$ is chosen be smaller than one according to embodiments of the invention, the sidelobe will be attenuated by $20 \log \gamma$ db. For example, when $\gamma=0.125$, the sidelobe is attenuated by 18 db. Parameter $\gamma$ can be selected at each sample point adaptive to its beamforming parameter $\alpha$, the magnitude of component signal of different types or their ratio for optimal image quality.

It should be appreciated that the previous example shows the mainlobe of a Sine beam $\vec{T}_{uM}$ can be segmented from the DR beam (when $\alpha=1$) in the IDR process. A mainlobe narrower than the mainlobe of the Sinc beam $\vec{T}_{uM}$ can also be segmented from the other DR beams when $0<\alpha<1$. For example, when $\alpha=0$ $\vec{T}_{DR} = \vec{T}_u$. As in the IDR process, the signal corresponding to a narrow mainlobe component beam $\vec{T}_{\alpha M}$ may be segmented by computing $\vec{T}_{\alpha M} = \vec{T}_{DR} - \vec{M} = \vec{T}_{DR} - \phi(\vec{T}_{DR}) \mathrm{MIN}(|\vec{T}_{DR}|, |\vec{T}_c|) = \vec{T}_u - \phi(\vec{T}_u) \mathrm{MIN}(|\vec{T}_u|, |\vec{T}_c|)$. FIG. 6I(1) shows the segmented component beam $\vec{T}_{\alpha M}$ which is narrower than the mainlobe of the Sinc beam $\vec{T}_{uM}$. Further, a component signal $\vec{T}_{\alpha S}$ can be segmented by computing $\vec{T}_{\alpha S} = \vec{T}_{DR} - \vec{T}_{\alpha M}$ that $\vec{T}_{\alpha S}$ is a component signal corresponding to the sidelobe of the DR beam when $\alpha = 0$ as shown in FIG. 6I(2). A new IDR beam can be formed by computing $\vec{T}_{\alpha N} = \vec{T}_{uM} + \gamma \vec{T}_{\alpha S}$. $\vec{T}_{\alpha N}$ is a signal corresponding to the new beam whose sidelobe is attenuated by 18 db; however, the roll-off rate of the sidelobe is the same as that of the DR beam (for $\alpha = 0$) at 6 db per octave. FIG. 6I(3) shows the mainlobe, the sidelobe, the sidelobe roll-off rate of the DR beam, and the IDR beam when $\alpha = 0$ and $\alpha = 1$ in logarithmic scale, respectively.

It should be appreciated that the signal corresponding to the mainlobe of the other DR beams, $\vec{T}_{\alpha M}$ when $0 < \alpha < 1$, can be similarly segmented according to embodiments of the invention. The width of the segmented mainlobe of DR beam increases with $\alpha$ and $\vec{T}_{\alpha M} \le \vec{T}_{\alpha M}$ for $0 \le \alpha \le 1$. The sidelobe of the segmented IDR beam $\vec{T}_{\alpha N}$ for $0 \le \alpha \le 1$ is attenuated by $20 \log \gamma$ db and the sidelobe roll-off rate increases from 6 db per octave to 18 db per octave with $\alpha$ for $0 \le \alpha \le 1$.

It should be appreciated that the sidelobe component of the synthesized DR beam is substantially suppressed, although some spread of the mainlobe is present. The mainlobe of the DR beam is de-spread and its sidelobe rolloff rate is further improved, using a segmented component signal that is properly scaled in the IDR process. The IDR processing parameter $\gamma$ is selected to compose a signal corresponding to a synthesized beam whose mainlobe width is narrower or as narrow as the diffraction limited beam. The magnitude of an IDR mainlobe is gradually rolling-off and blended with the sidelobe whose level is determined by the parameter $\gamma$. The peak of the sidelobe of the IDR beam is first attenuated then continually rolling-off at a rate following the sidelobe of the DR beam according to embodiments. Such an IDR beam may be utilized to form an image with improved perceived image contrast and detailed image resolution.

The IDR beam signal synthesized at process 603, providing suppressed sidelobes without mainlobe spread, may be utilized by ultrasound imaging system 200 for generation of high quality images. However, preferred embodiments of the invention provide additional dynamic resolution beam synthesis processing to further improve the synthesized beam characteristics. Accordingly, processing according to the illustrated embodiment proceeds to process 604 for additional dynamic resolution beam synthesis.

In operation of XDR processing 513 of DR/IDR/XDR beam synthesis processor 214 of embodiments, the mainlobe width of a synthesized beam (e.g., the foregoing IDR beam) is further sharpened by an extended DR (XDR) beam synthesis process of preferred embodiments of the present invention. The beam is progressively or iteratively shaped through an XDR process for better beam control according to embodiments of the invention. A beam sharpening function of a XDR beam synthesis process may shape the mainlobe and the sidelobes of the processed beam to obtain a signal that is similar to a signal having been received from a beam with an extremely narrow mainlobe and very low sidelobes. For example, the mainlobe resulting from XDR beam synthesis of embodiments has a width corresponding to a transducer aperture substantially larger than that actually used in forming the sample beams from which the XDR beam is synthesized.

Process 604 of the XDR beam synthesis process illustrated in FIG. 6 creates a sharpening function 604-1 for use in synthesizing an XDR beam signal having a sharpened mainlobe. Such a sharpening function is applied at process 605, preferably iteratively, to a mainlobe component (e.g., mainlobe 605-1) to narrow the beam. As with IDR beam synthesis discussed above, an appropriately weighted sidelobe component (e.g., sidelobe 605-3), is added to the mainlobe component to synthesize a XDR beam (e.g., XDR beam 605') having desired rolloff. Iterative control 606 of the illustrated embodiment works in cooperation with the sharpening function generation of process 604 and the sharpening function application of process 605, to iteratively sharpen the mainlobe of a synthesized XDR beam. For example, in the illustrated embodiment, n is the number of iterations desired for XDR processing to achieve the resulting synthesized XDR beam signal which is output at process 607. Each iteration of the XDR beam processing shown in FIG. 6 provides an enhanced new synthesized beam, represented by XDR beam 605' of that iteration.

In sharpening (narrowing) attributes of the mainlobe of a beam provided to an XDR beam synthesis process of embodiments (e.g., the mainlobe component of the first, unapodized, sample beam, which also corresponds to the mainlobe of embodiments of a synthesized IDR beam) are manipulated for providing a beam shaping function. In understanding a beam shaping function of embodiments, it should be appreciated that mainlobe spreading in the above example where a DR beam is synthesized by combining a first and second or auxiliary sample beam (e.g., $B_o(\theta) = B_u(\theta) + \alpha A(\theta)$) results from the situation that the magnitude of the second or auxiliary sample beam in the angular interval defined by the mainlobe of the first sample beam is not nullified. As $\alpha$ percentage of signal from the second sample beam is summed to that of the first sampled beam for a reduction of sidelobe component signal of the first sample beam, the signal component from the mainlobe of the first sample beam will also be summed with the signal component from the second sample beam by the same percentage. For example, as is depicted in FIG. 3A the dual peak mainlobe of the cosine apodized beam (the second or auxiliary beam in the illustrated embodiment) is composed of the two geometrically shifted Sinc beams, one is located to the left of the Sinc beam mainlobe and the other is located to the right of the Sinc beam mainlobe. The mainlobe of a DR beam will intercept with the dual peak mainlobe of the cosine apodized beam at a look direction $\pm \theta_i$ where $|\theta_i| \le \theta_\alpha$. Where $\pm \theta_\alpha$ is the zero crossing of the mainlobe that defines beam resolution which amounts to $2\theta_\alpha$, when the sidelobe cancellation factor DR beam is $\alpha$. Since $\alpha$ is bounded between 0 and 1 in the DR beam of embodiments, when $\alpha = 0$, $|\theta_0| = \pi$ and when $\alpha = 1$, $|\theta_1| = 2\pi$. Thus, while summing the signal acquired from the cosine apodized beam with that of the Sinc beam will reduce the clutter received from Sine beam $\vec{T}_u(n, z_n)$ in the region of $|\theta| \ge \theta_\alpha$. The mainlobe of the Sine beam is also being spread as a result of the summing beam signals in the region of $-\theta_\alpha \le \theta \le \theta_\alpha$.

However, if the signal received from the cosine apodized beam is amplified by a factor of $\kappa$, then the location of the intersection between the cosine apodized beam and the DR beam, $\theta_i$, will be moved up and down along the mainlobe of the DR beam depending upon the gain factor κ. The larger the gain κ the closer $\theta_i$ is to the center of the main DR beam. When κ approaches zero, $|\theta_i|=\theta_\alpha$. If the magnitude of the signal from the segmented mainlobe of the DR beam is to compare with the amplified signal from the cosine apodized beam and κ being the amplification factor, the intersection point between $\kappa|\vec{T}_c|$ and $|\vec{T}_{uM}|$ will be located at $\pm\theta_{Dm}$, where $|\theta_{Dm}|\le\pi$. The higher the amplification factor κ the closer $\pm\theta_{Dm}$ is to the origin. Note that $2|\theta_{Dm}|$ is the spread of the mainlobe and the smaller the value $|\theta_{Dm}|$ the better the resolution. For example, the raised cosine or Hanning beam (e.g., a synthesized DR beam where the first sample beam is a Sine beam, the second or auxiliary sample beam is a cosine apodized beam, and the parameter α=1) is the Sinc beam combined with the cosine apodized beam. Accordingly, subtracting a component signal from the Hanning beam, that is computed by taking the minimum of the gain-raised (e.g., κ>1) cosine apodized beam and the Hanning beam gives a beam with sharpened mainlobe. The process is effectively creating a beam shaping function to sharpen the mainlobe of the Hanning beam. As the mainlobe of the Hanning beam is sharpened the sidelobe structure of the Hanning beam is also modified resulting in a new beam with very narrow mainlobe and very low sidelobe thereby improving both the detailed resolution and the contrast resolution of the image.

FIGS. 6J-6L illustrate XDR beam synthesis using a beam shaping function of embodiments. In providing a beam shaping function of embodiments, the mainlobe component of a beam for which XDR beam synthesis processing is to be provided (e.g., a first sample beam, a synthesized DR beam, a synthesized IDR beam, or a previous iteration synthesized XDR beam) is split into two components (e.g., a narrow mainlobe component and a residual mainlobe component) through operation of process 604 as illustrated in FIG. 6J. For example, $\vec{T}_{uM}$ is split into components $\vec{T}_{uM\_n}$ (the narrow mainlobe component) and $\vec{T}_{uM\_S}$ (the residual mainlobe component) using a beam shaping function, such as beam shaping function $\psi(\theta)$ of FIG. 6K, where $\vec{T}_{uM\_n}=\vec{T}_{DR}-\phi(\vec{T}_{DR})\text{MIN}\{|\vec{T}_{DR}|,\kappa|\vec{T}_c|\}$ and $\vec{T}_{uM\_S\_n}=\vec{T}_{uM}-\vec{T}_{uM\_n}$. An XDR beam may be synthesized at process 605 by weighted summing of the component signals as illustrated in FIG. 6L. For example, an XDR beam, $\vec{T}_{XDR}$, may be formed by combining a weighted (μ) narrow mainlobe component ($\vec{T}_{uM\_n}$), a weighted (ρ) residual mainlobe component ($\vec{T}_{uM\_S}$), and a weighted (γ) sidelobe component ($\vec{T}_S$), wherein the weighting factors (μ, ρ, and γ) may be selected based upon.

As the peak of the DR beam is aligned with the null the cosine apodized beam, the peak of the beam will not be altered by the process of $\vec{T}_{uM\_n}=\vec{T}_{DR}-\phi(\vec{T}_{DR})\text{MIN}\{|\vec{T}_{DR}|,\kappa|\vec{T}_c|\}$.

Thus be the peak of the signal $|\vec{T}_{uM\_n}|$ is theoretically equal to the peak of the signal $|\vec{T}_{DR}|$; or $\max(|I_{uM\_n}|)=\max(|\vec{T}_{DR}|)$. In implementation, numerical error in the apodization process may cause minute misalignment of the first sample beam and the second sample beam that may result in a reduction of amplitude in the process beam $|\vec{T}_{uM\_n}|$. A scale factor μ is introduced for gain equalization such that μ $\max(|\vec{T}_{uM\_n}|)=\max(|\vec{T}_{DR}|)$. At the first iteration, the signal $\vec{T}_{uM}$ corresponding to the mainlobe of the first sample beam (the Sinc beam) is decomposed into two components $\vec{T}_{uM\_1}$ and $\vec{T}_{uM\_S\_1}$. Since $I_{uM\_1}$ is a signal from a narrower beam than $\vec{T}_{uM}$ that is aligned with the $\vec{T}_{uM}$, and $\vec{T}_{uM\_1}$ is a signal component located away from the center of the beam for $\vec{T}_{uM\_1}$, a new mainlobe $\vec{T}_{uM\_S\_1}$ can be formed by combining the signals $\vec{T}_{uM\_1}$ and $\vec{T}_{uM\_S\_1}$; or $\vec{T}_{N\_uM\_1}=\vec{T}_{uM\_1}+\rho\vec{T}_{uM\_S\_1}$, where ρ≤1. When ρ=1, $\vec{T}_{N\_uM\_1}=\vec{T}_{uM}$, the mainlobe of the DR beam is not altered. When ρ<1 the new mainlobe $\vec{T}_{N\_uM\_1}$ is formed that the center of the lobe is narrow where as the outside skirt of the lobe is formed by the attenuated component signal of $\rho\vec{T}_{uM\_S\_1}$. Since the new mainlobe $\vec{T}_{N\_uM\_1}$ is created from components $\vec{T}_{uM\_1}$ and $\rho\vec{T}_{uM\_S\_1}$ that is decomposed from $\vec{T}_{uM}$, the lobes $\vec{T}_{N\_uM\_1}$ and $\vec{T}_{uM}$ spread in the same angular interval. The beam of signal $\vec{T}_{N\_uM\_1}$ spread contiguously connected to the sidelobe of the DR beam $\vec{T}_{\alpha S}$.

From the foregoing it can be appreciated that one may form a XDR beam by computing $\vec{T}_{XDR\_1}=\mu_1\vec{T}_{uM\_1}+\rho_1 I_{uM\_S\_1}+\gamma_1\vec{T}_{\alpha\_S}$. The XDR process can be iterated by feeding the XDR beam formed at the processor for n times until a satisfactory mainlobe is generated in the n-iterated XDR beam $\vec{T}_{XDR\_n}=\mu_n\vec{T}_{uM\_n}+\rho_n\vec{T}_{uM\_S\_n}+\vec{T}_{\alpha\_S}$. The scale parameters $\mu_n$'s in each iteration can be set to one by normalizing the parameters $\rho_n$ without a loss of generality. The parameters $\gamma_n$'s can be set differently in each iteration; however, $\gamma_n$'s may be also set equally to simplify the computation in all iterations. When the mainlobe of the XDR beam is split in each iteration, the magnitude of the signal at the skirt of the new mainlobe is attenuated according to the parameter $\rho_i$ to set the skirt level at $20 \log \rho_i$ db down from the new mainlobe.

FIGS. 6L(1)-6L(4) demonstrate how a XDR beam is formed in one iteration of the XDR process provided by processes 604 and 605 according to an embodiment of the invention. Parameters used for the processing example are set as the following: α=1; κ=2; μ=1; ρ=±0.125; and γ=0.015625. The signal $\vec{T}_{uM}$ corresponding to the mainlobe of the first sample beam (a Sinc beam) is segmented in the IDR process as shown in FIG. 6L(1). By raising the gain of the second sample beam (a cosine apodized beam) by setting κ=2, the signal $\vec{T}_{uM}$ is decomposed into two components: $\vec{T}_{uM\_1}$ and $\vec{T}_{uM\_S\_1}$, where $\vec{T}_{uM}=\vec{T}_{uM\_1}+I_{uM\_S\_1}$. These two signal components are then combined into $I_{N\_uM\_1}$, a signal corresponding to a new mainlobe that is composed with narrow mainlobe constructed by beam of $\vec{T}_{uM\_1}$ and an attenuated skirt of corresponding to lobes of $\vec{T}_{uM\_S\_1}$. The lobe attenuation coefficient ρ is set at 0.125 that implies the new mainlobe transitionally rolling-off, at 18 db down where the skirt is starting blended with the sidelobe. ρ can also be set at negative value to force the mainlobe to cross zero as shown in FIG. 6L(2). It has been found that negative first sidelobe enhances the border of the object resulting in improvement of tissue differentiation for some imaging application. The far sidelobe of the $\vec{T}_{XDR\_1}$ beam is blended with the segmented sidelobe of DR beam $\vec{T}_{\alpha S}$ that is attenuated by the factor γ=0.015625, or by 36 db. The XDR beam, the first sample beam (a Sinc beam or a DR beam for α=0, $\vec{T}_{DR,\alpha=0}$) and the DR beam $\vec{T}_{DR,\alpha=1}$ for α=1 are overlaid in FIG. 6L(3). FIG. 6L(4) plots the XDR beam in logarithmic scale. As demonstrated the mainlobe of the XDR beam is much narrower than the Sinc beam and the sidelobe level is substantially lower than the DR beam that is rolling of at 18 db/octave in the example. Operation of processes 604 and 605 may be repeated to progressively narrow the synthesized XDR beam mainlobe.

As with the IDR beam synthesized above, the mainlobe component segmented through operation of the above XDR process provides a narrow beam. However, embodiments of the invention operate to combine weighted residual mainlobe and sidelobe components (e.g., 0<ρ<1 and 0<γ<1) to provide desired rolloff and sidelobe level with respect to the XDR beam synthesized.

Figure 15D:
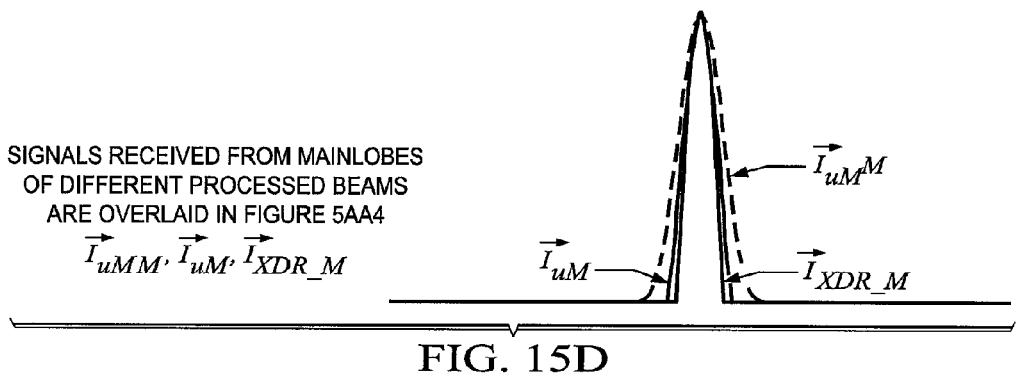
Figure 15E:
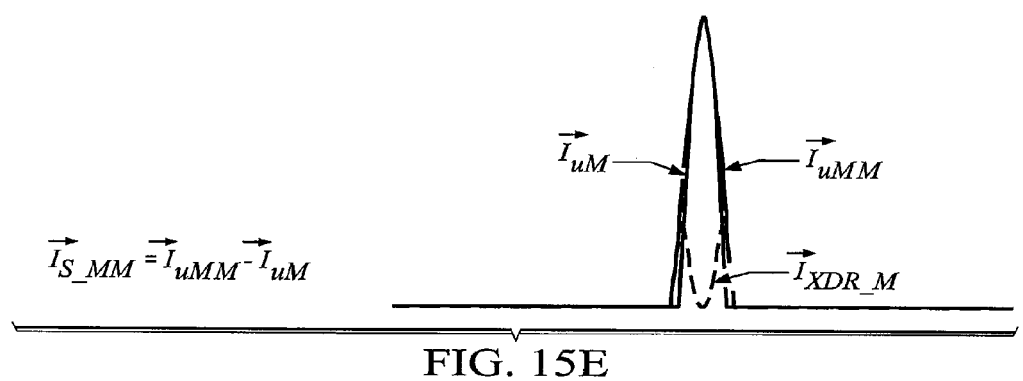
Figure 15F:
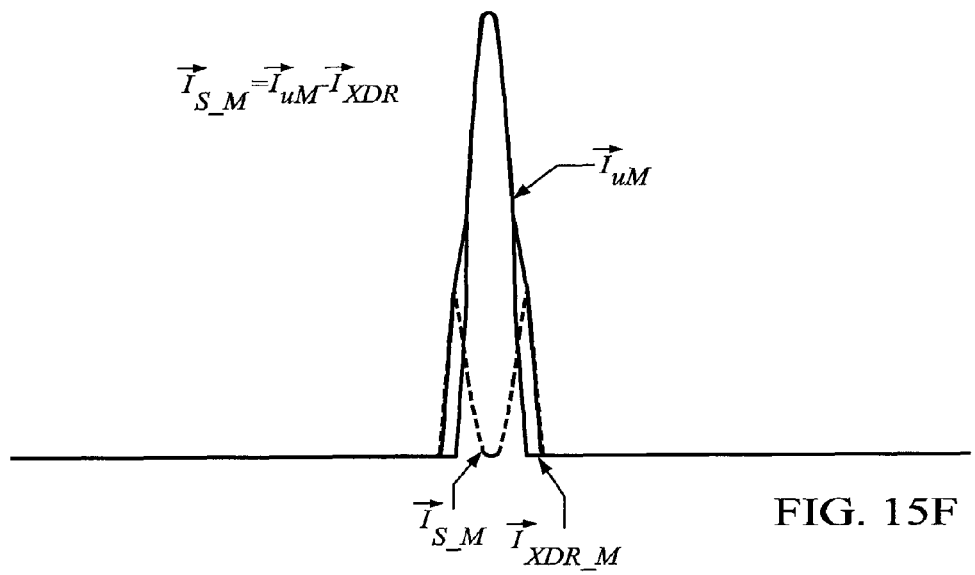
Figure 15G:
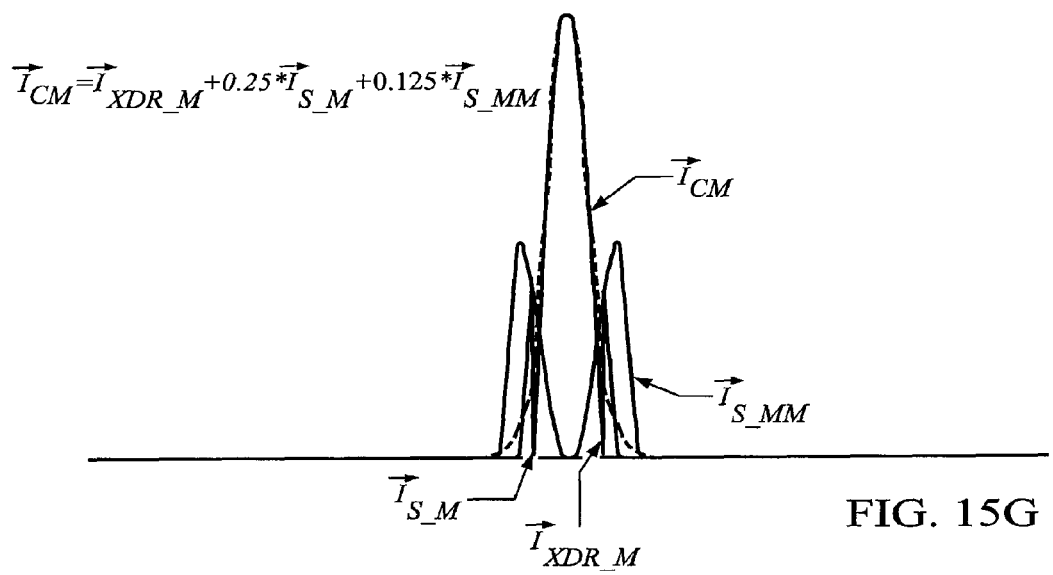

It should be appreciated that new component signals with different beam properties may also be generated by arithmetically combining different component signals that are segmented based on the principles herein. For example, the segmented component signal $\vec{M}$ as shown in FIG. 6D may be combined with a component signal $\vec{P}$ that is created according to $\vec{P}=\phi(\vec{T}_{DR,\alpha=0})\min(|\vec{T}_{DR,\alpha=0}|,|\vec{T}_{DR,\alpha=1}|)$ to obtain a new component signal $\vec{T}_{uMM}$ where $\vec{T}_{uMM}=\vec{M}+\vec{P}$. $\vec{T}_{uMM}$ is a component signal corresponding to a mainlobe spread less than the Hamming mainlobe but more than those from other segmented mainlobes such as $\vec{T}_{uM}$, $\vec{T}_{\alpha M}$ for all α's and those signals from the mainlobe of any $\vec{T}_{XDR}$ beam, $\vec{T}_{XDR\_M}$. This process is graphically depicted in FIGS. 15A-15C. Three component signals $\vec{T}_{uMM}$, $\vec{T}_{uM}$, $\vec{T}_{XDR\_M}$, each acquired from a segmented mainlobe of different beamwidths where $\vec{T}_{uMM} > \vec{T}_{uM} > \vec{T}_{XDR\_M}$, are overlaid in FIG. 15D. Taking the difference between signals $\vec{T}_{uMM}$ and $\vec{T}_{uM}$ to obtain a signal $I_{S\_MM}$ which represents the signal acquired from a sidelobe component beam as shown in FIG. 15E. Similarly, a signal $\vec{T}_{S\_M}$ can be segmented by taking the difference between signals $\vec{T}_{uM}$ and $\vec{T}_{XDR\_M}$ that represents a signal acquired from a sidelobe component beam as shown in FIG. 15E. Sidelobe component signals $\vec{T}_{S\_M}$, $\vec{T}_{S\_MM}$ may be scaled and combined with $\vec{T}_{XDR\_M}$ to obtain a new signal which is equivalent to the one is acquired from a shaped mainlobe. For example, the beam corresponding to the signal $\vec{T}_{CM}=\vec{T}_{XDR\_M}+0.25\vec{T}_{S\_M}+0.125\vec{T}_{S\_M}$ is shown in FIG. 15G. The shaped mainlobe $\vec{T}_{CM}$ can be combined with other sidelobe components signals with desired roll-off to obtain a signal of the desired beam.

Figure 7A:
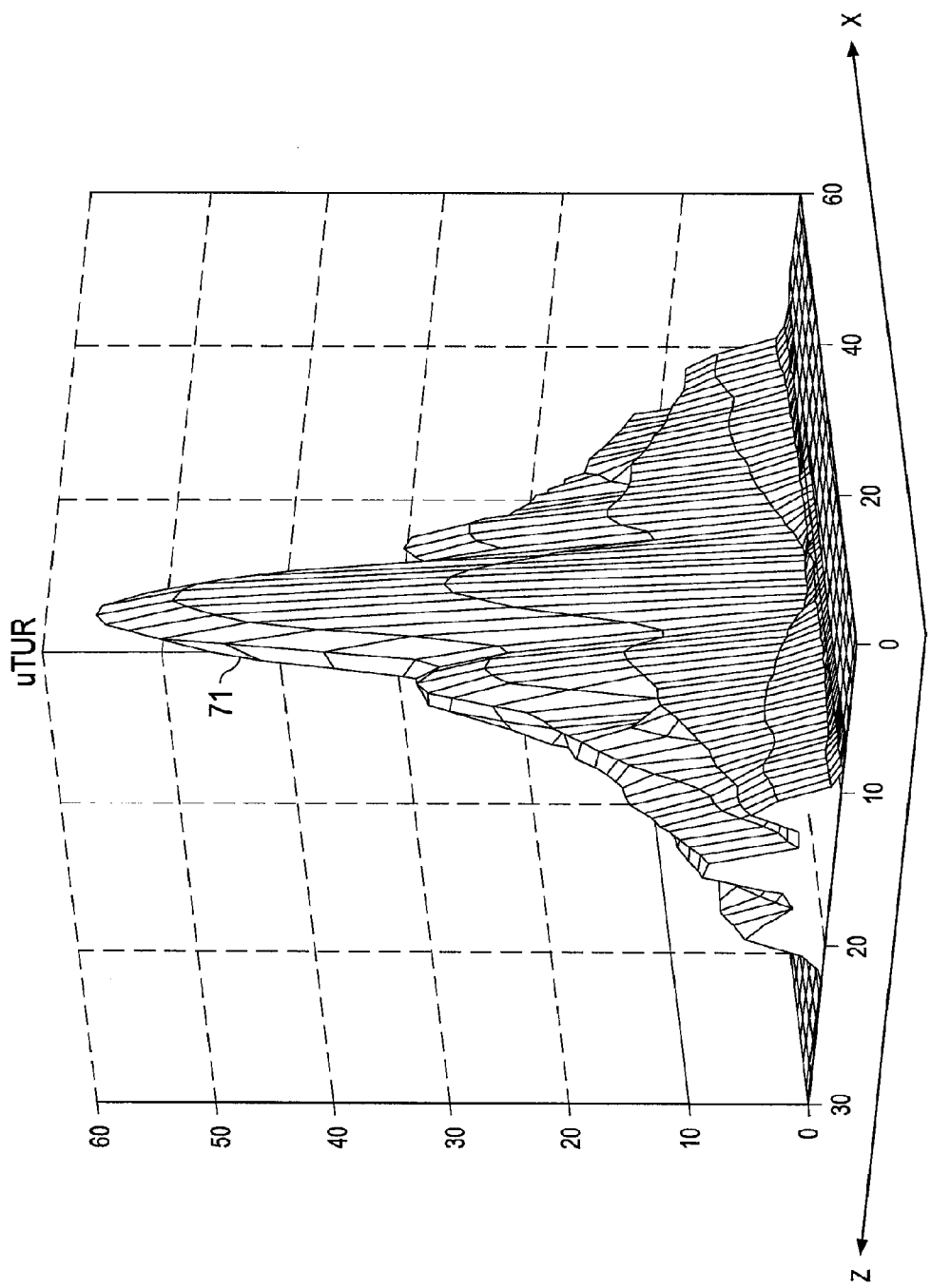
FIGS. 7A-7C graphs of exemplary sample beams and an enhanced dynamic resolution beam synthesized therefrom according embodiments of the present invention.
Figure 7B:
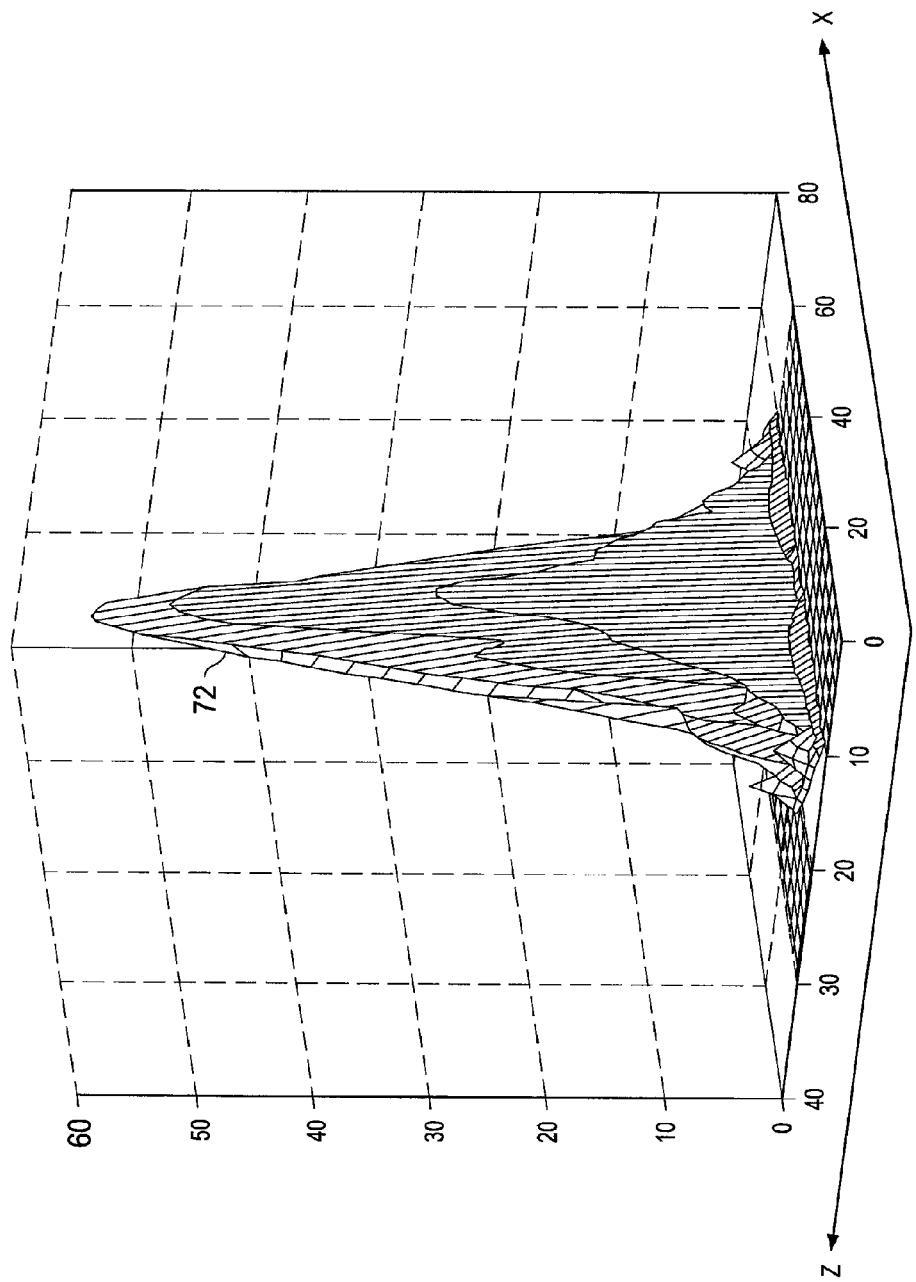
Figure 7C:
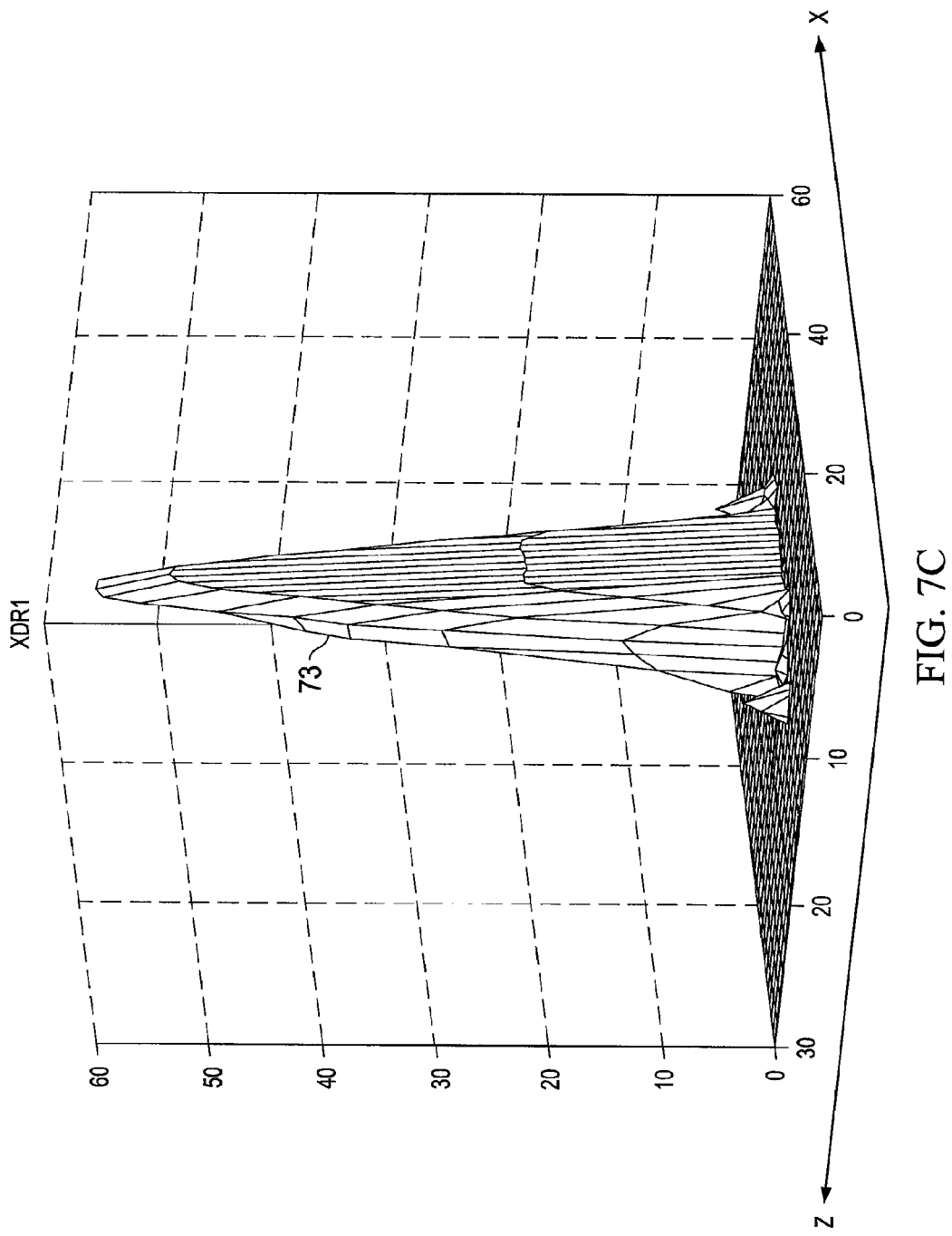

The DR, IDR and XDR signal segmentation techniques of embodiments of the present invention are based on synthesis and decomposition of component beams according to the narrow band geometrical and morphological properties among the Sine beam, the cosine apodized beam, the Hanning beam, and other beams. However, it can be shown that the concepts herein are similarly effective when a broadband signal is beamformed and processed as for general imaging application. FIGS. 7A-7C show graphs of exemplary spatiotemporal profiles of the sample beams and an XDR beam synthesized therefrom according the concepts described above to illustrate the results of beam synthesis of the present invention. An array of 32 transducer elements are excited by Gaussian pulses centered at 3.5 MHz with 2 MHz of bandwidth. Applying proper time delay and different weights to the signals received by each element to focus a point at 60 mm, the point is spread differently depending upon the properties of the beam. Sample beam 71 of FIG. 7A comprises an unapodized first sample beam (e.g., a Sinc beam), second or auxiliary sample beam 72 of FIG. 7B comprises an apodized beam (e.g., a Hanning beam or raised-cosine apodized beam), and XDR beam 73 is synthesized using the first sample beam and second or auxiliary sample beam according to the concepts of this invention. FIG. 7C shows that resulting mainlobe of XDR beam 73 is more narrow than the mainlobe of sample beam 71 of FIG. 7A with little or no sidelobes. Likewise, the mainlobe of XDR beam 73 of FIG. 7C is more narrow than the mainlobe of sample beam 72 of FIG. 7B (the apodized beam).

FIG. 8 further illustrates an example of the concepts of the invention applied to one dimensional processing. Graph 800 shows Sinc beam 801, Hanning beam 802 and synthesized beam 803 produced by the concepts taught herein. Specifically, graph 800 is a Fourier spectrum showing spectral components of a signal comprising ten sinusoids a0 to a9 spread from normalized frequencies from −0.35 to 0.25. The dynamic range of these signals is 140 dB with signal a3 at 0 dB and signal a7 at minus 140 dB. Uniformly distributed noises at minus 133 dB are added to the test signal and below this noise level. As can be seen, if the Fourier transform is taken on the test signal without using a window function, only the strong spectral components a1, a2, a3, a4 and a5 are resolved. The other signals a6, a7, a8, a9 and a0 are corrupted by the composite sidelobes of these strong components. The spectral peak of each spectral component represents the mainlobe of a sine function whose sidelobe is rolling off at a rate of 6dB per octave. The sidelobes of the strong components swamp the frequency and do not allow the detection of a0, a9, a8, a6, and a7. When the signal is Hanning apodized, the overall sidelobe level is lower that is rolling off at a faster rate or 18dB per octave. As a result, additional signal of a6 is resolved. However, as shown by Hanning beam 802, the main beam is spread and spectral components a7, a8, a9 and a0 are yet un-resolved.

Cosine apodized Fourier spectrum may be obtained by replacing each spectral component by the average of its two most adjacent neighbor spectral components. Using an unapodized component and a cosine apodized component, the DR/IDR/XDR spectrum can be calculated. The clutter cancellation parameter α is calculated for every spectral component in the Fourier spectrum. The sidelobe of every spectral component are then suppressed from the DR process, followed by setting μ=1, γ=1, ρ=1, and κ=2 in the XDR process of embodiments. As shown by synthesized beam 803, all spectral components are resolved, including those components whose levels are embedded in the noises: a7, a8 and a0.

FIG. 9 shows Sinc beam 905, Hanning beam 906, DR beam 901, XDR1 beam 902, XDR2 beam 903, and XDR3 beam 904 processed using different sets of parameters. Sinc beam 905 is not apodized, and Hanning beam 906 is apodized. DR beam 901 results by using only the DR processing, as discussed above. By using the XDR process discussed herein, XDR1 beam 902, XDR2 beam 903, and XDR3 beam 904 can be produced.

FIG. 10 shows Sinc beam 1001, Hanning beam 1002, and cosine apodized beam 1003. Note that the cosine apodized beam is used as a steering beam to control the power level. The cosine apodized beam is used to move the gain up and down, so as to detect where the system should cut the Sine beam. The minimum of the Sinc beam and the cosine apodized beam will determine where the main beam crosses the zero axes.

From the foregoing it can be appreciated that operation of the XDR beam synthesis process further narrows the mainlobe of an ultrasound beam and/or the sidelobes are further reduced, such as through application of nonlinear and linear signal processing in which the DR beam signal is decomposed into different component signals. These component signals may then be used to synthesize a new beam signal (an XDR beam signal) that corresponds to a virtual beam of which the mainlobe is narrow and the sidelobe is low. Alternatively, XDR beams of embodiments may be synthesized by essentially not forming the aforementioned DR beam but rather proceeding directly to the XDR process of FIG. 6, such as by maintaining α at a constant (e.g., 1 or 0.5).

It should be appreciated that the foregoing DR/IDR/XDR beam synthesis techniques may be implemented in a number of different imaging techniques. For example, DR/IDR/XDR beam synthesis techniques may be implemented with respect to linear scan conversion, spatial compounding, etc. For multi-beam spatial compounding, the detected signals from spatially displaced beams may be integrated to reduce the coherent speckle. To enhance the resolution, a unapodized beam and a Hanning beam can be simultaneously formed to obtain a DR/IDR/XDR signal from each look direction prior to compounding process is taken place.

Although embodiments have been described above with reference to one dimensional transducer arrays, it should be appreciated that the concepts of the present invention are applicable to multidimensional transducer arrays. For example, the concept of DR/IDR/XDR beam synthesizing can be directly applied to two dimensional (2D) beamforming.

Having described providing DR, IDR, and XDR beam synthesis according to embodiments of the invention above, detail with respect to various functions and implementations of DR, IDR, and XDR beam synthesis will be provided below. It should be appreciated that the functions and implementations set forth below may be utilized in the systems and methods described above to provide DR, IDR, and/or XDR beam synthesis according to embodiments of the invention.

Beam Decomposition and DR/IDR/XDR Beam Synthesis

In operation according to embodiments of the invention the signal acquired from a DR beam at a particular location can be computed by minimizing the power of the formed beam in each look direction. Since the power of a beam changes at each beam location, the mainlobe width and sidelobe level of a DR beam is optimized according to the power minimization criteria according to embodiments of the invention. Based on geometrical and morphological properties of the DR beam, the first and second sample beams, signals corresponding to different component mainlobe and sidelobe beams can be segmented. These component beams are further decomposed and new beams with desired properties are then synthesized by arithmetically manipulated these component beams. Signal corresponding to each new beam are computed according to the DR, IDR and XDR beam decomposition and synthesis process of embodiment of the invention. The processes of constructing the signal corresponding to a synthesized beam with desired properties using the decomposed component beams are implemented according to embodiments of the invention in process 601, 602, 603, 604 and 605 of FIG. 6. These processes are graphically depicted in great detail using signals in combination of the first sample beam, the second sample beam, the un-apodized beam (α=0), the Hanning apodized beam (α=1), the DR beam of other α's (0<α<1) as shown in FIGS. 3A, 6A-6L(4), and 15A-15G.

The beam decomposition and synthesis processes of embodiments of the invention may be implemented in software and/or hardware configurations. Such beam decomposition and synthesis processes can be either implemented before QBP (quadrature band passed) filtering or post QBP filtering as shown in FIGS. 5A and 5B. Methods based on FIG. 5B are preferred since the process is more robust in presence of noises after the signals acquired from the first and the second beams are filtered by the QBP filter.

Beam decomposition, as described herein, may be utilized in dynamic resolution beam synthesis according to embodiments of the invention. In a further, more detailed, example of sample beam decomposition and synthesis in accordance with embodiments of the invention, let $I_u$ and $I_c$ be two acquired sample signals (e.g., echo from distribution of scatterers $O(\phi)$) received by using Sinc beam $B_u$ and cosine apodized beam $B_c$ that are spread angularly in $\phi$. Since the amplitude of the received signals are an integration of all echoes from the insonified scatterers that are weighted by the amplitude of each beam at every angular directions, these sample signals may be represented as $I_u(z,\theta)=\int O(z,\theta-\phi)B_u(z,\phi)d\phi$ and $I_c(z,\theta)=\int O(z,\theta-\phi)B_c(z,\phi)d\phi$; thus the signal from a new beam $B_\alpha$ can be computed by summing signals $I_u$ and $I_c$ according to the following equation. $I_\alpha(z,\theta)=\int O(z,\theta-\phi)(B_u(z,\phi)+\alpha B_c(z,\phi))d\phi=I_u(z,\theta)+\alpha I_c(z,\theta)$; where $B_\alpha=B_u+\alpha B_c$.

As discussed above, signals received from the cosine apodized beam can be combined with the signal received from the Sine beam to obtain a new signal. This new signal is effectively received from a new beam of reduced sidelobe level by making the trade of broadening its mainlobe. For example, let $\vec{I}_\alpha=\vec{I}_u+\alpha \vec{I}_c$. With respect to the signal $\vec{I}_\alpha$, the geometrical and the morphological properties of its corresponding beam $B_\alpha$ vary with the parameter α. Generally, the mainlobe is monotonically broadening with the parameter α while the sidelobe level is monotonically reduced and the sidelobe roll-off rate is monotonically increased when a is greater or equal to zero and smaller or equal to one, $0 \leq \alpha \leq 1$.

Figure 16A:
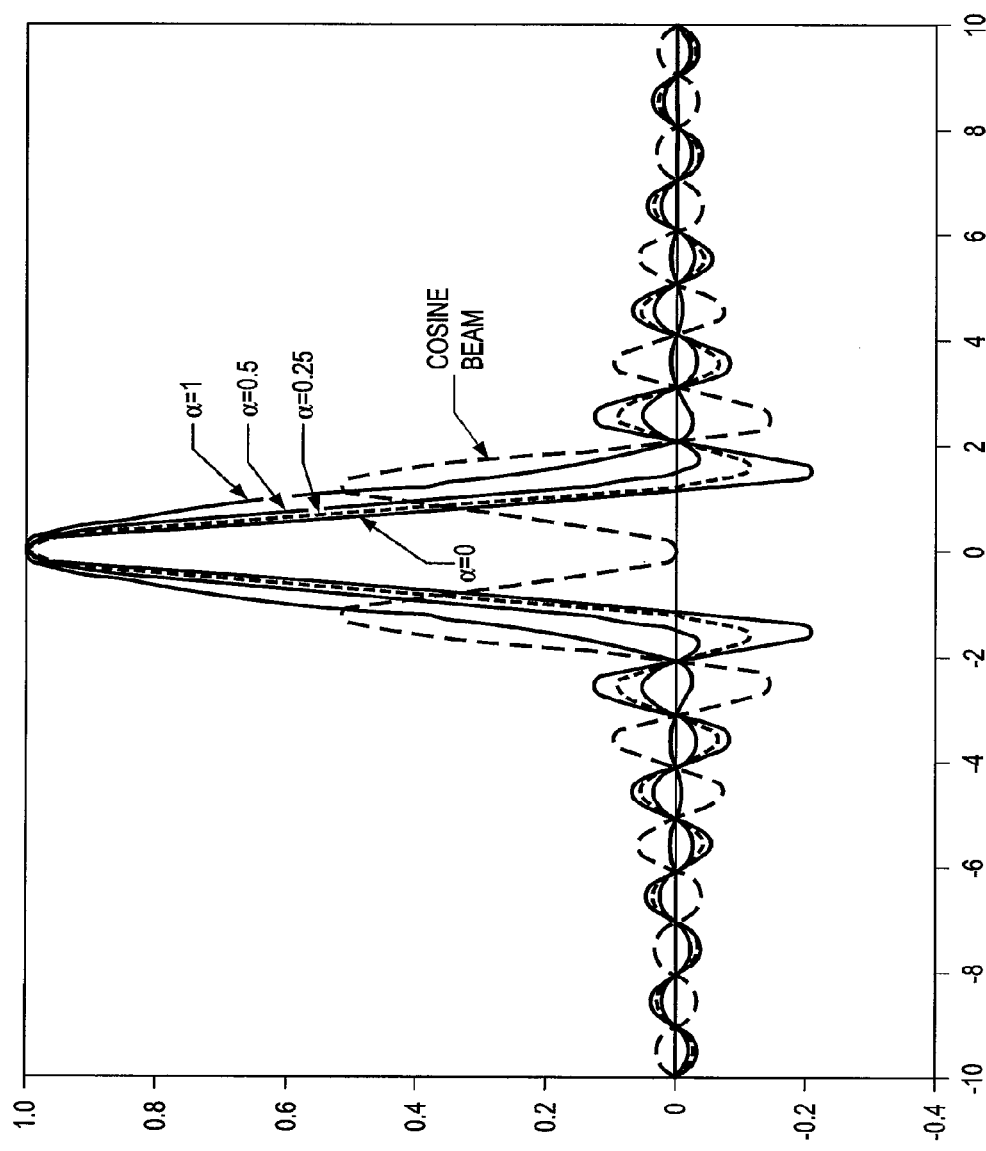
FIGS. 16A-16E show beams utilized in beam decomposition and synthesis according to embodiments of the invention.
Figure 16B:
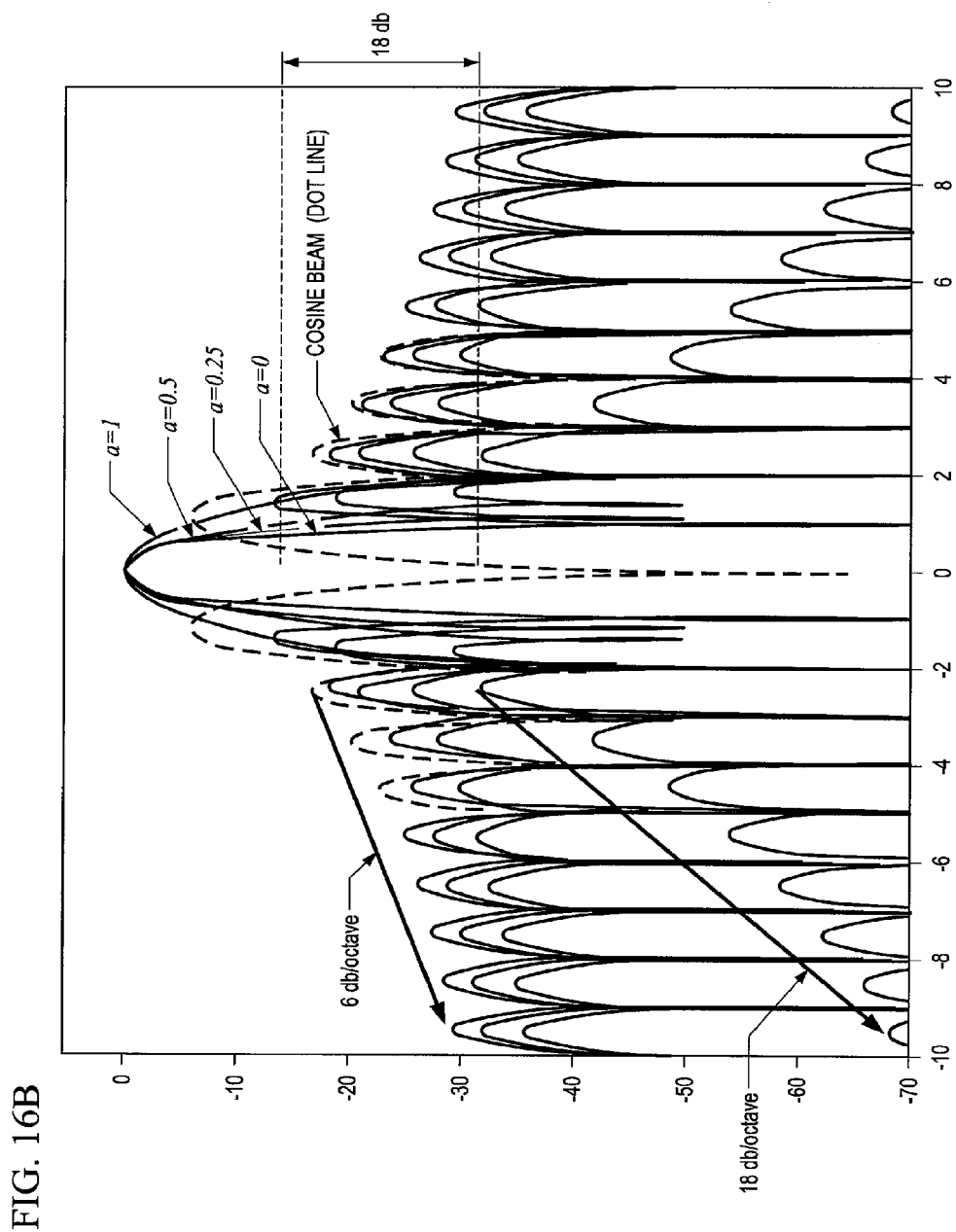

The beam properties for different values of α (0,0.25,0.5, 1) are depicted using FIGS. 16A and 16B. When α=1, $\vec{I}_\alpha = \vec{I}_1 = \vec{I}_u + \vec{I}_c$; where $\vec{I}_1$ is the Hanning beam (raised cosine apodized beam). When α=0, $\vec{I}_\alpha = \vec{I}_0 = \vec{I}_u$; where $\vec{I}_0$ is the Sinc beam. In the Hanning beam, the first sidelobe is −18 db lower than the first sidelobe of the Sinc beam. The Hanning sidelobe is rolling off at a faster rate at 18 db/octave versus the sine sidelobe that is rolling off at a rate of 6 db/octave. However, the mainlobe of the Hanning beam would be 50% broader than that of the Sinc beam.

Figure 16C:
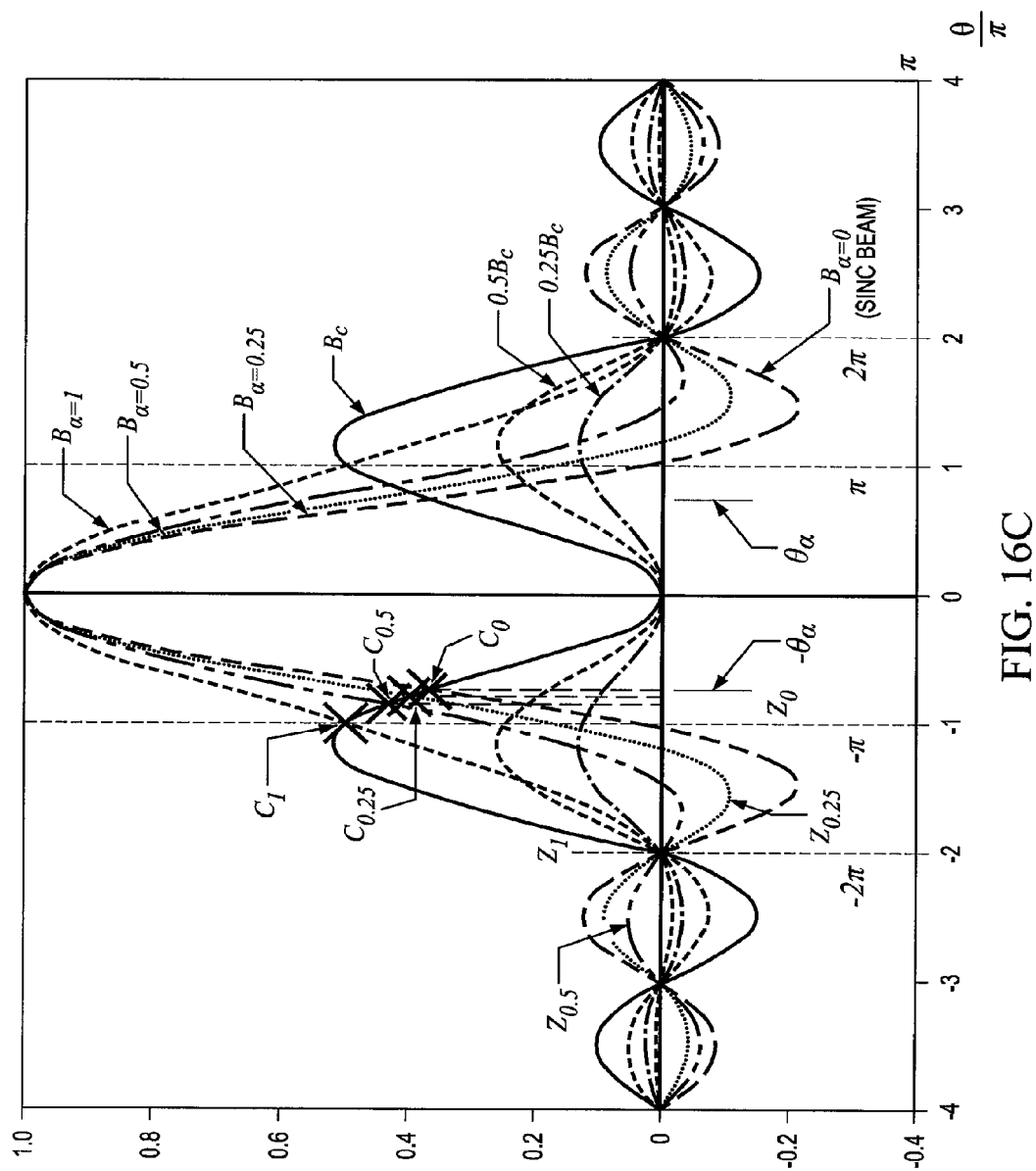

It should be appreciated that the Sine beam and the cosine apodized beam oscillate in opposite phases when $\theta > \pm \pi$ as shown in FIG. 16C. Thus, in the process of $B_\alpha = B_u + \alpha B_c$ at angular locations greater than $\pm \pi$, cancellation in magnitude of the sidelobes of the Sine beam occurs in all angular locations at $> \pm \pi$. However, at the angular location $\pm \pi < \theta \leq \pm 2\pi$ where the first sidelobe of the Sine beam is located, the sidelobe cancellation process results in shifting the zero crossing point and spreading the mainlobe of the $B_\alpha$ beam.

Also shown in FIG. 16C, the first zero crossing of the Sinc beam is located at $\pm \pi$, thus $\vec{I}_u(\pm \pi)=0$. When a beam $B_\alpha$ is formed according to $B_\alpha = B_u + \alpha B_c$ to obtain the signal $\vec{I}_\alpha$, since there is no contribution from the Sinc beam at location ±π to the formation of the $B_\alpha$ beam, the magnitude of the $\vec{T}_\alpha$ beam at ±π will be equal to the magnitude of the cosine apodized beam that is scaled by α, or $\vec{T}_\alpha(\pm\pi)=\alpha \vec{T}_c(\pm\pi)$. At the beam pointing direction, the gain of the $B_\alpha$ beam is maximized whereas the gain of the cosine apodized beam $B_c$ is minimized, or $B_\alpha(0)=B_{\alpha\ max}$, $B_c(0)=0$ for any α. The gain of beam $B_\alpha$ is always greater than the gain of $\alpha B_c$ at the angular location θ<±π for any α. When 0≤α≤1, $|\alpha B_c| \leq |B_c|$ thus, $\alpha|\vec{T}_c| \leq |\vec{T}_c|$. Therefore, if the minimum of signals between $|\vec{T}_\alpha|$ and $|\vec{T}_c|$ are taken, $$M_{n\_\alpha} = \min\{|\vec{I}_\alpha|, |\vec{I}_c|\} = \begin{cases} |\vec{I}_c|, & \text{for } |\theta| \leq \theta_\alpha \\ |\vec{I}_\alpha|, & \text{for } |\theta| > \theta_\alpha \end{cases};$$

where $M_{n\_\alpha}$ is the signal received from the minimum beam that is formed by taking the absolute minimum gain at all angles θ between two beams $B_\alpha$ and $B_c$; $\theta_\alpha$ is the angle where beams $B_c$ and $B_\alpha$ are intersected and $\theta_\alpha \leq \pi$. $C_0$, $C_{0.25}$, $C_{0.5}$, $C_1$ shown in FIG. 16C are the intersection points between beams $B_c$ and $B_\alpha$; $Z_0$, $Z_{0.25}$, $Z_{0.5}$, $Z_1$ are the zero crossing points of beam $B_\alpha$'s for α=0, α=0.25, α=0.5, and α=1 respectively. Notice that as α increases from zero to one, the zero crossing progressively moves from ±π to ±2π. The mainlobe of beam $B_\alpha$'s is spreading as the parameter α increases while the sidelobe level decreases.

Setting the phase $\phi(\vec{M}_{n\_\alpha})$ of the signal $\vec{M}_{n\_\alpha}$ the same as the phase of the signal received from the beam $B_\alpha$, or $\phi(\vec{M}_{n\_\alpha})=\phi(\vec{T}_\alpha)$, then $$\vec{M}_{n\_\alpha} = \varphi(\vec{I}_\alpha)\min\{|\vec{I}_\alpha|, |\vec{I}_c|\} = \begin{cases} \varphi(\vec{I}_\alpha)|\vec{I}_c|, & \text{for } |\theta| \leq \theta_\alpha \\ \varphi(\vec{I}_\alpha)|\vec{I}_\alpha|, & \text{for } |\theta| > \theta_\alpha \end{cases}; \quad (1)$$

where $\phi(\vec{T}_\alpha)$ is the phase of the signal $\vec{T}_\alpha$.

Since beams $B_\alpha$ and $B_c$ are intersected at $\theta_\alpha$, thus $B_\alpha(\theta_\alpha)=B_c(\theta_\alpha)$. Also, at the beam pointing direction, $B_\alpha(0)=B_{\alpha\ max}$ and $B_c(0)=0$. When $\vec{M}_{n\_\alpha}$ is subtracted from $\vec{T}_\alpha$ to obtain a new signal $\vec{T}_{am\_n\_\alpha}$ or $$\vec{I}_{am\_n\_\alpha} = \vec{I}_\alpha - \vec{M}_{n\_\alpha} = \begin{cases} \varphi(\vec{I}_\alpha)(|\vec{I}_\alpha|-|\vec{I}_c|), & \text{for } |\theta| < \theta_\alpha \\ 0, & \text{for } |\theta| \geq \theta_\alpha \end{cases}; \quad (2)$$

for $0 \leq \alpha \leq 1$.

$\vec{T}_{am\_n\_\alpha}$ is a signal whose amplitude is maximized at θ=0; The magnitude of $\vec{T}_{am\_n\_\alpha}$ spreads from its peak symmetrically toward zero at $\pm\theta_\alpha$. The operation of $\vec{T}_\alpha = \vec{T}_{am\_n\_\alpha} + \vec{M}_{n\_\alpha}$ implies that signal $\vec{T}_\alpha$ is decomposed into two components: $\vec{T}_{am\_n\_\alpha}$ and $\vec{M}_{n\_\alpha}$. Component signal represents a signal corresponding to a component beam $\Psi_{am\_n\_\alpha}$ which is bound in a region of $-\theta_\alpha \leq \theta \leq \theta_\alpha$. The peak of signal $\vec{T}_{am\_n\_\alpha}$ is aligned with the peak of $\vec{T}_\alpha$. Component signal $\vec{M}_{n\_\alpha}$ is a residue signal of $\vec{T}_\alpha$ which corresponds to a component beam $\Psi_{as\_n\_\alpha}$ that retains the sidelobe structure of beam $B_\alpha$ in the regions of $\theta < -\theta_\alpha$ and $\theta > \theta_\alpha$.

The mainlobe of the Sinc beam is angularly bounded in the region of $-\pi \leq \theta \leq \pi$. Since $\theta_\alpha \leq |\pi|$, the beam width of component beam $\Psi_{am\_n\_\alpha}$ (signal $\vec{T}_{am\_n\_\alpha}$) is narrower than that of the Sinc beam. Further, $\Psi_{am\_n\_0}(0)=B_u(0)$, the maximum gain of beam $\Psi_{am\_n\_0}$ and its pointing direction is also not altered.

Figure 16D:
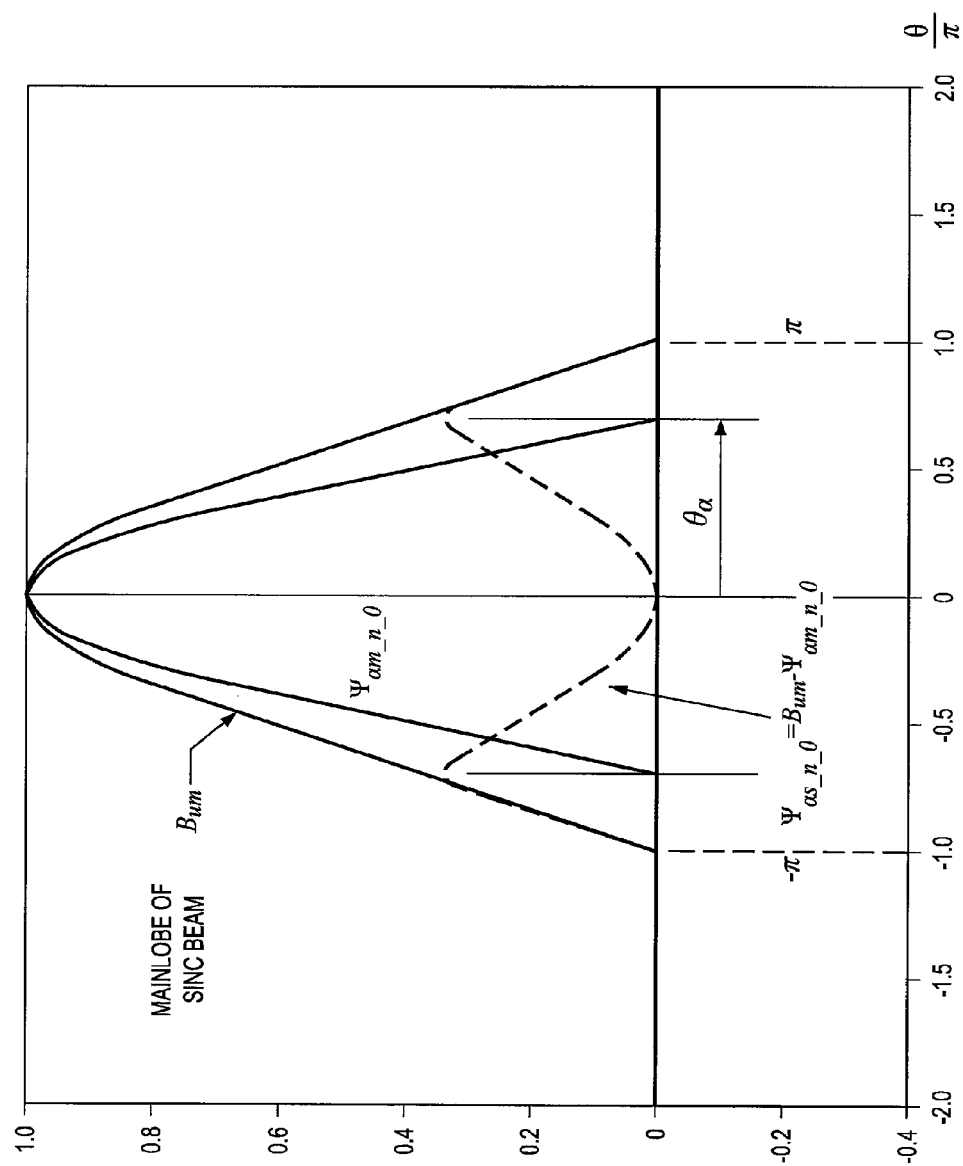

The mainlobe of the Sinc beam $B_{uM}$ and the beam $\Psi_{am\_n\_\alpha=0}=\Psi_{am\_n\_0}$ are overlaid in FIG. 16D. A new component beam $\Psi_{as\_n\_0}$ can be decomposed from the mainlobe of the Sinc beam $B_{um}$ according to $\Psi_{as\_n\_0}=B_{um}-\Psi_{am\_n\_0}$. $\Psi_{as\_n\_0}$ is a residual mainlobe beam that consists of dual lobes whose peak is aligned with the nulls of the component beam $\Psi_{am\_n\_0}$. By minimizing the amplitude or the power of the signal received by the component beam $\Psi_{am\_n\_0}$, the resolution would be asymptotically approaching to beam $\Psi_{am\_n\_0}$.

Figure 16E:
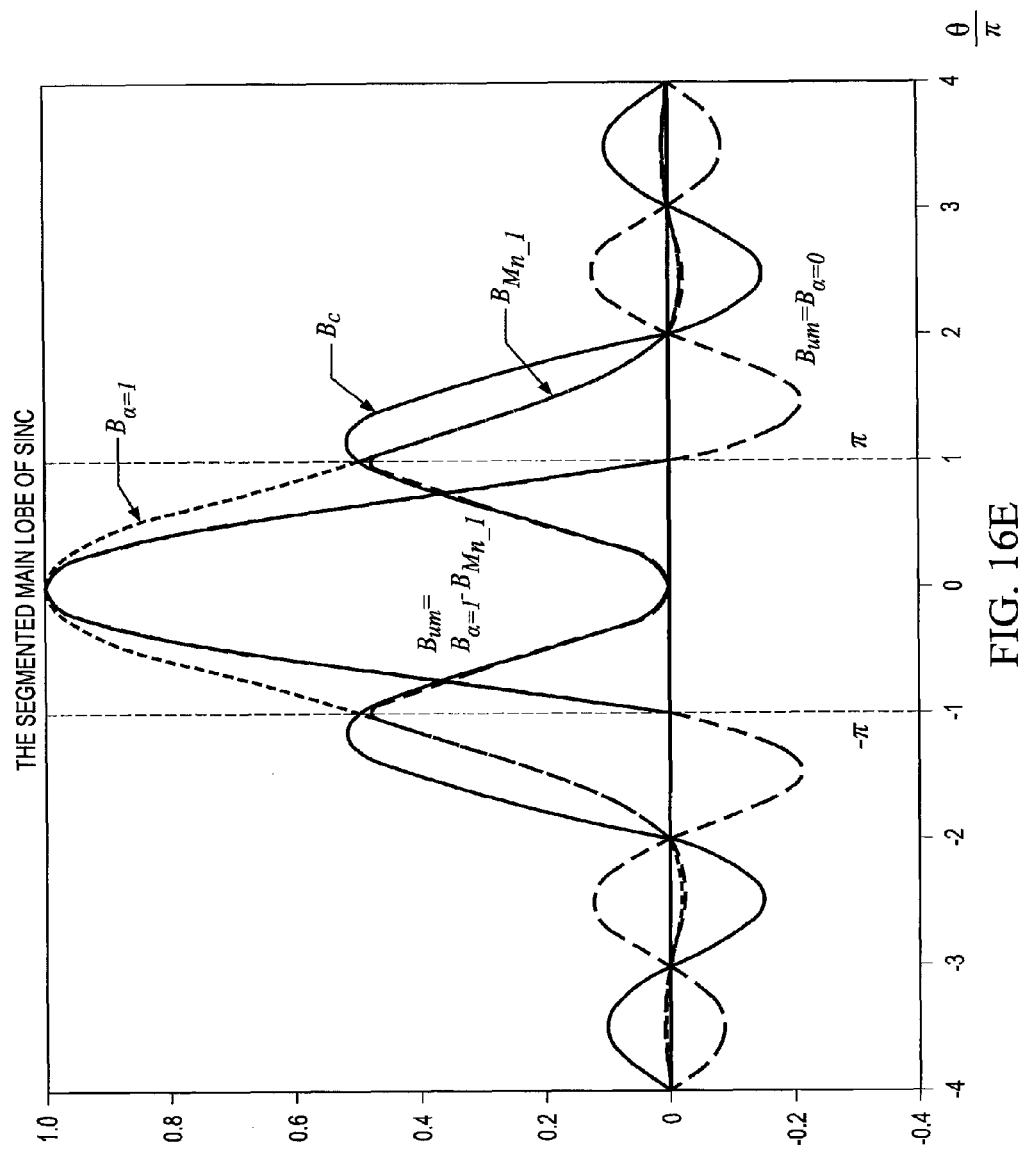

It should be appreciated that the mainlobe of the Sinc beam may be segmented according to the following process. FIG. 16E shows that beams $B_u$ and $B_c$ are summed to form beam $B_{\alpha=1}$, the Hanning beam. Since $B_u(\pi)=0$, and $B_{\alpha=1}(\pi)=B_c(\pi)=0$. Thus a beam $$B_{M_{n\_1}}$$

can be created by taking the minimum between the amplitudes of beams $B_{\alpha=1}$ and $B_c$. By assigning the phase of beam $$B_{M_{n\_1}}$$

the same as the phase of beam $B_{\alpha=1}$, the magnitude of the beam $$B_{M_{n\_1}}$$

will be the same as that of $B_c$ when $\theta \leq \pi$. In the region of $\theta > \pi$, the magnitude of $$B_{M_{n\_1}}$$

will be the same as that of beam $B_{\alpha=1}$. Thus the mainlobe of the Sinc beam $B_{um}$ may then be segmented by $$B_{um} = B_{\alpha=1} - B_{M_{n\_1}} \square \Psi_{am\_n\_1},$$

and the sidelobe of the Sinc beam can be segmented by removing the mainlobe $B_{um}$ from the Sinc beam $B_u$ by $B_{us}=B_u-B_{um}=B_u-\Psi_{am\_n\_1}$.

The signals from these beams are effectively computed according to the following process. Setting the parameter α to one: α=1, then $\vec{T}_1=\vec{T}_u+\vec{T}_c$. Since $\vec{T}_u(\pm\pi)=0$ thus, $|\vec{T}_c|=|\vec{T}_u+\vec{T}_c|$ for $|\theta|=\pi$. Thus $$M_{n\_1} = \varphi(\vec{I}_1)\min\{|\vec{I}_1|, |\vec{I}_c|\} = \begin{cases} \varphi(\vec{I}_1)|\vec{I}_c|; \text{ for } |\theta| < \pi \\ \varphi(\vec{I}_1)|\vec{I}_c| = \varphi(\vec{I}_1)|\vec{I}_u + \vec{I}_c|; |\theta| = \pi \\ \varphi(\vec{I}_1)|\vec{I}_u + \vec{I}_c|, \text{ for } |\theta| > \pi \end{cases}$$

The phase of $$M_{n\_1}$$

is set to be the same as the vector $\vec{I}_1$ by letting $$\vec{M}_{n\_1} = \varphi(\vec{I}_1) M_{n\_1}.$$

A null will be placed at $\theta = \pm\pi$ when the amount of signal from beam $\vec{M}_{n\_1}$ is removed from the signal of $\vec{I}_1$ in the subtraction process of $\vec{I}_1 - \vec{M}_{n\_1}$. Since the width of the mainlobe of the Sinc beam is defined by the angular region between $-\pi$ and $+\pi$, the mainlobe of the Sinc beam thus is segmented: $\vec{I}_{uM} = \vec{I}_1 - \vec{M}_{n\_1}$.

The sidelobes of the Sinc beam can thus be obtained by $\vec{I}_{uS} = \vec{I}_u - \vec{I}_{uM}$; and the sidelobes of $\vec{I}_\alpha$ can be obtained by $\vec{I}_{\alpha S} = \vec{I}_\alpha - \vec{I}_{uM}$. Since the DR i signal is the signal received from different beams at different sample locations with minimal clutter power using different $\alpha$, or $\vec{I}_{DR\_i} = \vec{I}_\alpha$. Given $\vec{I}_{\alpha S}$ and $\vec{I}_{uM}$, a DR beam of embodiments of the invention can be synthesized by summing the mainlobe $\vec{I}_{uM}$ with different amounts of $\vec{I}_{\alpha S}$ such that $\vec{I}_{DR} = \vec{I}_{uM} + \gamma \vec{I}_{\alpha S}$; where $\gamma \leq 1$.

The result shows that the beam width of the synthesized DR beam associated with the DR beam signal $\vec{I}_{DR}$ is the same as the diffraction limited Sinc beam whereas the sidelobe of the synthesized DR beam associated with the DR beam signal $\gamma \vec{I}_{\alpha S}$ is lower than the Sinc beam and the sidelobe of the minimum power beam $\vec{I}_\alpha$ for all signals in an image.

The signal $\vec{I}_{DR}$ from the DR beam, comprises two component signals, a component signal from the sidelobe $\vec{I}_{\alpha S}$ or the reduced sidelobe $\gamma \vec{I}_{\alpha S}$, and a component signal received from the mainlobe. Keeping the signal from the sidelobe $\vec{I}_{\alpha S}$ (or $\gamma \vec{I}_{\alpha S}$) unchanged, the component signal from segmented main beam $|\vec{I}_{uM}|$ may be further split into component signals that include at least one component corresponding to a new mainlobe $\vec{I}_{uM\_m}$ whose beam width is much narrower than that of from $|\vec{I}_{uM}|$; and other components decomposed from the residue signals into new sidelobes that are split from the mainlobe of $\vec{I}_{uM}$. Beams from the desired direction form a mainlobe where signal $\vec{I}_{uM}$ is received. From the same direction, practically no signals can be received from $\vec{I}_c$ due to the location of the null in the cosine apodized beam. In other words, essentially no signal is present in $\vec{I}_c$ from the desired direction (e.g., look direction).

Figure 11:
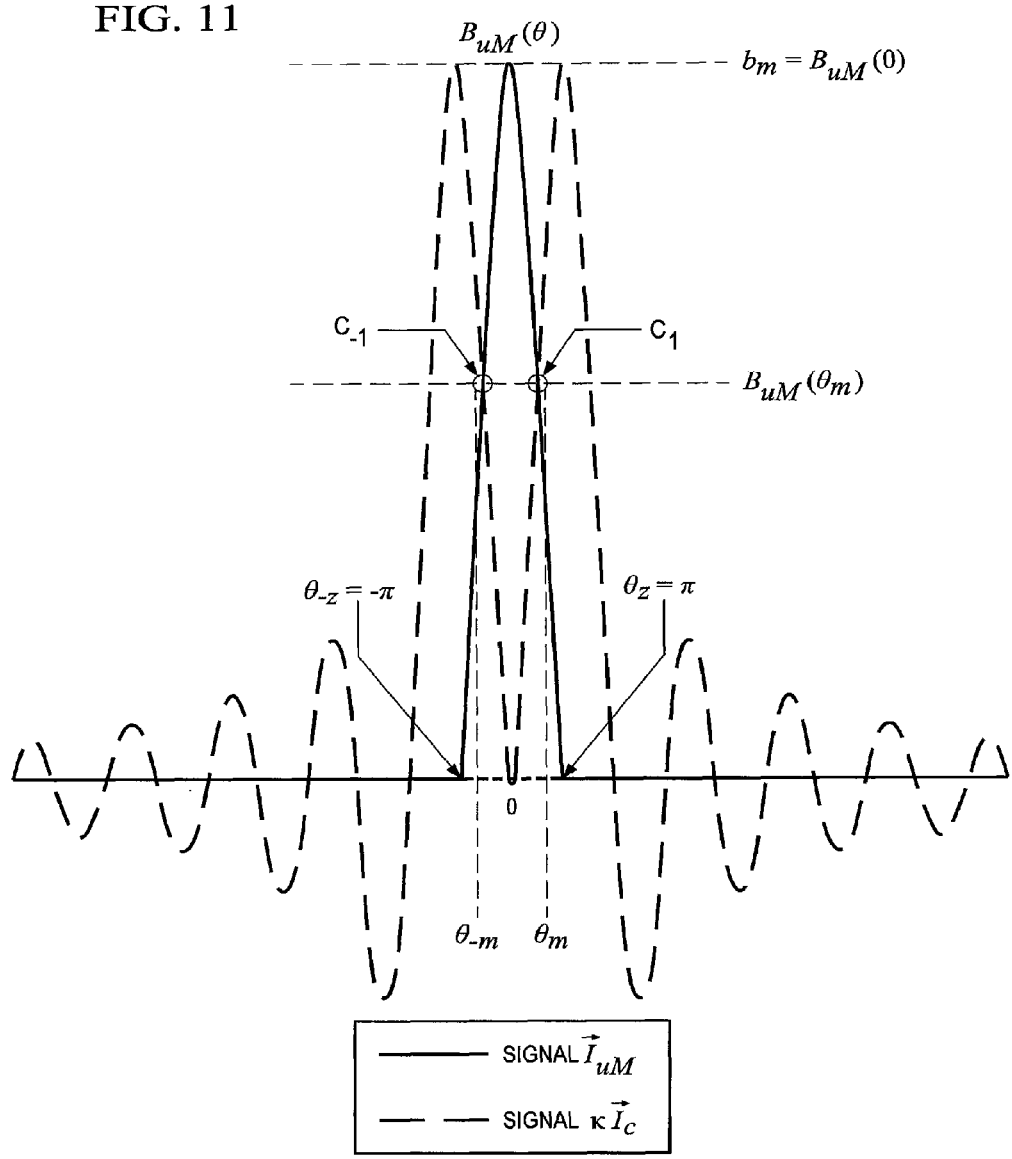
FIG. 11 illustrates the difference between the magnitude of two mainlobe beam signals when a large amplification factor is applied to an auxiliary sample beam of an embodiment herein.

When an amplification factor $\kappa$ is applied to $\vec{I}_c$, only signal from the undesired location is amplified, with little signal being from the desired direction. Thus, the difference between the magnitude of two signals $|\vec{I}_{uM}|$ and $\theta|\vec{I}_c|$ represent a signal from a beam whose mainlobe is effectively narrower when $\kappa$ is large. This property is shown in FIG. 11.

Let the segmented mainlobe be $B_{uM}(\theta)$ and the signal received by $B_{uM}(\theta)$ be $\vec{I}_{uM} = \int B_{uM}(\theta) O(\theta) d\theta = \int_{-\pi}^{\pi} B_{uM}(\theta) O(\theta) d\theta$. $\vec{I}_{uM}$ represents the signal received when the object is weighted summed according to the weight distribution of $B_{uM}(\theta)$ from $\theta = -\pi$ to $\theta = \pi$; where $B_{uM}(\theta \leq -\pi) = 0$, $B_{uM}(\theta \geq -\pi) = 0$. At the look direction of the beam corresponding to the signal $\vec{I}_{uM}$, $b_m$ is maximum gain of beam $B_{uM}(\theta)$ whereas at the same look direction, the signal from the cosine apodized beam $\vec{I}_c(0) = 0$.

Amplifying the signal acquired from the cosine apodized beam with an amplification factor $\kappa$, effectively is equivalent to applying a gain of $\kappa$ to the cosine apodized beam. If the signal received from the cosine apodized beam is subtracted from that of the Sinc beam results in a new beam having the mainlobe shaped by a beam shaping function. This beam shaping function is a function of the gain $\kappa$. Such a beam shaping function not only shapes the mainlobe, but it also modifies the structure of the sidelobe, thus simultaneously reducing its level. Since the cosine apodized beam will intersect with the Sinc beam at $\theta = \pm \theta_m$, at the point of intersection $B_{uM}(\theta_m) = B_c(\theta_m)$. From the above, a component signal $\vec{M}_{n\_m}$, extracted by computing the minimum value between the magnitude of $|I_{DR}|$ and $\kappa|\vec{I}_c|$, has the following properties:

$$\vec{M}_n = \phi(\vec{I}_{DR})\min\{|\vec{I}_{DR}|, \kappa|\vec{I}_c|\} = \phi(\vec{I}_{DR})\min\{||\vec{I}_{uM}| + \vec{I}_{\alpha S}|, \kappa|\vec{I}_c|\} = \vec{M}_{n\_m} + \vec{M}_{n\_S} \text{ where;}$$

$$\vec{M}_{n\_m} = \varphi(\vec{I}_{uM})\min\{|\vec{I}_{uM}|, \kappa|\vec{I}_c|\} = \begin{cases} \varphi(\vec{I}_{uM})\kappa|\vec{I}_c|, \text{ for } |\theta| < \theta_m \\ \varphi(\vec{I}_{uM})|\vec{I}_{uM}|, \text{ for } \pi \geq |\theta| \geq \theta_m \end{cases}$$

where $\phi(\vec{I}_{uM})$ is the phase of the signal $\vec{I}_{uM}$; and $$\vec{M}_{n\_s} = \varphi(\vec{I}_{\alpha S})\min\{|\vec{I}_{\alpha S}|, \kappa|\vec{I}_c|\} = \begin{cases} \varphi(\vec{I}_{\alpha S})\kappa|\vec{I}_c|, & \text{for } \kappa|\vec{I}_c| < |\vec{I}_{\alpha S}|, \\ & \text{at any } \theta \text{ when } |\theta| \geq \pi \\ \varphi(\vec{I}_{\alpha S})|\vec{I}_{\alpha S}|, & \text{for } |\vec{I}_{\alpha S}| < \kappa|\vec{I}_c|, \\ & \text{at any } \theta \text{ when and } |\theta| \geq \pi \end{cases};$$

where $\phi(\vec{I}_{\alpha S})$ is the phase of the signal $\vec{I}_{\alpha S}$.

Thus, component signals $\vec{M}_{n\_m}$ and $\vec{M}_{n\_S}$ vary their property depending upon how the amplified cosine apodized beam is interacted with the mainlobe and the sidelobe of the DR beam, and the morphology of these component beams at the beam amplification factor $\kappa$.

Assume the case that $\kappa$ is chosen large enough such that $\vec{M}_{n\_S} = \phi(\vec{I}_{\alpha S})|_{\alpha S}|$. If the signal $\vec{M}_n$ is subtracted from $\vec{I}_{DR}$, all signals received from the sidelobes $|\vec{I}_{\alpha S}|$ as will be removed. Also, as a result from the subtraction process, a new null is created at $\pm \theta_m$ where beams $\vec{I}_{uM}$ and $\kappa \vec{I}_c$ are intersected $(B_{uM}(\theta_m) = B_c(\theta_m)$, as shown in FIG. 11). This is effectively equivalent to splitting the signal from the mainlobe of the DR beam $\vec{T}_{uM}$ (in the region $-\pi \geq \theta \geq \pi$ where the mainlobe of the beam is bounded) into two new signal components; one is from a newly formed narrowed mainlobe, $\vec{T}_{uM\_m}$ which is bounded by $\theta_{-m} < \theta < \theta_m$ and $\theta_m \leq \pi$; the other $\vec{T}_{uM\_s}$ is from a newly formed two sidelobes that are in the region of $\pi \geq \theta > \theta_m$ and $-\pi \leq \theta < -\theta_m$.

Constructing an image using signals acquired from a beam of a narrower mainlobe improves the image quality. However, completely eliminating the component signal from the segmented sidelobe in a subtraction process may introduce a hole in an image that degrades the image quality. For better control, the amount of component signal being subtracted from the DR beam, a parameter $\eta \leq 1$ is introduced according to embodiments, wherein $\eta \vec{M}_n$ represents a fraction of signal $|\vec{M}_n|$ removed from the DR beam to synthesize a desired high quality beam.

As an amount of signal $\eta \vec{M}_n$ is subtracted from signal received from the DR beam $\vec{T}_{uM}$, the new signal is effectively equivalent to being received from a beam having the mainlobe shaped by a beam shaping function. The mainlobe of this processed beam is shaped to result in narrower mainlobe and the sidelobe is reduced by this function. For example, $$\vec{I}_X = \vec{I}_{DR} - \eta \vec{M}_n =$$

$$\begin{cases} 0; & \text{for } |\theta| = \theta_m, \\ & \text{a new null created in the main lobe} \\ \varphi(\vec{I}_{uM})(|\vec{I}_{uM}| - \eta\kappa|\vec{I}_c|) = & \\ \varphi(\vec{I}_{uM})|\vec{I}_{uM}|\left(1 - \eta\kappa \frac{|\vec{I}_c|}{|\vec{I}_{uM}|}\right); & \text{for } |\theta| < \theta_m, \\ & \text{a new main lobe} \\ \varphi(\vec{I}_{uM})(1-\eta)|\vec{I}_{uM}|; & \text{for } \theta_m < |\theta| \leq \pi; \\ & \text{residual side lobe split form the main lobe} \\ (1-\eta)\vec{I}_{\alpha S}; & \text{for } |\theta| > \pi; \\ & \text{all side lobes} \end{cases}$$

Notice that the above shows the mainlobe $|\vec{T}_{uM}|$ being shaped by a shaping function $\psi_s(\theta)$ result in a new mainlobe $\vec{T}_{uM\_m}$ in the region $|\theta| < \theta_m$. This new mainlobe may be represented as $$\vec{I}_{uM\_m} = \varphi(\vec{I}_{uM})|\vec{I}_{uM}|\psi_s(\theta) =$$

$$\varphi(\vec{I}_{uM})|\vec{I}_{uM}|\left(1 - \eta\kappa \frac{|\vec{I}_c|}{|\vec{I}_{uM}|}\right) = \vec{I}_{uM}\left(1 - \eta\kappa \frac{\int_{-\theta_m}^{\theta_m} B_c(\theta)O(\theta)d\theta}{\int_{-\theta_m}^{\theta_m} B_{uM}(\theta)O(\theta)d\theta}\right) =$$

$$\int_{-\theta_m}^{\theta_m} B_{uM}(\theta)O(\theta)d\theta - \eta\kappa \int_{-\theta_m}^{\theta_m} B_c(\theta)O(\theta)d\theta.$$

Since the gain of the mainlobe of the Sine beam $B_{uM}(\theta)$ is not zero when $|\theta| < \theta_m$ $$\vec{I}_{uM\_m} = \int_{-\theta_m}^{\theta_m} \left(1 - \eta\kappa \frac{B_c(\theta)}{B_{uM}(\theta)}\right) B_{uM}(\theta)O(\theta)d\theta =$$

-continued $$\int_{-\theta_m}^{\theta_m} \psi(\theta)B_{uM}(\theta)O(\theta)d\theta = \int_{-\theta_m}^{\theta_m} B_{uM\_m}(\theta)O(\theta)d\theta$$

where $B_{uM\_m}(\theta) = \psi(\theta)B_{uM}(\theta)$ and $$\psi(\theta) = \left(1 - \eta\kappa \frac{B_c(\theta)}{B_{uM}(\theta)}\right).$$

This shows the main beam is shaped according to the ratio of the gain of the cosine apodized beam and that of the Sine beam in the region defines the beam intersection point $\theta_m$ and $|\theta| < \theta_m$. The morphology of the shaped beam will depend on the parameters $\eta$ and $\kappa$.

Figure 12:
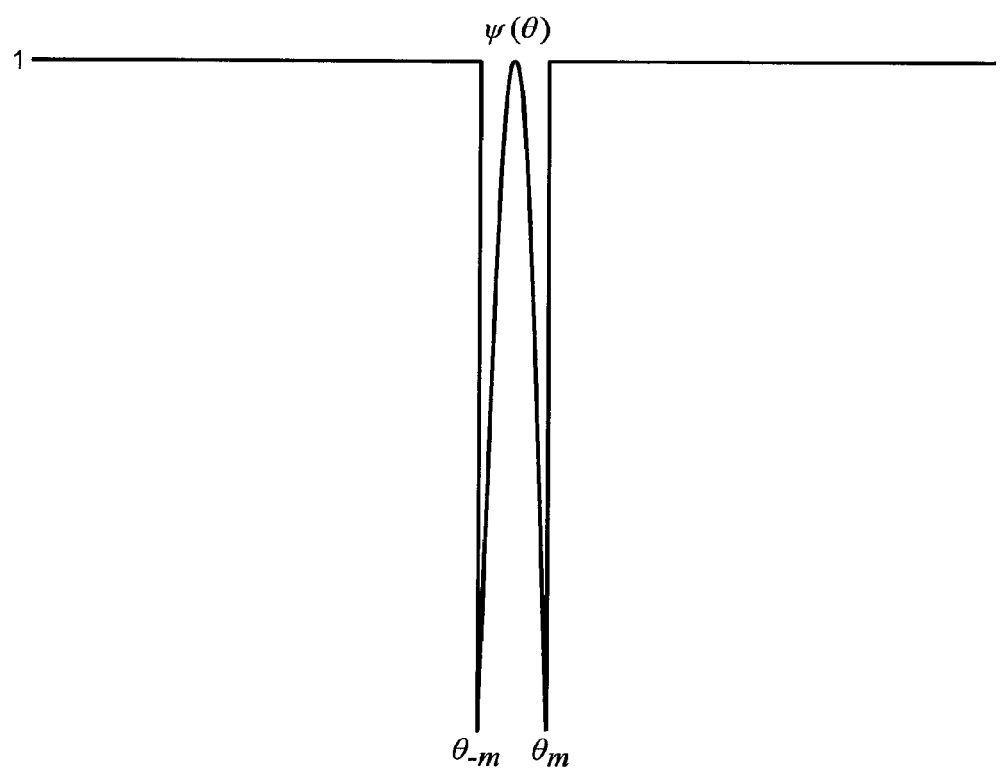
FIG. 12 shows one example of a beam shaping function utilized according to an embodiment of the invention.

The foregoing shows the mainlobe of the DR beam is modified by a beam shaping function $\psi(\theta)$ (illustrated graphically in FIG. 12) when $|\theta| < \theta_m$. The shaping function $\psi(\theta)$ of embodiments has the following properties:

1. $\psi(0) = 1$ since $B_c(0) = 0$; in other words, at the desired look direction, the gain of the beam is maximized and not altered in the signal processing.

2. When $\eta$ and $\kappa$ are both zeroes, the morphology of the beam is the same as the DR beam and $\psi(\theta) = 1$ for all $\theta$.

3. Since $B_c(\theta)$ is smaller than $B_{uM}(\theta)$ in the mainlobe region, then $\psi(\theta) < 1$ when $|\theta| \leq \theta_m$. Thus, beam $B_{uM\_m}(\theta)$ is always narrower than beam $B_{uM}(\theta)$ 4. Since both $B_c(\theta)$ and $B_{uM}(\theta)$ are symmetrical at the beam look direction, the beam shaping function is a symmetrical function.

The beam shaping function $\psi(\theta)$ changes the gain of the beam in the region $|\theta| \leq \theta_m$. The amount and the morphology of the shaping beam will depend on the parameters $\eta$ and $\kappa$. when both $\eta$ and $\kappa$ are zeroes. Since both $B_c(\theta)$ and $B_{uM}(\theta)$ are symmetrical at the beam look direction, the beam shaping function $\psi(\theta)$ is a symmetrical function. Since $|\theta_m| \leq \pi$, the beam width of $B_{uM}(\theta)$ is always narrower than that of $B_{uM}(\theta)$.

The foregoing component signals $\vec{M}_{n\_m}$ and $\vec{M}_{n\_S}$ vary depending upon how the amplified cosine apodized beam is interacted with the mainlobe and the sidelobe of the DR beam and the morphology of these component beams at amplification factor $\kappa$. When the amplification factor $\kappa$ is small, location of $\pm\theta_m$ is closer to $\pm\pi$. Thus, the mainlobe of the processed beam will be relatively less narrowing as compared to that from the processed beam with large amplification $\kappa$. When the amplification factor $\kappa$ is small, interaction between the cosine apodized beam and the sidelobe of the DR beam is more complicated. The morphology of the sidelobes of the processed beam will depend on the relative amplitude of the sidelobe of the DR beam $|\vec{T}_{\alpha S}|$ and the magnitude of the sidelobe of the cosine apodized beam after an amplification factor is applied $\kappa|\vec{T}_c|$, since the signal from the component $|\vec{M}_{n\_S}|$ is preferably set in-phase with the DR beam and its magnitude represents the smaller of the two signals $|\vec{T}_{\alpha S}|$ and $\kappa|\vec{T}_c|$. Therefore, when $|\vec{M}_{n\_S}|$ is subtracted from the DR beam, the signal of the sidelobe will always be smaller that results in suppression the sidelobe.

The subtraction process for segmenting the component signals suggests that the phase of both the subtrahend and the minuend signals should be kept identical. For imaging applications where only the magnitude of the signal is of interest, it is equally effective in implementation of magnitude only operations. In this case, it is desired that the sign of the signal of both the subtrahend and the minuend signals are kept identical. In other words, replacing any operation of $\phi(\vec{T}_\bullet)$ by $\text{sign}(\vec{T}_\bullet)$ in the DR/XDR process. For example, replacing $\phi(\vec{T}_\alpha)$ by $\text{sign}(\vec{T}_\alpha) = \text{sign}(\text{real}(\vec{T}_\alpha)) + i*\text{sign}(\text{imag}(\vec{T}_\alpha))$ when the algorithm is implemented to process the beamformed signals after they are quadrature band-passed and decimated into real and imaginary data stream. In this context, $\text{real}(\vec{T}_\alpha)$ stands for real part of the signal $\vec{T}_\alpha$ and $\text{imag}(\vec{T}_\alpha)$ is the imaginary part of the signal $\vec{T}_\alpha$. By doing so, the DR/XDR process operates on the real part and the imaginary part of the bandpassed data separately. The processed signal components will also comprise two parts, the real part $\text{real}(\vec{T}_x)$ and the imaginary part of $\text{imag}(\vec{T}_x)$. Then the real part and the imaginary part of the processed signal are recombined into $\vec{T}_x = \text{real}(\vec{T}_\alpha) + i*\text{imag}(\vec{T}_\alpha)$. Signal $\vec{T}_x$ is then detected, compressed and scan-converted into the resultant image video.

For 2D gray scale imaging only applications, however, the phase of the signal can be neglected in the DR/IDR/XDR process. In this case, only the magnitude of signals is needed in the DR/IDR/XDR process. Furthermore, in the XDR process, instead of processing the magnitude of the signals, signal power can be used to reduce the computation. Since a division and detection process is incorporated in the DR process of embodiments, the computational cost may be relatively high. For low cost implementation, the DR process may be skipped, trading performance for cost or speed.

The algorithm can also be implemented before the signal is quadrature band-passed. Then in the signal subtraction process, $\phi(I_{RF})$ is replaced by $\text{sign}(I_{RF})$ for the effective component signal segmentation.

As previously described, the signal received from the mainlobe of the Sinc beam can be $\vec{T}_{um}$ segmented by processing the signals $\kappa|\vec{T}_c|$ and $|\vec{T}_1|$ when $\kappa=1$. Subsequently, $\vec{T}_{um}$ can be further split by processing the signals $\kappa|\vec{T}_c|$ and $|\vec{T}_{um}|$ by setting $\kappa>1$. When $\kappa$ is set to a value smaller than 1, for example, setting $\kappa=0.22225$; one may also form a beam with the mainlobe size approximately equal to the Hanning beam. This broader mainlobe can be further split using the process as described previously. A new beam can then be synthesized with different component signal.

Figure 13A:
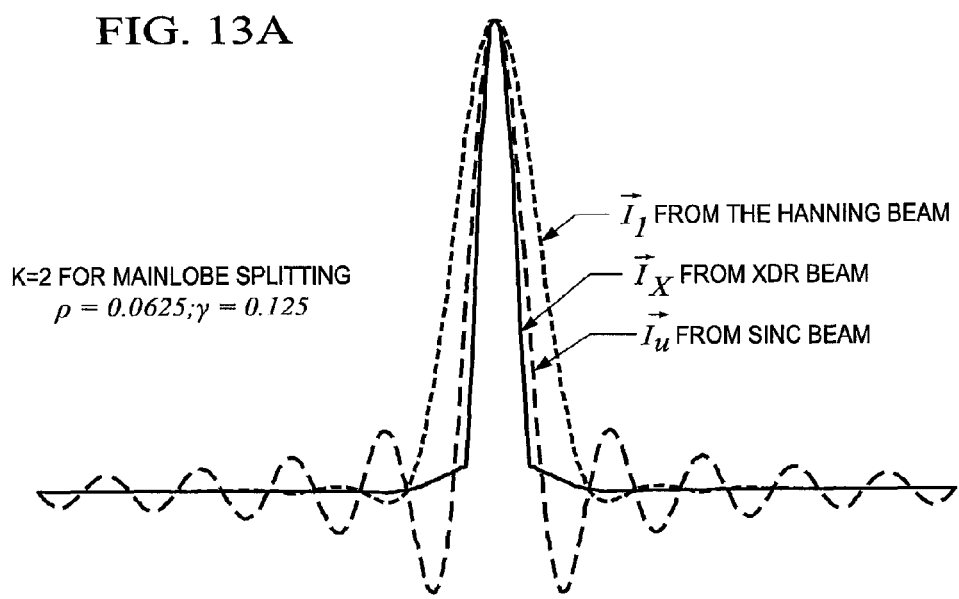
FIGS. 13A and 13B show mainlobe splitting to reduce the residual mainlobe the sidelobe of a dynamic resolution beam and the resulting beam.
Figure 13B:
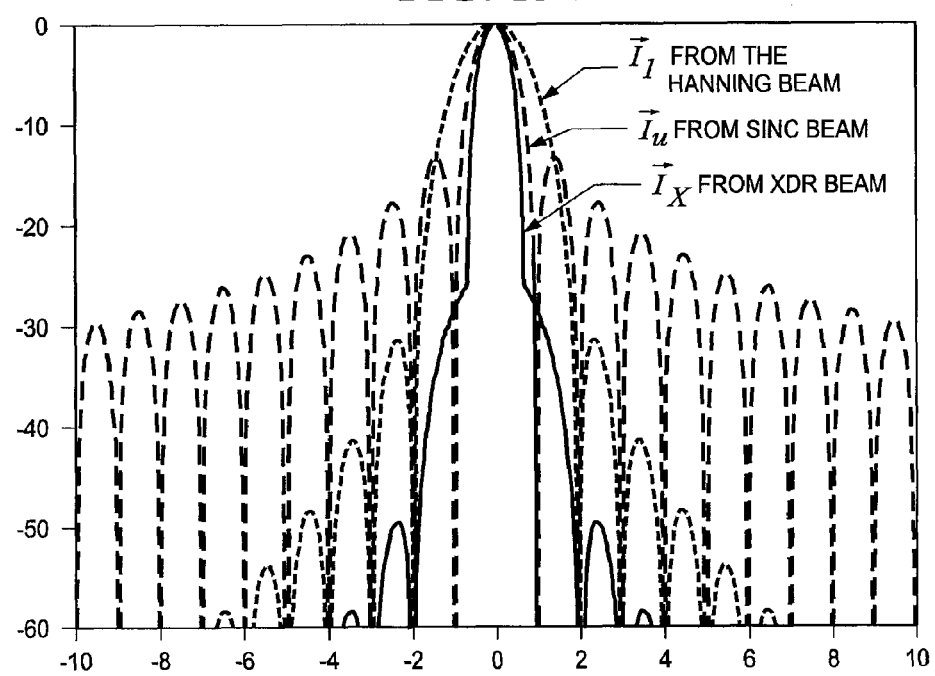

Removing the foregoing component signals from the signal obtained from the DR beam effectively creates a beam sharpening function. This function sharpens the mainlobe and reduces the sidelobe of the processed beam. FIG. 13A shows the mainlobe being split using $\kappa=2$, setting $\rho=0.0625$ to reduce the residual mainlobe, and setting $\gamma=0.125$ to reduce the sidelobe of the DR beam which is the sidelobe of the $\vec{T}_1$ in this case. The resulting signal $\vec{T}_x = \mu \vec{T}_{n\_m} + \rho \vec{T}_{n\_s} + \gamma I_{\alpha S}$ and its corresponding beam are depicted in FIG. 13B. It is important to note that because of the reduction in artifacts allowed by the narrowing of the mainlobe and the attenuation of sidelobes, it would be advantageous to over sample the object of interest thereby achieving a sharper display image than is currently possible.

Figure 14:
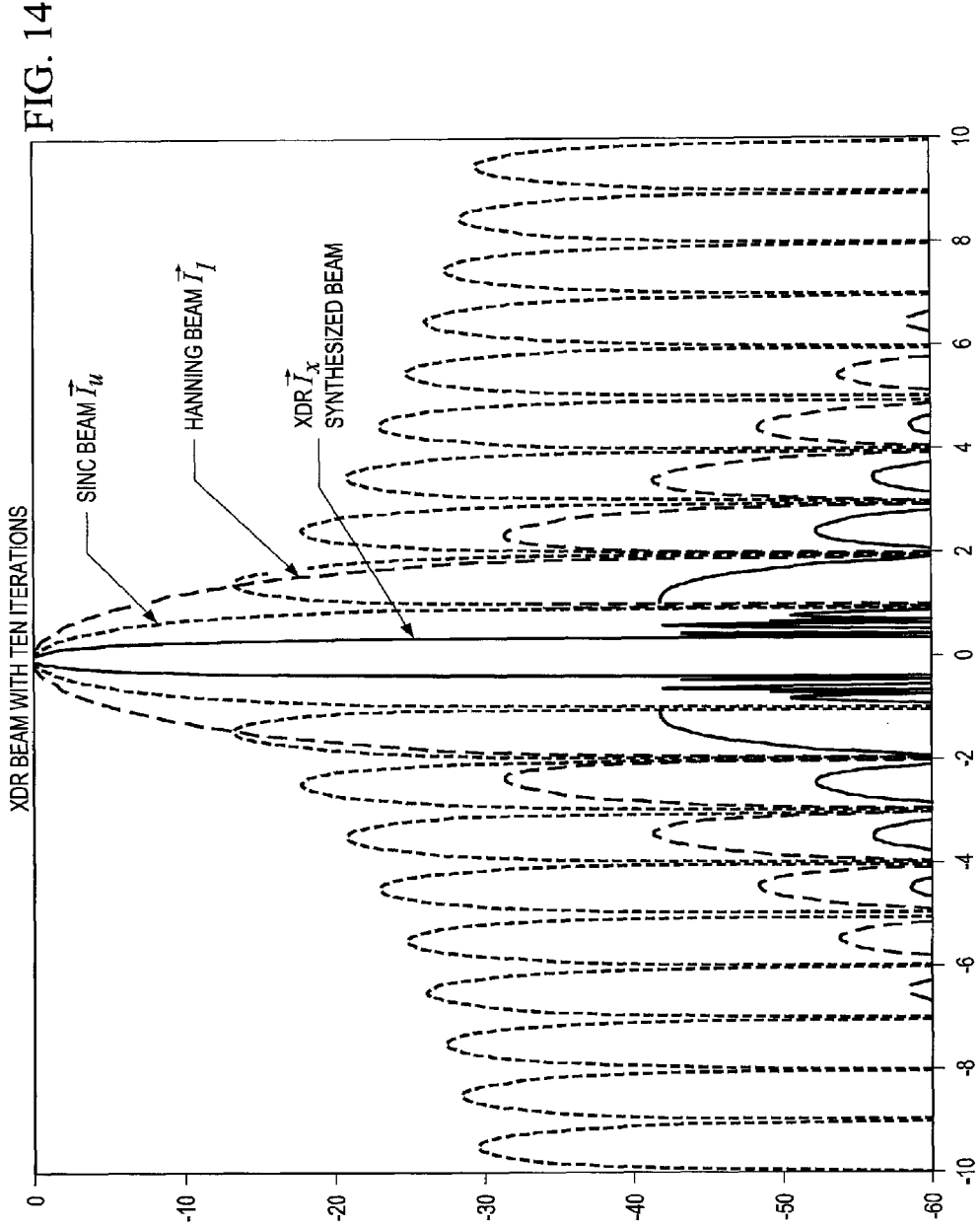
FIG. 14 shows an example of an enhanced dynamic resolution beam after multiple iterations of an embodiment of the present invention.

It should be appreciated that the process of taking the minimum signal between the DR beam with an amplified cosine apodized beam at different amplification factors and setting the phase of the minimum signal to be in-phase with the DR beam can be applied again and again to obtain a signal corresponding to a beam with desired mainlobe of narrow width and desired low sidelobe level. That is, the XDR beam synthesis process of segmenting a signal into components and shaping the beam using different amplification factors $\kappa$, sidelobe reduction parameters $\gamma$ and beam shaping parameter $\eta$ can be repetitively applied to the processed beam to obtain a new processed beam with desired mainlobe and sidelobe properties. These properties may be defined according to imaging parameters such as detailed resolution, contrast resolution and dynamic range in the imaging process. Beams after 10 iterations with different processing parameters are shown in FIG. 14.

More sidelobe level control can be achieved by attenuating (e.g., multiply by an attenuation factor that is smaller than one) the segmented residual sidelobe of the mainlobe if desired. For example, the gain and attenuation factor in the DR and XDR process can also be set as a function of $\alpha$ to adapt to power of the sidelobe at every sample.

The analysis described above is based on geometrical properties among the narrow band formulation of the Sinc beam, the cosine apodized beam, the Hanning beam, and other beams. However, it can be proved and experimentally shown that the concepts herein are similarly effective when broadband signal is beamformed and processed as for general imaging application. Moreover, the concepts can be directly applied to spectral analysis, two dimensional array beamforming, multiple-beam spatial compounding, and multi-beam parallel beamforming.

Note that it is possible to use variations of the implementation of the DR/IDR/XDR techniques herein to achieve different results. For example, the vector format may be represented by real and imaging parts and DR, IDR, and XDR can be processed in real and imaginary parts separately. To keep the phase unchanged is equivalent to keeping the sign of the real or the sign of the imaginary part unchanged. Magnitude only processing in RF domain can be accomplished by keeping the sign of the signal unchanged instead of keeping the phase unchanged.

Different sequences of applying gain and attenuation factors or representing gain or attenuation as a mathematical functions can be achieved, if desired. Forming a beam for constant $\alpha$ (any $\alpha \le 1$) followed by an XDR process for resolution enhancement and sidelobe suppression. Using two beams, an embodiment may apply min to segment component beams or component signals and then compounding component signals to synthesize new beams, using gain and attenuation factors to construct a new beam.

Embodiments may recursively form new beams with multiple gain and attenuation factors to arrive at a new high performance beam. Thus, the concept applies to higher dimensional beamforming. For example:

Let $\kappa_j$ be an amplification factor for the signal from the cosine apodized beam $\vec{T}_c$ and $0 < \kappa_j \le \kappa_{max}$;
Let $\mu$ be enhancement factor of processed mainlobe; $\mu_j \ge 1$;
Let $\rho$ be attenuation factor of processed sidelobe; $|\rho_j| \le 1$;

$$\kappa = [\kappa_1 \kappa_2 \ldots \kappa_n]; \mu = [\mu_1 \mu_2 \ldots \mu_n]; \rho = [\rho_1 \rho_2 \ldots \rho_n];$$

Start

Let $\vec{T}_1 = \vec{T}_{\alpha DR}$; set the first processed signal from the processed beam be $\vec{T}_1$ j=1
while j<n
Calculate $$(\text{real}(\vec{M}_n) = \text{sign}(\text{real}(\vec{T}_j)) * \min(k_j * |\text{real}(\vec{T}_c)|, |\text{real}(\vec{T}_j)|);$$

$$\text{imag}(\vec{M}_n) = \text{sign}(\text{imag}(\vec{T}_j)) * \min(k_j * |\text{imag}(\vec{T}_c)|, |\text{imag}(\vec{T}_j)|);$$

real($\vec{I}_M$)=real($\vec{I}_j$)−real($\vec{M}_n$);imag($\vec{I}_M$)=
imag($\vec{I}_j$)−imag($\vec{M}_n$);

real($\vec{I}_S$)=real($\vec{M}_n$);imag($\vec{I}_S$)=imag($\vec{M}_n$);

Method 1 real($\vec{I}_S$)(|real($\vec{I}_j$)|>|real($\vec{M}_n$)|)=0:imag($\vec{I}_S$)
(|imag($\vec{I}_j$)|>|imag($\vec{M}_n$)|)=0;

Method 2 real($\vec{I}_{j+1}$)=μ$_j$*real($\vec{I}_M$)+ρ$_j$*real($\vec{I}_S$);
imag($\vec{I}_{j+1}$)=μ$_j$*imag($\vec{I}_M$)+ρ$_j$*imag($\vec{I}_S$);

$j=j+1$;

end

Output real($\vec{I}_n$); and imag($\vec{I}_n$).

Exemplary DR/IDR/XDR Beam Synthesis Algorithms

To aid in understanding the concepts of the present invention described above, an exemplary DR/IDR/XDR beam synthesis algorithm as may be implemented by DR/IDR/XDR beam synthesis processor 214 of FIGS. 2A, 2B, 5A and 5B is provided below. It should be appreciated that the algorithm set forth is but one example of an algorithm which is operable to provide DR/IDR/XDR beam synthesis in accordance with the concepts of the present invention.

Let $\vec{I}_c$ be the signal from cosine apodized beam at the xth beam and the yth sample;

Let $\vec{I}_u$ be the signal from Sine beam at the xth beam and the yth sample;

Extract signal $\vec{I}_\alpha$ sample by sample by computing $$\alpha = -\frac{\vec{I}_c \cdot \vec{I}_u}{|\vec{I}_u|^2};$$

if α>1, set α=1, α<0, set α=0,
Then compute $\vec{I}_\alpha = \vec{I}_u + \alpha \vec{I}_c$;

If IDR beam synthesis is desired, then start the IDR process as follows:

$$M_n = \min\{|\vec{I}_\alpha|, |\vec{I}_c|\} = \begin{cases} |\vec{I}_c|, & \text{for } \theta \leq \pi \\ |\vec{I}_\alpha|, & \text{for } \theta > \pi \end{cases};$$

Segment into component signals $\vec{I}_{\alpha M} = \vec{I}_\alpha - M_n; \vec{I}_{\alpha S} = \vec{I}_\alpha - \vec{I}_{\alpha M} = M_n$;

Compounding signals $\vec{I}_{\alpha M}$ and $\vec{I}_{\alpha S}$ into a new signal (synthesized IDR beam signal);

$\vec{I}_{\alpha DR} = \vec{I}_{\alpha M} + \gamma_S \vec{I}_{\alpha S}$;

If XDR beam synthesis is desired, then start the XDR process as follows:

$\vec{M}_{n\_1} = \phi(\vec{I}_{\alpha DR}) * \min(\kappa * |\vec{I}_c|, |\vec{I}_{\alpha DR}|)$;

$\vec{I}_{\alpha M\_1} = \vec{I}_{\alpha DR} - \vec{M}_{n\_1}$;

Form a new sidelobe component $\vec{I}_{\alpha n\_s} = \vec{I}_{\alpha M} - \vec{I}_{\alpha M\_1}$;

Form the XDR beam $\vec{I}_{XDR} = \vec{I}_{\alpha M\_1} + \rho \vec{I}_{\alpha n\_s} + \gamma \vec{I}_{\alpha s}$;

To form an XDR beam using an iterative method according to embodiments of the invention:

Method 1

Let κ$_j$ be an amplification factor for the signal from the cosine apodized beam $\vec{I}_c$ and 0<κ$_j$≤κ$_{max}$;
Let μ be enhancement factor of processed mainlobe μ≥1;
Let ρ$_j$ be attenuation factor of processed sidelobe;

ρ$_j$≤1,κ=[$k_1 k_2 \ldots k_n$];ρ=[ρ$_1$ρ$_2 \ldots$ρ$_n$];

Start
Set the first processed signal from the processed beam to be $\vec{I}_1$ and save the IDR mainlobe component $\vec{I}_{\alpha M}$ in the buffer $\vec{I}_r$.

Let $\vec{I}_1 = \vec{I}_{\alpha DR}$ and $\vec{I}_r = \vec{I}_{\alpha M}$;
Let the XDR beam comprise of only the sidelobe component;

Let $\vec{I}_{XDR} = \gamma \vec{I}_{\alpha S}$;
j=1
while j<n
Calculate $$\vec{M}_{n\_j} = \phi(\vec{I}_{\alpha DR}) * \min(\kappa_j * |\vec{I}_c|, |\vec{I}_{\alpha DR}|); \lim_{x \to \infty}$$

$\vec{I}_{\alpha m\_j} = \vec{I}_{\alpha DR} - \vec{M}_{n\_j}$;

$\vec{I}_{n\_s} = \vec{I}_r - \vec{I}_{\alpha m\_j}$;

$\vec{I}_{XDR} = \vec{I}_{XDR} + \rho_i \vec{I}_{n\_s}$;

$\vec{I}_r = \vec{I}_{\alpha m\_j}$;

$j = j+1$;

end $\vec{I}_{XDR} = \vec{I}_{XDR} + \mu * \vec{I}_{\alpha m\_n}$;

Method 2

Let κ$_j$ be an amplification factor for the signal from the cosine apodized beam $\vec{I}_c$ and 0<κ$_j$≤κ$_{max}$;
Let μ$_j$ be enhancement factor of processed mainlobe; μ$_j$≥1;
Let ρ be attenuation factor of processed sidelobe;

ρ$_j$≤1;

κ=[$k_1 k_2 \ldots k_n$];μ=[μ$_1$μ$_2 \ldots$μ$_n$];ρ=[ρ$_1$ρ$_2 \ldots$ρ$_n$];

Start
Let $\vec{I}_1 = \vec{I}_{\alpha DR}$; set the first processed signal from the processed beam be $\vec{I}_1$ j=1
while j<n
Calculate $\vec{M}_n = \phi(\vec{I}_j) * \min(k_j * |\vec{I}_c|, |\vec{I}_j|)$;

$\vec{I}_M = \vec{I}_j - \vec{M}_n$;

$\vec{I}_S = \vec{M}_n$;

$$\vec{T}_{j+1} = \mu_j * \vec{T}_M + \rho_j * \vec{T}_S;$$

$$j = j+1;$$

end

Output $\vec{T}_n$

Referring again to FIG. 6, in implementing the foregoing exemplary methods as signals from the nth Sinc beam and cosine apodized beam at depth z: $\vec{T}_u(n,z)$ and $\vec{T}_c(n, z)$ are acquired in 601, the beamforming parameter α is then computed in 62 according to a criterion that the power of $|\vec{T}_{\alpha 1}|^2 = |\vec{T}_u + \alpha \vec{T}_c|^2$ is minimized and the DR beam $\vec{T}_{\alpha DR} = \vec{T}_\alpha$ is formed in 603.

Parameter α is then passed through Look up table 63 to obtain the beamforming parameters $\mu_i$, $\rho_i$, $\kappa_i$, $\gamma_m$ and $\gamma_S$ useful for IDR and XDR beam decomposition and synthesis that are appropriate for an imaging application. Since the parameter α indicates the relative amount of the desired signal and the undesired clutter at a sample location (n, z), clutter is small as α is small and large as α is large, parameters $\mu_i$, $\rho_i$, $\kappa_i$, $\gamma_m$ and $\gamma_S$ useful for IDR and XDR beam decomposition and synthesis can be a function of α.

The desired properties of a synthesized beam for best image quality vary depending upon a number of system parameters such as: the element pitch of the scan head, the number of channels available in the beamformer, the line density in an image, the number of parallel beams being used, the frequency and bandwidth of the signal of insonification, . . . , etc.; thus different sets of parameters $\mu_i(\alpha)$, $\rho_i(\alpha)$, $\kappa_i(\alpha)$, $\gamma_m(\alpha)$ and $\gamma_S(\alpha)$ are preferred for different imaging applications. The particular functional relationship can be experimentally determined based upon the image characteristics desired, the objects being imaged, the configuration of the imaging system, etc.

The DR beam $\vec{T}_{\alpha DR}$, and parameters $\mu_i$, $\rho_i$, $\kappa_i$, $\gamma_m$, $\gamma_S$ are used in processor 603 to form the desired IDR beam. The DR beam, the IDR beam and the beamforming parameters can also be used to iteratively form XDR beam in processors 604 and 605.

FIGS. 6L(1)-6L(4) show an example decomposing a DR beam of α=1 using parameters κ=2, ρ=0.125, γ=0.015625, n=1 to synthesize an XDR beam by computing $\vec{T}_{XDR} = \vec{T}_{\alpha M\_K} + \rho \vec{T}_{\alpha n\_s} + \gamma \vec{T}_{\alpha s}$ using Method 1, described above. The 3 db FWHM is 0.71227π which is 21.6% narrower than that of the Sinc beam. Since for α=1, the DR beam is a Hanning beam whose peak sidelobe level is −31 db. In the XDR beam synthesis process, the parameter γ is used to attenuate the Hanning sidelobe 20*log 10(γ)=−36.12 db that results in −31+20*log 10(γ)=−67.12 as shown in FIG. 6L(4). The sidelobe roll-off rate of the synthesized XDR beam is the same as the Hanning beam at −18 db/octave.

Consistent with the foregoing dynamic resolution beam synthesis techniques, DR/IDR/XDR beam synthesis of embodiments performs the following operations in synthesizing XDR dynamic resolution beam signals, wherein the signal acquired from the nth Sinc beam at depth z: $I_u(n,z) = I_{ur}(n,z) + jI_{ui}(n,z)$ and the signal acquired from the nth cosine apodized beam at depth z: $I_c(n,z) = I_{cr}(n,z) + jI_{ci}(n,z)$:

For $\|I_c(n,z)\| \neq 0$;

calculate $$\alpha(n, z) = -\frac{I_{ur}(n, z)I_{cr}(n, z) + I_{ui}(n, z)I_{ci}(n, z)}{I_{cr}^2(n, z) + I_{ci}^2(n, z)};$$

compute $I_{DR}(n,z) = I_u(n,z) + \alpha I_c(n,z)$;

Let $I_{DR\_r}(n,z) = \text{real}(I_{DR}(n,z)); I_{DR\_i}(n,z) = \text{imag}(I_{DR}(n,z))$;

Let $I_{c\_r}(n,z) = \text{real}(I_c(n,z)); I_{DR\_i}(n,z) = \text{imag}(I_c(n,z))$;

Let $sI_r = \text{sign}(I_{DR\_r}); sI_i = \text{sign}(I_{DR\_i})$ compute $mI_r = sI_r * \min(|I_{DR\_r}(n,z)|, \kappa|I_{c\_r}(n,z)|)$;

$mI_i = sI_i * \min(|I_{DR\_i}(n,z)|, \kappa|I_{c\_r}(n,z)|)$;

set $I_{XDR}(n,z) = I_{DR}(n,z)$;

if $\text{sign}(I_{DR\_r}(n,z)) * \text{sign}(I_{cr}(n,z)) > 0 \& mI_r \neq |I_{DR\_r}(n;z)|$ $I_{XDR\_r}(n,z) = I_{DR\_r}(n,z) + (\rho-1)mI_r(n,z)$ end if $\text{sign}(I_{DR\_i}(n,z)) * \text{sign}(I_{ci}(n,z)) > 0 \& mI_i \neq |I_{DR\_i}(n,z)|$;

$I_{XDR\_i}(n,z) = I_{DR\_i}(n,z) + (\rho-1)mI_i(n,z)$;

end.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method of operating an ultrasound system, the method comprising:
   segmenting a beam signal into a mainlobe component and a sidelobe component:
   independently processing at least one of the mainlobe component and the sidelobe component; and
   recombining the mainlobe component and the sidelobe component as independently processed, wherein recombining the mainlobe component and the sidelobe component provides synthesizing of a beam having a desired shape and geometrical properties, and wherein the desired shape and geometrical properties of the synthesized beam comprise a sharper mainlobe than the segmented beam and a sidelobe adapted to provide a balance between mainlobe resolution and sidelobe level for improved image quality.

2. The method of claim 1, wherein the independently processing at least one of the mainlobe component and the sidelobe component comprises weighting the at least one of the mainlobe component and the sidelobe component differently than the other one of the mainlobe component and the sidelobe component.

3. The method of claim 2, wherein the weighting the at least one of the mainlobe component and the sidelobe component differently comprises weighting the sidelobe component to have a lesser weighting than a weighting of the mainlobe component for the recombining.

4. The method of claim 1, wherein the recombining the mainlobe component and the sidelobe component comprises combining a non-null sidelobe component with the mainlobe component.

5. The method of claim 1, wherein the beam signal which is segmented into the mainlobe component and the sidelobe component is provided by a synthesized beam technique.

6. The method of claim 5, wherein the synthesized beam technique comprises:
   obtaining a first signal using a first sample beam having a first mainlobe and one or more sidelobe;
   obtaining a second signal using a second sample beam having a second mainlobe and one or more sidelobe, wherein a shape of the first mainlobe is substantially different than a shape of the second mainlobe; and
   synthesizing a beam to provide the beam signal using the first signal and the second signal and a weighting factor.

7. The method of claim 6, wherein the first sample beam comprises an unapodized beam and the second sample beam comprises an apodized beam.

8. The method of claim 7, wherein the first sample beam comprises a Sinc beam and the second sample beam comprises a cosine apodized beam.

9. The method of claim 6, further comprising selecting the weighting factor to provide the synthesized beam having one or more reduced sidelobe as compared to the first and second sample beams.

10. The method of claim 9, wherein the selecting the weighting factor further comprises selecting the weighting factor to provide an acceptable balance between the reduced sidelobe of the synthesized beam and increased mainlobe width as compared to the first sample beam.

11. A method of operating an ultrasound system, the method comprising:
   segmenting a beam signal into a mainlobe component and a sidelobe component;
   independently processing at least one of the mainlobe component and the sidelobe component;
   recombining the mainlobe component and the sidelobe component as independently processed; and
   repeating the segmenting, independently processing, and recombining for a plurality of cycles to optimize detail and contrast resolution in an image generated using signals from the recombined mainlobe and sidelobe components.

12. The method of claim 11, wherein the recombining the mainlobe component and the sidelobe component provides synthesizing of a beam having a desired shape and geometrical properties.

13. The method of claim 11, wherein the plurality of cycles comprise a plurality of look directions.

14. A method of operating an ultrasound system, the method comprising:
   segmenting a beam signal into a mainlobe component and a sidelobe component;
   applying a beam sharpening function to the mainlobe component, wherein the beam sharpening function comprises subtracting a weighted component of a sample beam signal from the mainlobe component; and
   recombining the mainlobe component and the sidelobe component after application of the beam sharpening function to the mainlobe component.

15. The method of claim 14, wherein the subtracting the weighted component of the sample beam signal comprises taking a minimum of the weighted component of the sample beam signal and the mainlobe.

16. The method of claim 14, wherein the subtracting the weighted component of the sample beam signal comprises iteratively subtracting differently weighted sample beam components from the mainlobe component.

17. The method of claim 14, wherein the weighted component of the sample beam comprises a weighted mainlobe component.

18. The method of claim 14, wherein the sample beam comprises a signal provided by an apodized beam.

19. The method of claim 18, wherein the apodized beam comprises an apodized cosine beam.

20. The method of claim 14, wherein the recombining the mainlobe component and the sidelobe component comprises combining a non-null sidelobe component with the mainlobe component.

21. The method of claim 14, wherein the beam signal which is segmented into the mainlobe component and the sidelobe component is provided by a synthesized beam technique.

22. The method of claim 21, wherein the synthesized beam technique comprises:
   segmenting a first beam signal into a mainlobe component and a sidelobe component;
   independently processing at least one of the mainlobe component and the sidelobe component; and
   recombining the mainlobe component and the sidelobe component as independently processed.

23. The method of claim 22, wherein the independently processing at least one of the mainlobe component and the sidelobe component comprises weighting the at least one of the mainlobe component and the sidelobe component differently than the other one of the mainlobe component and the sidelobe component.

24. The method of claim 23, wherein the weighting the at least one of the mainlobe component and the sidelobe component differently comprises weighting the sidelobe component to have a lesser weighting than a weighting of the mainlobe component for the recombining.

25. The method of claim 22, wherein the synthesized beam technique comprises:
   obtaining a first signal using a first sample beam having a first mainlobe and one or more sidelobe;
   obtaining a second signal using a second sample beam having a second mainlobe and one or more sidelobe, wherein a shape of the first mainlobe is substantially different than a shape of the second mainlobe; and
   synthesizing a beam to provide the beam signal using the first signal and the second signal and a weighting factor.

26. The method of claim 25, wherein the first sample beam comprises an unapodized beam and the second sample beam comprises an apodized beam.

27. The method of claim 26, wherein the first sample beam comprises a Sinc beam and the second sample beam comprises a cosine apodized beam.

28. The method of claim 25, further comprising selecting the weighting factor to provide the synthesized beam having one or more reduced sidelobe as compared to the first and second sample beams.

29. The method of claim 28, wherein the selecting the weighting factor further comprises selecting the weighting factor to provide an acceptable balance between the reduced sidelobe of the synthesized beam and increased mainlobe width as compared to the first sample beam.

* * * * *